United States Patent
Rother et al.

(10) Patent No.: US 9,771,418 B2
(45) Date of Patent: Sep. 26, 2017

(54) METHODS FOR TREATING COMPLEMENT-ASSOCIATED DISORDERS

(71) Applicant: Alexion Pharmaceuticals, Inc., New Haven, CT (US)

(72) Inventors: Russell P. Rother, Oklahoma City, OK (US); Camille Bedrosian, Woodbridge, CT (US); Stephen P. Squinto, Bethany, CT (US); Leonard Bell, Woodbridge, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 15/243,290

(22) Filed: Aug. 22, 2016

(65) Prior Publication Data

US 2016/0355579 A1    Dec. 8, 2016

Related U.S. Application Data

(62) Division of application No. 13/128,523, filed as application No. PCT/US2009/063929 on Nov. 10, 2009, now Pat. No. 9,447,176.

(60) Provisional application No. 61/200,640, filed on Dec. 1, 2008, provisional application No. 61/199,562, filed on Nov. 18, 2008, provisional application No. 61/199,563, filed on Nov. 18, 2008, provisional application No. 61/181,788, filed on May 28, 2009, provisional application No. 61/199,569, filed on Nov. 18, 2008, provisional application No. 61/200,635, filed on Dec. 1, 2008, provisional application No. 61/199,764, filed on Nov. 19, 2008, provisional application No. 61/228,047, filed on Jul. 23, 2009, provisional application No. 61/200,634, filed on Dec. 1, 2008, provisional application No. 61/198,803, filed on Nov. 10, 2008.

(51) Int. Cl.
| | |
|---|---|
| *A61K 39/00* | (2006.01) |
| *A61K 9/00* | (2006.01) |
| *C07K 16/18* | (2006.01) |
| *A61K 39/395* | (2006.01) |
| *A61K 45/06* | (2006.01) |
| *A61K 38/00* | (2006.01) |

(52) U.S. Cl.
CPC ............ *C07K 16/18* (2013.01); *A61K 9/0019* (2013.01); *A61K 39/3955* (2013.01); *A61K 45/06* (2013.01); *A61K 38/00* (2013.01); *A61K 2039/505* (2013.01); *A61K 2039/54* (2013.01); *A61K 2039/545* (2013.01); *C07K 2317/24* (2013.01); *C07K 2317/34* (2013.01)

(58) Field of Classification Search
None
See application file for complete search history.

(56) References Cited

U.S. PATENT DOCUMENTS

| | | |
|---|---|---|
| 4,686,100 A | 8/1987 | Raffin et al. |
| 4,987,071 A | 1/1991 | Cech et al. |
| 5,093,246 A | 3/1992 | Cech et al. |
| 5,116,742 A | 5/1992 | Cech et al. |
| 5,135,916 A | 8/1992 | Sims et al. |
| 5,660,825 A | 8/1997 | Sims et al. |
| 6,169,068 B1 | 1/2001 | Levin et al. |
| 6,355,245 B1 | 3/2002 | Evans et al. |
| 7,361,339 B2 | 4/2008 | Bell |
| 7,482,435 B2 | 1/2009 | Bowdish et al. |
| 7,833,525 B2 | 11/2010 | Shenoy et al. |
| 8,241,628 B2 | 8/2012 | Diefenbach-Streiber et al. |
| 9,409,980 B1 | 8/2016 | Zhou et al. |
| 9,447,176 B2 | 9/2016 | Rother et al. |
| 2003/0049683 A1 | 3/2003 | Bowdish et al. |
| 2003/0143204 A1 | 7/2003 | Lewis et al. |
| 2005/0036991 A1 | 2/2005 | Fodor |
| 2005/0191298 A1 | 9/2005 | Bell et al. |
| 2005/0221382 A1 | 10/2005 | Rother |
| 2005/0271660 A1 | 12/2005 | Wang |

(Continued)

FOREIGN PATENT DOCUMENTS

| | | |
|---|---|---|
| CN | 102170906 | 8/2011 |
| EP | 0411306 A1 | 2/1991 |

(Continued)

OTHER PUBLICATIONS

Wang et al. "Inhibition of terminal complement components in presensitized transplant recipients prevents antibody-mediated rejection leading to long-term graft survival and accommodation" J. Immunol 2007; 179; 4451-4463.*
U.S. Appl. No. 13/128,523, filed Oct. 25, 2011, Russell P. Rother.
U.S. Appl. No. 15/148,491, filed May 6, 2016, Russell P. Rother.
U.S. Appl. No. 15/243,386, filed Aug. 22, 2016, Russell P. Rother.
U.S. Appl. No. 11/596,382, filed Jul. 16, 2008, Russell P. Rother.
U.S. Appl. No. 12/224,567, filed Oct. 19, 2009, Russell P. Rother.
U.S. Appl. No. 13/128,523, dated Aug. 8, 2016, J. Rogers.
U.S. Appl. No. 13/128,523, dated Jul. 28, 2016, J. Rogers.
U.S. Appl. No. 13/128,523, dated Apr. 29, 2016, J. Rogers.

(Continued)

*Primary Examiner* — Daniel E Kolker
*Assistant Examiner* — James Rogers
(74) *Attorney, Agent, or Firm* — J. Darrell Fontenot, Esq.; Jane E. Remillard, Esq.; Jill Gorny Sloper, Esq.

(57) ABSTRACT

The present disclosure relates to, inter alia, compositions containing an inhibitor of human complement and use of the compositions in methods for treating or preventing complement-associated disorders. In some embodiments, the inhibitor is chronically administered to patients. In some embodiments, the inhibitor is administered to a patient in an amount and with a frequency to maintain systemic complement inhibition and prevent breakthrough. In some embodiments, the compositions contain an antibody, or antigen-binding fragment thereof, that binds to a human complement component C5 protein or a fragment of the protein such as C5a or C5b.

4 Claims, No Drawings

(56) References Cited

U.S. PATENT DOCUMENTS

| | | |
|---|---|---|
| 2006/0153836 A1 | 7/2006 | Bailly et al. |
| 2006/0160726 A1 | 7/2006 | Fairlie et al. |
| 2007/0110757 A1 | 5/2007 | Wei et al. |
| 2007/0116710 A1 | 5/2007 | Bell et al. |
| 2008/0202513 A1 | 8/2008 | Birchall et al. |
| 2009/0028850 A1 | 1/2009 | Rother et al. |
| 2009/0041764 A1 | 2/2009 | Spuler et al. |
| 2009/0220508 A1* | 9/2009 | Bell .................. A61K 31/7105 424/135.1 |
| 2010/0034809 A1 | 2/2010 | Diefenbach-Streiber et al. |
| 2010/0120665 A1 | 5/2010 | Kaleko et al. |
| 2010/0135992 A1 | 6/2010 | Rother et al. |
| 2012/0022505 A1 | 1/2012 | Dacquay et al. |
| 2016/0319004 A1 | 11/2016 | Rother et al. |
| 2016/0355579 A1 | 12/2016 | Rother et al. |
| 2016/0355580 A1 | 12/2016 | Rother et al. |

FOREIGN PATENT DOCUMENTS

| | | | |
|---|---|---|---|
| WO | 91/15221 | A1 | 10/1991 |
| WO | 92/10205 | A1 | 6/1992 |
| WO | 2004/022096 | A1 | 3/2004 |
| WO | 2004/029207 | A2 | 4/2004 |
| WO | 2005074607 | A2 | 8/2005 |
| WO | 2005/110481 | A2 | 11/2005 |
| WO | 2007/038995 | A1 | 4/2007 |
| WO | 2007/066017 | A2 | 6/2007 |
| WO | 2007/103134 | A2 | 9/2007 |
| WO | 2008/106644 | A2 | 9/2008 |
| WO | 2008/153962 | A2 | 12/2008 |
| WO | 2010/015608 | A1 | 2/2010 |
| WO | 2010054403 | A1 | 5/2010 |

OTHER PUBLICATIONS

U.S. Appl. No. 13/128,523, dated Jan. 8, 2015, J. Rogers.
U.S. Appl. No. 13/128,523, dated Jul. 17, 2014, J. Rogers.
U.S. Appl. No. 13/128,523, dated Apr. 17, 2014, J. Rogers.
U.S. Appl. No. 11/596,382, dated Oct. 10, 2014, P. Huynh.
U.S. Appl. No. 11/596,382, dated Mar. 10, 2014, P. Huynh.
U.S. Appl. No. 11/596,382, dated May 4, 2011, P. Huynh.
U.S. Appl. No. 11/596,382, dated Sep. 29, 2010, P. Huynh.
U.S. Appl. No. 11/596,382, dated Aug. 3, 2010, P. Huynh.
U.S. Appl. No. 12/224,567, dated Oct. 3, 2013, P. Gambel.
U.S. Appl. No. 12/224,567, dated Oct. 24, 2012, P. Gambel.
U.S. Appl. No. 12/224,567, dated Mar. 29, 2012, P. Gambel.
U.S. Appl. No. 12/224,567, dated Dec. 22, 2011, P. Gambel.
Alexion Announces Presentation of Preliminary Results from Phase I Pilot Study of Eculizumab Treatment of Patients with Paroxysmal Nocturnal Hemoglobinuria; [online]; Alexion Pharmaceuticals: News; [Retrieved on Jun. 18, 2003]. Retrieved from theInternet: http://alexionpharmaceuticals.com/news/sub.sub.-press.cfm?prid=242&selec- tyear=2002.
Alexion Announces Results of Clinical Trial in Paroxysmal Nocturnal Hemoglobinuira Presented at the American Society of Hematology Annual Meeting; [online]; Alexion Pharmaceuticals, Inc.; [Retrieved on Jun. 17, 2003]; Retrieved from the Internet:http://www.noonanrusso.com/news/view.sub.--newsitem.aspx?ItemID=382.
Alexion Phamaceuticals: Complement Inhibitors; [online]; [Retrieved on Jun. 17, 2003]; Retrieved from the Internet: http://www.alexionpharm.com/techplat/complement.cfm.
Alexion Pharmaceuticals Signs Agreement with Lonza Biologics for Commercial Manufacturing; [online]; Alexion Pharmaceuitcals Inc.; [Retrieved on Jun. 17, 2003]; Retrieved from the Internet:http://www.noonanrusso.com/news/view.sub.--newsitem.aspx?ItemID=394.
Alexion Pharmaceuticals, "Study Evaluating Eculizumab (Soliris) in Preventing Antibody-Mediated Rejection (AMR) in Kidney Transplant Recipients Presented at the European Society for Organ Transplantation (ESOT) Annual Congress-Preliminary Data Show Potential for Effective Prophylaxis Against Early Acute AMR in Deceased-Donor Kidney Transplant Recipients Highly Sensitive to Their Donors," Presented at the European Society for Organ Transplantation (ESOT) Annual Congress , Sep. 10, 2013, 3 pages.
Alexion receives FDA, European approval for orphan drug status of new treatment for paroxysmal nocturnal hemoglobinuria, Transplant News, Jan. 15, 2004, XP002497241, //findarticles.com/p/articles/mi.sub.-mOYUG/is.sub.-1.sub.-14/ai.sub.-17208612 <http://findarticles.com/p/articles/mi.sub.--mOYUG/is.sub.-1-.sub.-14/ai.sub.-17208612>> [retrieved on Sep. 25, 2008].
Alexion Reports Presentation of Membranous Nephritis Clinical Trails; [online]; Alexion Pharmaceuticals: News; [Retrieved on Jun. 17, 2003]. Retrived from the Internet: http://www.alexionpharm.com/news/sub.sub.-press.cfm?prid=241&selectyear=- 2002.
Anonymous: "NCT01567085: An Open-Label, Single-Arm, Multicenter Trial to Determine Safety and Efficacy of Eculizumab in the Prevention of Antibody Mediated Rejection (AMR) in Sensitized Recipients of a Kidney Transplant From a Deceased Donor," Nov. 5, 2012, XP055293282,Retrieved from the Internet: URL:https://clinicaltrials.gov/archive/NCT01567085/2012 11 05[retrieved on— Aug. 3, 2016].
Araten, et al.,"High incidence of thrombosis in African-American and Latin-American patients with paroxysmal nocturnal haemoglobinuria," Thromb Haemost 2005; 93:88-91.
Audebert et al., "Cerebral ischemic infarction in paroxysmal nocturnal hemoglobinuria," J. Neurol 2005 252 1379-2565 (2005).
Brodsky, "New Insights into paroxysmal nocturnal hemoglobinuria," Hematology 516:24-28 (2006).
Chatelet, V. et al., "Safety and long-term efficacy of eculizumab in a renal; transplant patient with recurrent atypical hemolytic-uremic syndrome," American Journal of Transplantation, 2009, vol. 9 (11): 2644-2645, XP002739219.
Clague et al, "A low-hemolysis blood aspirator conserves blood during surgery," Biomed. Insrum. Technol., vol. 29 (5):419-424 (1995).
Clinics, Biotechnology News, vol. 24(30): 10 (2004).
Collard et al., "Endothelial nuclear factor-.kappa.B translocation and vascular cell adhesion molecule-1 induction by complement: inhibition with anti-human C5 therapy or cGMP analogues," Art. Thromb. Vas. 19:2623-2629 (1999).
Dodaro-Surrusco et al. "A patient guide: what to expect after a kidney transplant", pp. 1-76. (1995).
Eculizumab: 5G1.1, h5G1.1, Long-Acting Anti-C5 Monoclonal Antibody 5G1-1, Long-Acting Anti-C5 Monoclonal Antibody 5G1.1, Drugs in R&D 2007, LNKD-Pubmed: 17249850, vol. 8(1), pp. 61-68, XP009161624 (2007).
European Extended Search Report, EP 15152757.9-1412, dated May 20, 2015, pp. 1-12.
Extended European Search Report, EP15152758.7, dated May 20, 2015, pp. 1-10.
Figueroa and Densen, "Infectious Diseases Associated with Complement Deficiencies," Clinical Microbiology Reviews, vol. 4(3), pp. 359-395 (1991).
Fitch et al., "Pharmacology and biological efficacy of a recombinant, humanized, single-chain antibody C5 complement inhibitor in patients undergoing coronary artery bypass graft surgery with cardiopulmonary bypass," Circulation, 100 (25):2499-2506(1999).
Garba and Ubom, "Total serum lactate dehydrogenase activity in acute Plasmodium falciparum malaria infection," Singapore Medical J. 46(11):632-634 (2005).
Garcia et al., "Effect of Preservatives on IgG aggregation, Complement-activating Effect and Hypotensive Activity of Horse Polyvalent Antivenom Used in Snakebite Envenomation," Biologicals, vol. 30, pp. 143-151 (2002).
Genes and Disease; [online]; Paroxysmal nocturnal hemoglobinuria; [Retrieved on Jun. 17, 2003]. Retrieved from the Internet: http://www.ncbi.nlm.nih.gov/disease/PNH.html.
Glotz, D. et al., Eculizumab in Prevention of Acute Antibody-Mediated, Rejection in Sensitized Deceased-Donor Kidney Transplant Recipients: 1-Year Outcomes—ATC Abstracts, May 5, 2015:Retrieved from the Internet:<URL:http://www.atcmeetingabstracts.com/abs> tract/eculizumab-in-prevention-of-

(56) References Cited

OTHER PUBLICATIONS acute-antibody-mediated-rejection-in-sensitized-deceased-donor-kidney-transplant-recipients1-year-outcomes/[retrieved on Aug. 3, 2016].
Goicoechea, E. et al, "Activation is Required for Development of Atypical Haemolytic Uraemic Syndrome in CIH," Molecular Immunology, 2008, vol. 45, No. 16, Abstract 016, pp. 4100-4101.
Gruppo, R. et al., "Eculizumab for 1-18 Congenital Atypical Hemolytic-Uremic Syndrome," New England Journal of Medicine, 2009, vol. 360. No. 5, pp. 544-546, XP055186116.
Hall et al., "Primary prophylaxis with warfarin prevents thrombosis in paroxysmal nocturnal hemoglobinuria (PNH)," Blood 2003 102 3587-91.
Harding, J, "Eculizumab," Drugs of the Future, Prous Science, ES, vol. 29(7), pp. 673-676, XP008113000 (2004).
Hill et al., "Improvement in the symptoms of smooth muscle dystonia during eculizumab therapy in paroxysmal nocturnal hemoglobinuria," Haematology, 90(12): Abstract #ECR40 (2005).
Hill et al., "Sustained Control of Hemolysis and Symptoms and Reduced Transfusion Requirements over a Period of 2 Years in Paroxysmal Nocturnal Hemoglobinuria (PNH) with Eculizumab Therapy," Blood, 104:Abstract 2823 (2004) with ASH poster final2004.ppt.
Hill et al., "Sustained response and long-term safety of eculizumab in paroxysmal nocturnal hemoglobinuria," Blood 106:2559-2565 (2005).
Hill et al., "Protection of erythrocytes from human complement-mediated lysis by membrane-targeted recombinant soluble CD59: a new approach to PNH therapy," Blood 107(5):2131-2137 (2006).
Hill, Anita et al., Nitric oxide consumption and pulmonary hypertension in patients with paroxysmal nocturnal hemoglobinuria, Blood 106(11):Abstract 1046 (2005) XP002482085—47th Annual Meeting of the American Society of Hematology, Dec. 10-13, 2005.
Hill, "Eculizumab, for the treatment of paroxysmal nocturna; hemglobinuria," Clin. Adv. in Hemat. & Onc., XP0015384263 (11):849-850 (2005).
Hillmen et al. "Eculizumab, a C5 complement blocking antibody, is the first therapy to reduce transfusion requirements in patients with paroxysmal nocturnal haemoglobinuria (PNH); British Journal of Haematology," vol. 121, No. Supplement 1, p. 87,XP009144758 (2003). 43rd Annual Scientific Meeting of the British Society for Haematology, Apr. 7-9, 2003.
Hillmen et al., "Eculizumab, a C5 Complement-blocking Antibody, Abolishes Hemolysis and Renders Hemolytic Patients with Paroxysmal Nocturnal Hemoglobinuria (PNH) Transfusion Independent," 44th ASH Annual Meeting, Blood 100 (11) (Abstract No. 154)(2002).
Hillmen et al., "Eculizumab, a C5 complement-blocking antibody, controls haemolysis in paroxysmal nocturnal haemoglobinuria (PNH) with responses maintained over a prolonged period of therapy," British Journal of Haematology, vol. 125 (Suppl. 1):1-72, Abstract 5 (2004).
Hillmen et al., "Eculizumab, a C5 Complement-Blocking Antibody, Controls Hemolysis in Paroxysmal Nocturnal Hemoglobinuria (PNH) with Responses Maintained over prolonged Period of Therapy" Journal of the American Society of Hematology, vol. 102(11),Abstract 1858 (2003).
Hillmen et al., "Effect of eculizumab on hemolysis and transfusion requirements in patients with paroxysmal nocturnal hemoglobinuria," N Engl J Med 350 552-559 (2004).
Hillmen et al., "The complement inhibitor eculizumab in paroxysmal nocturnal hemoglobinuria," N Engl J Med 355 1233-1243 (2006).
Hillmen et al., "Effect of the complement inhibitor eculizumab on thromboembolism in patients with paroxysmal nocturnal hemoglobinuria," Blood 110(12):4123-4128 (2007).
Hillmen et al., "The terminal complement inhibitor eculizumab reduces thrombosis in patients with paroxysmal nocturnal hemoglobinuria," Blood 108(11):Abstract 123 (2006) XP002482084. 48th Annual Meeting of the American Society of Hematology. Dec. 9-12, 2006.
Inoue et al., "Molecular genetics of paroxysmal nocturnal hemoglobinuria," Int J Hematol. Feb. 2003;77(2):107-112.
Japanese Office Action, JP 2014-129867, dated May 28, 2015, pp. 1-13.
Jasinski et al., "A Novel mechanisms of complement-independent clearance of red cells deficient in glycosyl phosphatidylinositol-linked proteins," Blood, vol. 103(7), pp. 2827-2834 (2004).
Jungraithmayr, "Successful renal transplantation in a 10 year old boy with factor H associated atypical hemolytic uremic syndrome (aHUS) with plasmapheresis and eculizumab" vol. 13, Supp. 1, p. 109, 5th Congress of the International PediatiricTransplant Association, Abstract # LB17, Apr. 18, 2009.
Kallio et. al., "Blockade of complement inhibits obliterative bronchiolitis in rat tracheal allografts," American Journal of Respiratory and Critical Care Medicine, vol. 161(4 Pt 1), pp. 1332-1339, XP002356727 (2000).
Kaplan, M., "Eculizumab," Current Opinion in Investigational Drugs, vol. 3(7), pp. 1017-1023, XP009045356 (2002).
Kato et al., "Deconstructing sickle cell disease: reappraisal of the role of hemolysis in the development of clinical subphenotypes," Blood Reviews, vol. 21, pp. 37-47 (2007).
Kavanagh, D. et al., "Complement Regulatory Genes and Hemolytic Uremic Syndromes," Annual Review of Medicine, vol. 59. No. 1, 2008, pp. 293-309. XP055186136.
Kinoshita, Taroh, "Molecular pathogenesis of Paroxysmal Nocturnal Haemoglobinuria," XXVIth World Congress of the International Society of Haematology, Singapore, Aug. 25-29, 1996.
Lee et al., "Neisseria meningitidis Bacteremia in Association with Deficiency of the Sixth Component of Complement," Infection and Immunity, vol. 24(3): 656-660 (1979).
Loirat, C. et al., "Complement and the atypical hemolytic uremic syndrome in children," Pediatric Nephrology, Journal of the International Pediatric Nephrology Association, Springer, Berlin, DE, vol. 23. No. 11, 2008, pp. 1957-1972, XP019658955.
Luzzatto and Gianfaldoni, "Recent advances in biological and clinical aspects of paroxysmal nocturnal hemoglobinuria," Int. J. Hematol. 84:104-112 (2006).
Mache et al. "Complement inhibitor eculizumab in atypical hemolytic uremic syndrome" Clin J Am Soc Nephrol 4: 1312-1316, Aug. 2009).
Macneil, Eculizumab could be paroxysmal nocturnal hemoglobinuria breakthrough,; MacNeil, J.S.; 44th Annual Meeting of the American Society of Hematology, Medscape Medical News, (Dec. 13, 2002); [online]; Medscape from WebMD; [Retrieved on Jun. 17, 2003. Retrieved from the Internet: //www.medscape.com/viewarticle/446336 <http://www.medscape.com/viewarticle/446336>. XP009106338.
Marfo, K. et al., "Desensitization protocols and their outcome," Clinical Journal of the American Society of Nephrology, vol. 6(4), 922-936 (2011).
Merck Manuar of Diagnosis and Therapy (The), Seventeenth Edition, Chapter 127 Anemias, pp. 849-883 (1999).
Meyers and Parker, "Management Issues in Paroxysmal Nocturnal Hemoglobinuria," International Journal of Hematology, 77:125-132 (2003).
Morath, C., et al., "Prevention of antibody-mediated kidney transplant rejection," Transplant International, vol. 25 (6):633-645 (2012).
Morgan and Harris, "Complement therapeutics; history and current progress," Molecular Immunology, vol. 40(2-4), pp. 159-170, XP002687981 (2003).
Mortazavi et al., "The spectrum of PIG—A gene mutations in aplastic anemia/paroxysmal nocturnal hemoglobinuria (AA/PNH): a high incidence of multiple mutations and evidence of a mutational hot spot," Blood 101 2833-2841 (2003).
Moyo et al., "Natural history of paroxysmal nocturnal haemoglobinuria using modern diagnostic assays," British J Haematology 126, 133-138 (2004).

(56) References Cited

OTHER PUBLICATIONS

Nangaku, M. et al., "CD59 Protects Glomerular Endothelial Cells from Immune-Mediated Thrombotic Microangiopathy in Rats," Journal of the American Society of Nephrology, vol. 9(4), pp. 590-597 (1998).
Notice of Opposition for EP Patent No. 1720571, dated Mar. 18, 2013.
Nurnberger, Jens et al., "Eculizumab for Atypical Hemolytic-Uremic Syndrome," New England Journal of Medicine, vol. 360, No. 5, 2009, pp. 542-544, XP055045531.
Parker et al., "Diagnosis and management of paroxysmal nocturnal hemoglobinuria," Blood 106(12):3699-3709 (2005).
Paroxysmal nocturnal hemoglobinuria, included; PNH, included phosphatidylinositol glycan, class A, pseudogene 1, included; pigap1, included piga-related processed gene, included [online]. OMIM-Online Medelian Inheritance in Man; John HopkinsUniversity; [Retrieved on Jun. 18, 2003]. Retrieved from the Internet: http://www.ncbi.nlm.nih.gov/entrez/query.fcgi?cmd=Retrieve&db=OMIM&dopt=d- etailed . . . .
Pratt, J.R. et al., "Effects of Complement Inhibition with Soluble Complement Receptor 1 on Vascular Injury and Inflammation during Renal Allograft Rejection in the Rat," American Journal of Pathology, vol. 149(6), pp. 2055-2066 (1996).
Reiter et al., "Cell-free hemoglobin limits nitric oxide bioavailability in sickle-cell disease," Nature Medicine 8 (12):1383-1389 (2002).
Richards et al., "Evolution of GPI-Deficient Clones Predicts Clinical Course in Paroxysmal Nocturnal Haemoglobinuria," Blood, 104:Abstract 172 (2004).
Rodary et al., "Patient preference for either the EORTC QLQ-C30 or the FACIT Quality of Life (QOL) measures: a study performed in patient suffering from carcinoma of an unknown primary site (CUP)," European Journal of Cancer, vol. 40, pp. 521-528(2004).
Rosse et al., Immune-mediated hemolytic anemia, Hematology Am Soc Hematol Educ Program, 48-62 (2004) XP002497825.
Rosse, W.F. "A new way to prevent thrombosis?," Blood,vol. 110, No. 12, Dec. 1, 2007, p. 3821-3821, XP055187205.
Rother et al., "Eculizumab, a C5 complement-blocking antibody, abolishes hemolysis and reduces transfusion dependency in patients with paroxysmal nocturnal hemoglobinuria (PNH)," Molecular Immunology, vol. 40(2-4), p. 197; XP009163498, (2003).
Rother et al., "The clinical sequelae of intravascular hemolysis and extracellular plasma hemoglobin," JAMA 293 (13):1653-1662 (2005).
Rother R., et al., "Discovery and development of the complement inhibitor eculizumab for the treatment of paroxysmal nocturnal hemoglobinuria", Nature Biotechnology, vol. 25, No. 11, Dec. 12, 2007, pp. 1256-1264, P002553743.
Shin, J. et al., "More on Eculizumab for Congenital Atypical Hemolytic-Uremic Syndrome," New England Journal of Medicine, vol. 360, 2009, pp. 2142-2143, XP055186122.
Stebler et al., "High-dose recombinant human erythropoietin for treatment of anemia in myelodysplastic syndromes and paroxysmal nocturnal hemoglobinuria: a pilot study," Exp. Hematol. 18:1204-1208 (1990).
Stegall, M. et al., "The role of complement in antibody-mediated rejection in kidney transplantation," Nature Reviews, Nephrology, vol. 8 (11):670-678 (2012).
Stegall, M.D., et al., "Terminal Complement Inhibition Decreases Antibody-Mediated Rejection in Sensitized Renal Transplant Recipients," Am. J. Transplantation, vol. 98(10): 2405-2413 (2011).
Strauss et al., "Alternative pathway of complement in sickle cell disease," Pediat. Res. vol. 11, pp. 285-289 (1977).
Stuart et al., "Sickle-cell disease," Lancet, vol. 364, pp. 1343-1360 (2004).
Taheri et al. "Recurrence of hemolytic-uremic syndrome following live related renal transplantation" Arch Iran Med 9(2), 2006, pp. 170-172.
Tait, B. et al., "Consensus Guidelines on the Testing and Clinical Management Issues Associated With HLA and Non-HLA Antibodies in Transplantation," Transplantation, vol. 95(1):19-47 (2013).
Tang and Pikal, Design of Freeze-Drying Processes for Pharmaceuticals: Practical Advice, Pharmaceutical Research, vol. 21(2), pp. 191-200 (2004).
Thomas et. al., "Inhibition of complement activity by humanized anti-C5 antibody and single-chain Fv," Molecular Immunology, vol. 33(17-18), pp. 1389-1401, XP002262113 (1996).
Vakeva, et al., "Myocardial infarction and apoptosis after myocardial ischemia and reperfusion," Circulation 97:2259-2267 (1998).
Wuzner, R. et al, "Therapeutic strategies for atypical and recurrent hemolytic uremic syndromes (HUS)," Complement and Kidney Disease, 2006, pp. 149-163, XP009161632.
Alexion Press Release, Dec. 7, 2008, "First Clinical Experience with Solids® in Treating Patients with Two Rare Complement-Mediated Diseases Presented at ASH Annual Meeting" 2 pages.
Bell, L. et al. "Clinics," Biotechnology News, vol. 24(30): 10 (2004).
Committee for Medicinal Products for Human USE (CHMP), "Assessment Report, Solids," European Medicines Agency, Sep. 22, 2011, 115 pages.
Keating, G. et al., "Eculizumab: A Review of Its Use in Atypical Haemolytic Uraemic Syndrome," Drugs, vol. 73: 2053-2066 (2013).
Kelly, R. et al. "Modification of the Eculizumab Dose to Successfully Manage Intravascular Breakthrough Hemolysis in Patients with Paroxysmal Nocturnal Hemoglobinuria," Blood, vol. 112(11)(3441):6 pages (2008) [online] [retrieved on: Nov. 18, 2016], Internet <URL:http://www.bloodjournal.org/content/112/11/3441.
Kelly, R. J., et al., "Modification of the Standard Eculizumab Dose to Successfully Manage Intravascular Haemolysis Break through in Patients with Paroxysmal Nocturnal Haemoglobinuria," Haematologica, (Jun. 2009) 94(Suppl. S2):.239-240, Abstract No. 0587.
Ricklin, D. et al., "Complement-targeted therapeutics," Nature Biotechnology, vol. 25(11):1265-1275 (2007).
Socie, G. et al. "Sustained Improvements in Transfusion Requirements, Fatigue and Thrombosis with Eculizumab Treatment in Paroxysmal Nocturnal Hemoglobinuria," Blood, 110 (3672) 5 pages (2007); [online] [retrieval date: Nov. 30, 2016], Internet URL:http://www.bloodjournal.org/content/110/11/3672?sso-checked=true>.
Takada, Asada, "Yakubutsudoryokugaku Gaisetsu—Yoriyoki Yakubutsuchiryou no tameni-" Essential of Pharmacokinetics,[Outline of pharmacokinetics—For better drug therapy-] (2nd print published on Feb. 25, 1979) Hirokawa-Shoten Ltd. p. 73.

\* cited by examiner

SEQUENCE LISTING

<160> NUMBER OF SEQ ID NOS: 26

<210> SEQ ID NO 1
<211> LENGTH: 1676

<212> TYPE: PRT
<213> ORGANISM: Homo sapiens

<400> SEQUENCE: 1

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380

Gly Val Pro Val Ile Leu Asn Ala Gln Thr Ile Asp Val Asn Gln Glu
385                 390                 395                 400
```

-continued

```
Thr Ser Asp Leu Asp Pro Ser Lys Ser Val Thr Arg Val Asp Asp Gly
            405                 410                 415
Val Ala Ser Phe Val Leu Asn Leu Pro Ser Gly Val Thr Val Leu Glu
            420                 425                 430
Phe Asn Val Lys Thr Asp Ala Pro Asp Leu Pro Glu Glu Asn Gln Ala
            435                 440                 445
Arg Glu Gly Tyr Arg Ala Ile Ala Tyr Ser Ser Leu Ser Gln Ser Tyr
450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
            485                 490                 495
Thr His Tyr Asn Tyr Leu Ile Leu Ser Lys Gly Lys Ile Ile His Phe
            500                 505                 510
Gly Thr Arg Glu Lys Phe Ser Asp Ala Ser Tyr Gln Ser Ile Asn Ile
            515                 520                 525
Pro Val Thr Gln Asn Met Val Pro Ser Ser Arg Leu Leu Val Tyr Tyr
            530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
            565                 570                 575
Pro Asp Ala Asp Ala Tyr Ser Pro Gly Gln Thr Val Ser Leu Asn Met
            580                 585                 590
Ala Thr Gly Met Asp Ser Trp Val Ala Leu Ala Ala Val Asp Ser Ala
            595                 600                 605
Val Tyr Gly Val Gln Arg Gly Ala Lys Lys Pro Leu Glu Arg Val Phe
610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
            645                 650                 655
Ala Asn Ala Asp Asp Ser Gln Glu Asn Asp Glu Pro Cys Lys Glu Ile
            660                 665                 670
Leu Arg Pro Arg Arg Thr Leu Gln Lys Lys Ile Glu Glu Ile Ala Ala
            675                 680                 685
Lys Tyr Lys His Ser Val Val Lys Cys Cys Tyr Asp Gly Ala Cys
690                 695                 700
Val Asn Asn Asp Glu Thr Cys Glu Gln Arg Ala Ala Arg Ile Ser Leu
705                 710                 715                 720
Gly Pro Arg Cys Ile Lys Ala Phe Thr Glu Cys Cys Val Val Ala Ser
            725                 730                 735
Gln Leu Arg Ala Asn Ile Ser His Lys Asp Met Gln Leu Gly Arg Leu
            740                 745                 750
His Met Lys Thr Leu Leu Pro Val Ser Lys Pro Glu Ile Arg Ser Tyr
            755                 760                 765
Phe Pro Glu Ser Trp Leu Trp Glu Val His Leu Val Pro Arg Arg Lys
            770                 775                 780
Gln Leu Gln Phe Ala Leu Pro Asp Ser Leu Thr Thr Trp Glu Ile Gln
785                 790                 795                 800
Gly Ile Gly Ile Ser Asn Thr Gly Ile Cys Val Ala Asp Thr Val Lys
            805                 810                 815
```

```
Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
            850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
                915                 920                 925

Val Val Pro Glu Gly Val Lys Arg Glu Ser Tyr Ser Gly Val Thr Leu
            930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
                980                 985                 990

Ser Gln Glu Gly Ile Asn Ile Leu  Thr His Leu Pro Lys  Gly Ser Ala
            995                 1000                1005

Glu Ala Glu Leu Met Ser Val  Pro Val Phe Tyr  Val Phe His
    1010                1015                1020

Tyr Leu Glu Thr Gly Asn His  Trp Asn Ile Phe His  Ser Asp Pro
    1025                1030                1035

Leu Ile Glu Lys Gln Lys Leu  Lys Lys Lys Leu Lys  Glu Gly Met
    1040                1045                1050

Leu Ser Ile Met Ser Tyr Arg  Asn Ala Asp Tyr Ser  Tyr Ser Val
    1055                1060                1065

Trp Lys Gly Gly Ser Ala Ser  Thr Trp Leu Thr Ala  Phe Ala Leu
    1070                1075                1080

Arg Val Leu Gly Gln Val Asn  Lys Tyr Val Glu Gln  Asn Gln Asn
    1085                1090                1095

Ser Ile Cys Asn Ser Leu Leu  Trp Leu Val Glu Asn  Tyr Gln Leu
    1100                1105                1110

Asp Asn Gly Ser Phe Lys Glu  Asn Ser Gln Tyr Gln  Pro Ile Lys
    1115                1120                1125

Leu Gln Gly Thr Leu Pro Val  Glu Ala Arg Glu Asn  Ser Leu Tyr
    1130                1135                1140

Leu Thr Ala Phe Thr Val Ile  Gly Ile Arg Lys Ala  Phe Asp Ile
    1145                1150                1155

Cys Pro Leu Val Lys Ile Asp  Thr Ala Leu Ile Lys  Ala Asp Asn
    1160                1165                1170

Phe Leu Leu Glu Asn Thr Leu  Pro Ala Gln Ser Thr  Phe Thr Leu
    1175                1180                1185

Ala Ile Ser Ala Tyr Ala Leu  Ser Leu Gly Asp Lys  Thr His Pro
    1190                1195                1200

Gln Phe Arg Ser Ile Val Ser  Ala Leu Lys Arg Glu  Ala Leu Val
    1205                1210                1215

Lys Gly Asn Pro Pro Ile Tyr  Arg Phe Trp Lys Asp  Asn Leu Gln
```

-continued

|  | 1220 |  |  |  | 1225 |  |  |  | 1230 |  |
|---|---|---|---|---|---|---|---|---|---|---|

His Lys Asp Ser Ser Val Pro Asn Thr Gly Thr Ala Arg Met Val
    1235                      1240                    1245

Glu Thr Thr Ala Tyr Ala Leu Leu Thr Ser Leu Asn Leu Lys Asp
    1250                      1255                    1260

Ile Asn Tyr Val Asn Pro Val Ile Lys Trp Leu Ser Glu Glu Gln
    1265                      1270                    1275

Arg Tyr Gly Gly Gly Phe Tyr Ser Thr Gln Asp Thr Ile Asn Ala
    1280                      1285                    1290

Ile Glu Gly Leu Thr Glu Tyr Ser Leu Leu Val Lys Gln Leu Arg
    1295                      1300                    1305

Leu Ser Met Asp Ile Asp Val Ser Tyr Lys His Lys Gly Ala Leu
    1310                      1315                    1320

His Asn Tyr Lys Met Thr Asp Lys Asn Phe Leu Gly Arg Pro Val
    1325                      1330                    1335

Glu Val Leu Leu Asn Asp Asp Leu Ile Val Ser Thr Gly Phe Gly
    1340                      1345                    1350

Ser Gly Leu Ala Thr Val His Val Thr Thr Val His Lys Thr
    1355                      1360                    1365

Ser Thr Ser Glu Glu Val Cys Ser Phe Tyr Leu Lys Ile Asp Thr
    1370                      1375                    1380

Gln Asp Ile Glu Ala Ser His Tyr Arg Gly Tyr Gly Asn Ser Asp
    1385                      1390                    1395

Tyr Lys Arg Ile Val Ala Cys Ala Ser Tyr Lys Pro Ser Arg Glu
    1400                      1405                    1410

Glu Ser Ser Ser Gly Ser Ser His Ala Val Met Asp Ile Ser Leu
    1415                      1420                    1425

Pro Thr Gly Ile Ser Ala Asn Glu Glu Asp Leu Lys Ala Leu Val
    1430                      1435                    1440

Glu Gly Val Asp Gln Leu Phe Thr Asp Tyr Gln Ile Lys Asp Gly
    1445                      1450                    1455

His Val Ile Leu Gln Leu Asn Ser Ile Pro Ser Ser Asp Phe Leu
    1460                      1465                    1470

Cys Val Arg Phe Arg Ile Phe Glu Leu Phe Glu Val Gly Phe Leu
    1475                      1480                    1485

Ser Pro Ala Thr Phe Thr Val Tyr Glu Tyr His Arg Pro Asp Lys
    1490                      1495                    1500

Gln Cys Thr Met Phe Tyr Ser Thr Ser Asn Ile Lys Ile Gln Lys
    1505                      1510                    1515

Val Cys Glu Gly Ala Ala Cys Lys Cys Val Glu Ala Asp Cys Gly
    1520                      1525                    1530

Gln Met Gln Glu Glu Leu Asp Leu Thr Ile Ser Ala Glu Thr Arg
    1535                      1540                    1545

Lys Gln Thr Ala Cys Lys Pro Glu Ile Ala Tyr Ala Tyr Lys Val
    1550                      1555                    1560

Ser Ile Thr Ser Ile Thr Val Glu Asn Val Phe Val Lys Tyr Lys
    1565                      1570                    1575

Ala Thr Leu Leu Asp Ile Tyr Lys Thr Gly Glu Ala Val Ala Glu
    1580                      1585                    1590

Lys Asp Ser Glu Ile Thr Phe Ile Lys Lys Val Thr Cys Thr Asn
    1595                      1600                    1605

Ala Glu Leu Val Lys Gly Arg Gln Tyr Leu Ile Met Gly Lys Glu
    1610                      1615                    1620

```
Ala Leu Gln Ile Lys Tyr Asn Phe Ser Phe Arg Tyr Ile Tyr Pro
         1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 2
<211> LENGTH: 1658
<212> TYPE: PRT
<213> ORGANISM: Homo sapiens

<400> SEQUENCE: 2

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30

Asp Ala Thr Ile Ser Ile Lys Ser Tyr Pro Asp Lys Lys Phe Ser Tyr
        35                  40                  45

Ser Ser Gly His Val His Leu Ser Ser Glu Asn Lys Phe Gln Asn Ser
    50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser
                85                  90                  95

Lys Arg Met Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
        115                 120                 125

Ser Leu Asn Asp Asp Leu Lys Pro Ala Lys Arg Glu Thr Val Leu Thr
    130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
            180                 185                 190

Thr Thr Gly Thr Ala Tyr Phe Glu Val Lys Glu Tyr Val Leu Pro His
        195                 200                 205

Phe Ser Val Ser Ile Glu Pro Glu Tyr Asn Phe Ile Gly Tyr Lys Asn
    210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
            260                 265                 270

Met Leu Ile Asn Gly Ile Ala Gln Val Thr Phe Asp Ser Glu Thr Ala
        275                 280                 285

Val Lys Glu Leu Ser Tyr Tyr Ser Leu Glu Asp Leu Asn Asn Lys Tyr
    290                 295                 300

Leu Tyr Ile Ala Val Thr Val Ile Glu Ser Thr Gly Gly Phe Ser Glu
```

```
                305                 310                 315                 320
            Glu Ala Glu Ile Pro Gly Ile Lys Tyr Val Leu Ser Pro Tyr Lys Leu
                        325                 330                 335
            Asn Leu Val Ala Thr Pro Leu Phe Leu Lys Pro Gly Ile Pro Tyr Pro
                        340                 345                 350
            Ile Lys Val Gln Val Lys Asp Ser Leu Asp Gln Leu Val Gly Gly Val
                        355                 360                 365
            Pro Val Ile Leu Asn Ala Gln Thr Ile Asp Val Asn Gln Glu Thr Ser
                370                 375                 380
            Asp Leu Asp Pro Ser Lys Ser Val Thr Arg Val Asp Asp Gly Val Ala
            385                 390                 395                 400
            Ser Phe Val Leu Asn Leu Pro Ser Gly Val Thr Val Leu Glu Phe Asn
                        405                 410                 415
            Val Lys Thr Asp Ala Pro Asp Leu Pro Glu Glu Asn Gln Ala Arg Glu
                        420                 425                 430
            Gly Tyr Arg Ala Ile Ala Tyr Ser Ser Leu Ser Gln Ser Tyr Leu Tyr
                        435                 440                 445
            Ile Asp Trp Thr Asp Asn His Lys Ala Leu Leu Val Gly Glu His Leu
                450                 455                 460
            Asn Ile Ile Val Thr Pro Lys Ser Pro Tyr Ile Asp Lys Ile Thr His
            465                 470                 475                 480
            Tyr Asn Tyr Leu Ile Leu Ser Lys Gly Lys Ile Ile His Phe Gly Thr
                        485                 490                 495
            Arg Glu Lys Phe Ser Asp Ala Ser Tyr Gln Ser Ile Asn Ile Pro Val
                        500                 505                 510
            Thr Gln Asn Met Val Pro Ser Ser Arg Leu Leu Val Tyr Tyr Ile Val
                        515                 520                 525
            Thr Gly Glu Gln Thr Ala Glu Leu Val Ser Asp Ser Val Trp Leu Asn
                        530                 535                 540
            Ile Glu Glu Lys Cys Gly Asn Gln Leu Gln Val His Leu Ser Pro Asp
            545                 550                 555                 560
            Ala Asp Ala Tyr Ser Pro Gly Gln Thr Val Ser Leu Asn Met Ala Thr
                        565                 570                 575
            Gly Met Asp Ser Trp Val Ala Leu Ala Ala Val Asp Ser Ala Val Tyr
                        580                 585                 590
            Gly Val Gln Arg Gly Ala Lys Lys Pro Leu Glu Arg Val Phe Gln Phe
                        595                 600                 605
            Leu Glu Lys Ser Asp Leu Gly Cys Gly Ala Gly Gly Gly Leu Asn Asn
                        610                 615                 620
            Ala Asn Val Phe His Leu Ala Gly Leu Thr Phe Leu Thr Asn Ala Asn
            625                 630                 635                 640
            Ala Asp Asp Ser Gln Glu Asn Asp Glu Pro Cys Lys Glu Ile Leu Arg
                        645                 650                 655
            Pro Arg Arg Thr Leu Gln Lys Lys Ile Glu Glu Ile Ala Ala Lys Tyr
                        660                 665                 670
            Lys His Ser Val Val Lys Lys Cys Cys Tyr Asp Gly Ala Cys Val Asn
                        675                 680                 685
            Asn Asp Glu Thr Cys Glu Gln Arg Ala Ala Arg Ile Ser Leu Gly Pro
                        690                 695                 700
            Arg Cys Ile Lys Ala Phe Thr Glu Cys Cys Val Val Ala Ser Gln Leu
            705                 710                 715                 720
            Arg Ala Asn Ile Ser His Lys Asp Met Gln Leu Gly Arg Leu His Met
                        725                 730                 735
```

-continued

Lys Thr Leu Leu Pro Val Ser Lys Pro Glu Ile Arg Ser Tyr Phe Pro
            740                 745                 750

Glu Ser Trp Leu Trp Glu Val His Leu Val Pro Arg Lys Gln Leu
        755                 760                 765

Gln Phe Ala Leu Pro Asp Ser Leu Thr Thr Trp Glu Ile Gln Gly Ile
770                 775                 780

Gly Ile Ser Asn Thr Gly Ile Cys Val Ala Asp Thr Val Lys Ala Lys
785                 790                 795                 800

Val Phe Lys Asp Val Phe Leu Glu Met Asn Ile Pro Tyr Ser Val Val
            805                 810                 815

Arg Gly Glu Gln Ile Gln Leu Lys Gly Thr Val Tyr Asn Tyr Arg Thr
            820                 825                 830

Ser Gly Met Gln Phe Cys Val Lys Met Ser Ala Val Glu Gly Ile Cys
            835                 840                 845

Thr Ser Glu Ser Pro Val Ile Asp His Gln Gly Thr Lys Ser Ser Lys
850                 855                 860

Cys Val Arg Gln Lys Val Glu Gly Ser Ser His Leu Val Thr Phe
865                 870                 875                 880

Thr Val Leu Pro Leu Glu Ile Gly Leu His Asn Ile Asn Phe Ser Leu
            885                 890                 895

Glu Thr Trp Phe Gly Lys Glu Ile Leu Val Lys Thr Leu Arg Val Val
        900                 905                 910

Pro Glu Gly Val Lys Arg Glu Ser Tyr Ser Gly Val Thr Leu Asp Pro
        915                 920                 925

Arg Gly Ile Tyr Gly Thr Ile Ser Arg Arg Lys Glu Phe Pro Tyr Arg
        930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Gln
            965                 970                 975

Glu Gly Ile Asn Ile Leu Thr His Leu Pro Lys Gly Ser Ala Glu Ala
            980                 985                 990

Glu Leu Met Ser Val Val Pro Val Phe Tyr Val Phe His Tyr Leu Glu
        995                 1000                1005

Thr Gly Asn His Trp Asn Ile Phe His Ser Asp Pro Leu Ile Glu
    1010                1015                1020

Lys Gln Lys Leu Lys Lys Lys Leu Lys Glu Gly Met Leu Ser Ile
    1025                1030                1035

Met Ser Tyr Arg Asn Ala Asp Tyr Ser Tyr Ser Val Trp Lys Gly
    1040                1045                1050

Gly Ser Ala Ser Thr Trp Leu Thr Ala Phe Ala Leu Arg Val Leu
    1055                1060                1065

Gly Gln Val Asn Lys Tyr Val Glu Gln Asn Gln Asn Ser Ile Cys
    1070                1075                1080

Asn Ser Leu Leu Trp Leu Val Glu Asn Tyr Gln Leu Asp Asn Gly
    1085                1090                1095

Ser Phe Lys Glu Asn Ser Gln Tyr Gln Pro Ile Lys Leu Gln Gly
    1100                1105                1110

Thr Leu Pro Val Glu Ala Arg Glu Asn Ser Leu Tyr Leu Thr Ala
    1115                1120                1125

Phe Thr Val Ile Gly Ile Arg Lys Ala Phe Asp Ile Cys Pro Leu
    1130                1135                1140

-continued

Val Lys Ile Asp Thr Ala Leu Ile Lys Ala Asp Asn Phe Leu Leu
1145             1150             1155

Glu Asn Thr Leu Pro Ala Gln Ser Thr Phe Thr Leu Ala Ile Ser
1160             1165             1170

Ala Tyr Ala Leu Ser Leu Gly Asp Lys Thr His Pro Gln Phe Arg
1175             1180             1185

Ser Ile Val Ser Ala Leu Lys Arg Glu Ala Leu Val Lys Gly Asn
1190             1195             1200

Pro Pro Ile Tyr Arg Phe Trp Lys Asp Asn Leu Gln His Lys Asp
1205             1210             1215

Ser Ser Val Pro Asn Thr Gly Thr Ala Arg Met Val Glu Thr Thr
1220             1225             1230

Ala Tyr Ala Leu Leu Thr Ser Leu Asn Leu Lys Asp Ile Asn Tyr
1235             1240             1245

Val Asn Pro Val Ile Lys Trp Leu Ser Glu Glu Gln Arg Tyr Gly
1250             1255             1260

Gly Gly Phe Tyr Ser Thr Gln Asp Thr Ile Asn Ala Ile Glu Gly
1265             1270             1275

Leu Thr Glu Tyr Ser Leu Leu Val Lys Gln Leu Arg Leu Ser Met
1280             1285             1290

Asp Ile Asp Val Ser Tyr Lys His Lys Gly Ala Leu His Asn Tyr
1295             1300             1305

Lys Met Thr Asp Lys Asn Phe Leu Gly Arg Pro Val Glu Val Leu
1310             1315             1320

Leu Asn Asp Asp Leu Ile Val Ser Thr Gly Phe Gly Ser Gly Leu
1325             1330             1335

Ala Thr Val His Val Thr Thr Val Val His Lys Thr Ser Thr Ser
1340             1345             1350

Glu Glu Val Cys Ser Phe Tyr Leu Lys Ile Asp Thr Gln Asp Ile
1355             1360             1365

Glu Ala Ser His Tyr Arg Gly Tyr Gly Asn Ser Asp Tyr Lys Arg
1370             1375             1380

Ile Val Ala Cys Ala Ser Tyr Lys Pro Ser Arg Glu Glu Ser Ser
1385             1390             1395

Ser Gly Ser Ser His Ala Val Met Asp Ile Ser Leu Pro Thr Gly
1400             1405             1410

Ile Ser Ala Asn Glu Glu Asp Leu Lys Ala Leu Val Glu Gly Val
1415             1420             1425

Asp Gln Leu Phe Thr Asp Tyr Gln Ile Lys Asp Gly His Val Ile
1430             1435             1440

Leu Gln Leu Asn Ser Ile Pro Ser Ser Asp Phe Leu Cys Val Arg
1445             1450             1455

Phe Arg Ile Phe Glu Leu Phe Glu Val Gly Phe Leu Ser Pro Ala
1460             1465             1470

Thr Phe Thr Val Tyr Glu Tyr His Arg Pro Asp Lys Gln Cys Thr
1475             1480             1485

Met Phe Tyr Ser Thr Ser Asn Ile Lys Ile Gln Lys Val Cys Glu
1490             1495             1500

Gly Ala Ala Cys Lys Cys Val Glu Ala Asp Cys Gly Gln Met Gln
1505             1510             1515

Glu Glu Leu Asp Leu Thr Ile Ser Ala Glu Thr Arg Lys Gln Thr
1520             1525             1530

Ala Cys Lys Pro Glu Ile Ala Tyr Ala Tyr Lys Val Ser Ile Thr

-continued

```
                1535                1540                1545

Ser Ile Thr Val Glu Asn Val Phe Val Lys Tyr Lys Ala Thr Leu
    1550                1555                1560

Leu Asp Ile Tyr Lys Thr Gly Glu Ala Val Ala Glu Lys Asp Ser
1565                1570                1575

Glu Ile Thr Phe Ile Lys Lys Val Thr Cys Thr Asn Ala Glu Leu
    1580                1585                1590

Val Lys Gly Arg Gln Tyr Leu Ile Met Gly Lys Glu Ala Leu Gln
1595                1600                1605

Ile Lys Tyr Asn Phe Ser Phe Arg Tyr Ile Tyr Pro Leu Asp Ser
    1610                1615                1620

Leu Thr Trp Ile Glu Tyr Trp Pro Arg Asp Thr Thr Cys Ser Ser
1625                1630                1635

Cys Gln Ala Phe Leu Ala Asn Leu Asp Glu Phe Ala Glu Asp Ile
    1640                1645                1650

Phe Leu Asn Gly Cys
1655

<210> SEQ ID NO 3
<211> LENGTH: 999
<212> TYPE: PRT
<213> ORGANISM: Homo sapiens

<400> SEQUENCE: 3

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg Leu His Met Lys Thr Leu
65                  70                  75                  80

Leu Pro Val Ser Lys Pro Glu Ile Arg Ser Tyr Phe Pro Glu Ser Trp
                85                  90                  95

Leu Trp Glu Val His Leu Val Pro Arg Arg Lys Gln Leu Gln Phe Ala
            100                 105                 110

Leu Pro Asp Ser Leu Thr Thr Trp Glu Ile Gln Gly Ile Gly Ile Ser
        115                 120                 125

Asn Thr Gly Ile Cys Val Ala Asp Thr Val Lys Ala Lys Val Phe Lys
    130                 135                 140

Asp Val Phe Leu Glu Met Asn Ile Pro Tyr Ser Val Val Arg Gly Glu
145                 150                 155                 160

Gln Ile Gln Leu Lys Gly Thr Val Tyr Asn Tyr Arg Thr Ser Gly Met
                165                 170                 175

Gln Phe Cys Val Lys Met Ser Ala Val Glu Gly Ile Cys Thr Ser Glu
            180                 185                 190

Ser Pro Val Ile Asp His Gln Gly Thr Lys Ser Ser Lys Cys Val Arg
        195                 200                 205

Gln Lys Val Glu Gly Ser Ser Ser His Leu Val Thr Phe Thr Val Leu
    210                 215                 220

Pro Leu Glu Ile Gly Leu His Asn Ile Asn Phe Ser Leu Glu Thr Trp
225                 230                 235                 240
```

```
Phe Gly Lys Glu Ile Leu Val Lys Thr Leu Arg Val Pro Glu Gly
                245                 250                 255

Val Lys Arg Glu Ser Tyr Ser Gly Val Thr Leu Asp Pro Arg Gly Ile
            260                 265                 270

Tyr Gly Thr Ile Ser Arg Arg Lys Glu Phe Pro Tyr Arg Ile Pro Leu
            275                 280                 285

Asp Leu Val Pro Lys Thr Glu Ile Lys Arg Ile Leu Ser Val Lys Gly
            290                 295                 300

Leu Leu Val Gly Glu Ile Leu Ser Ala Val Leu Ser Gln Glu Gly Ile
305                 310                 315                 320

Asn Ile Leu Thr His Leu Pro Lys Gly Ser Ala Glu Ala Glu Leu Met
                325                 330                 335

Ser Val Val Pro Val Phe Tyr Val Phe His Tyr Leu Glu Thr Gly Asn
            340                 345                 350

His Trp Asn Ile Phe His Ser Asp Pro Leu Ile Glu Lys Gln Lys Leu
            355                 360                 365

Lys Lys Lys Leu Lys Glu Gly Met Leu Ser Ile Met Ser Tyr Arg Asn
            370                 375                 380

Ala Asp Tyr Ser Tyr Ser Val Trp Lys Gly Gly Ser Ala Ser Thr Trp
385                 390                 395                 400

Leu Thr Ala Phe Ala Leu Arg Val Leu Gly Gln Val Asn Lys Tyr Val
                405                 410                 415

Glu Gln Asn Gln Asn Ser Ile Cys Asn Ser Leu Leu Trp Leu Val Glu
            420                 425                 430

Asn Tyr Gln Leu Asp Asn Gly Ser Phe Lys Glu Asn Ser Gln Tyr Gln
            435                 440                 445

Pro Ile Lys Leu Gln Gly Thr Leu Pro Val Glu Ala Arg Glu Asn Ser
450                 455                 460

Leu Tyr Leu Thr Ala Phe Thr Val Ile Gly Ile Arg Lys Ala Phe Asp
465                 470                 475                 480

Ile Cys Pro Leu Val Lys Ile Asp Thr Ala Leu Ile Lys Ala Asp Asn
                485                 490                 495

Phe Leu Leu Glu Asn Thr Leu Pro Ala Gln Ser Thr Phe Thr Leu Ala
            500                 505                 510

Ile Ser Ala Tyr Ala Leu Ser Leu Gly Asp Lys Thr His Pro Gln Phe
            515                 520                 525

Arg Ser Ile Val Ser Ala Leu Lys Arg Glu Ala Leu Val Lys Gly Asn
            530                 535                 540

Pro Pro Ile Tyr Arg Phe Trp Lys Asp Asn Leu Gln His Lys Asp Ser
545                 550                 555                 560

Ser Val Pro Asn Thr Gly Thr Ala Arg Met Val Glu Thr Thr Ala Tyr
                565                 570                 575

Ala Leu Leu Thr Ser Leu Asn Leu Lys Asp Ile Asn Tyr Val Asn Pro
            580                 585                 590

Val Ile Lys Trp Leu Ser Glu Glu Gln Arg Tyr Gly Gly Gly Phe Tyr
            595                 600                 605

Ser Thr Gln Asp Thr Ile Asn Ala Ile Glu Gly Leu Thr Glu Tyr Ser
            610                 615                 620

Leu Leu Val Lys Gln Leu Arg Leu Ser Met Asp Ile Asp Val Ser Tyr
625                 630                 635                 640

Lys His Lys Gly Ala Leu His Asn Tyr Lys Met Thr Asp Lys Asn Phe
                645                 650                 655

Leu Gly Arg Pro Val Glu Val Leu Leu Asn Asp Asp Leu Ile Val Ser
```

```
                  660                 665                 670
Thr Gly Phe Gly Ser Gly Leu Ala Thr Val His Val Thr Val Val
            675                 680                 685

His Lys Thr Ser Thr Glu Glu Val Cys Ser Phe Tyr Leu Lys Ile
        690                 695                 700

Asp Thr Gln Asp Ile Glu Ala Ser His Tyr Arg Gly Tyr Gly Asn Ser
705                 710                 715                 720

Asp Tyr Lys Arg Ile Val Ala Cys Ala Ser Tyr Lys Pro Ser Arg Glu
                725                 730                 735

Glu Ser Ser Ser Gly Ser Ser His Ala Val Met Asp Ile Ser Leu Pro
            740                 745                 750

Thr Gly Ile Ser Ala Asn Glu Glu Asp Leu Lys Ala Leu Val Glu Gly
        755                 760                 765

Val Asp Gln Leu Phe Thr Asp Tyr Gln Ile Lys Asp Gly His Val Ile
    770                 775                 780

Leu Gln Leu Asn Ser Ile Pro Ser Ser Asp Phe Leu Cys Val Arg Phe
785                 790                 795                 800

Arg Ile Phe Glu Leu Phe Glu Val Gly Phe Leu Ser Pro Ala Thr Phe
                805                 810                 815

Thr Val Tyr Glu Tyr His Arg Pro Asp Lys Gln Cys Thr Met Phe Tyr
            820                 825                 830

Ser Thr Ser Asn Ile Lys Ile Gln Lys Val Cys Glu Gly Ala Ala Cys
        835                 840                 845

Lys Cys Val Glu Ala Asp Cys Gly Gln Met Gln Glu Glu Leu Asp Leu
    850                 855                 860

Thr Ile Ser Ala Glu Thr Arg Lys Gln Thr Ala Cys Lys Pro Glu Ile
865                 870                 875                 880

Ala Tyr Ala Tyr Lys Val Ser Ile Thr Ser Ile Thr Val Glu Asn Val
                885                 890                 895

Phe Val Lys Tyr Lys Ala Thr Leu Leu Asp Ile Tyr Lys Thr Gly Glu
            900                 905                 910

Ala Val Ala Glu Lys Asp Ser Glu Ile Thr Phe Ile Lys Lys Val Thr
        915                 920                 925

Cys Thr Asn Ala Glu Leu Val Lys Gly Arg Gln Tyr Leu Ile Met Gly
    930                 935                 940

Lys Glu Ala Leu Gln Ile Lys Tyr Asn Phe Ser Phe Arg Tyr Ile Tyr
945                 950                 955                 960

Pro Leu Asp Ser Leu Thr Trp Ile Glu Tyr Trp Pro Arg Asp Thr Thr
                965                 970                 975

Cys Ser Ser Cys Gln Ala Phe Leu Ala Asn Leu Asp Glu Phe Ala Glu
            980                 985                 990

Asp Ile Phe Leu Asn Gly Cys
        995

<210> SEQ ID NO 4
<211> LENGTH: 655
<212> TYPE: PRT
<213> ORGANISM: Homo sapiens

<400> SEQUENCE: 4

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30
```

-continued

Asp Ala Thr Ile Ser Ile Lys Ser Tyr Pro Asp Lys Lys Phe Ser Tyr
           35                  40                  45

Ser Ser Gly His Val His Leu Ser Ser Glu Asn Lys Phe Gln Asn Ser
 50                  55                  60

Ala Ile Leu Thr Ile Gln Pro Lys Gln Leu Pro Gly Gly Gln Asn Pro
 65                  70                  75                  80

Val Ser Tyr Val Tyr Leu Glu Val Val Ser Lys His Phe Ser Lys Ser
                 85                  90                  95

Lys Arg Met Pro Ile Thr Tyr Asp Asn Gly Phe Leu Phe Ile His Thr
             100                 105                 110

Asp Lys Pro Val Tyr Thr Pro Asp Gln Ser Val Lys Val Arg Val Tyr
             115                 120                 125

Ser Leu Asn Asp Asp Leu Lys Pro Ala Lys Arg Glu Thr Val Leu Thr
 130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                 165                 170                 175

Arg Tyr Gly Met Trp Thr Ile Lys Ala Lys Tyr Lys Glu Asp Phe Ser
             180                 185                 190

Thr Thr Gly Thr Ala Tyr Phe Glu Val Lys Glu Tyr Val Leu Pro His
         195                 200                 205

Phe Ser Val Ser Ile Glu Pro Glu Tyr Asn Phe Ile Gly Tyr Lys Asn
     210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                 245                 250                 255

Leu Lys Asp Asp Gln Lys Glu Met Met Gln Thr Ala Met Gln Asn Thr
             260                 265                 270

Met Leu Ile Asn Gly Ile Ala Gln Val Thr Phe Asp Ser Glu Thr Ala
             275                 280                 285

Val Lys Glu Leu Ser Tyr Tyr Ser Leu Glu Asp Leu Asn Asn Lys Tyr
 290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
             325                 330                 335

Asn Leu Val Ala Thr Pro Leu Phe Leu Lys Pro Gly Ile Pro Tyr Pro
             340                 345                 350

Ile Lys Val Gln Val Lys Asp Ser Leu Asp Gln Leu Val Gly Gly Val
         355                 360                 365

Pro Val Ile Leu Asn Ala Gln Thr Ile Asp Val Asn Gln Glu Thr Ser
 370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                 405                 410                 415

Val Lys Thr Asp Ala Pro Asp Leu Pro Glu Glu Asn Gln Ala Arg Glu
             420                 425                 430

Gly Tyr Arg Ala Ile Ala Tyr Ser Ser Leu Ser Gln Ser Tyr Leu Tyr
             435                 440                 445

Ile Asp Trp Thr Asp Asn His Lys Ala Leu Leu Val Gly Glu His Leu

```
                    450                 455                 460

Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                    485                 490                 495

Arg Glu Lys Phe Ser Asp Ala Ser Tyr Gln Ser Ile Asn Ile Pro Val
                500                 505                 510

Thr Gln Asn Met Val Pro Ser Ser Arg Leu Leu Val Tyr Tyr Ile Val
            515                 520                 525

Thr Gly Glu Gln Thr Ala Glu Leu Val Ser Asp Ser Val Trp Leu Asn
        530                 535                 540

Ile Glu Glu Lys Cys Gly Asn Gln Leu Gln Val His Leu Ser Pro Asp
545                 550                 555                 560

Ala Asp Ala Tyr Ser Pro Gly Gln Thr Val Ser Leu Asn Met Ala Thr
                    565                 570                 575

Gly Met Asp Ser Trp Val Ala Leu Ala Ala Val Asp Ser Ala Val Tyr
                580                 585                 590

Gly Val Gln Arg Gly Ala Lys Lys Pro Leu Glu Arg Val Phe Gln Phe
                595                 600                 605

Leu Glu Lys Ser Asp Leu Gly Cys Gly Ala Gly Gly Leu Asn Asn
            610                 615                 620

Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Leu
                    645                 650                 655

<210> SEQ ID NO 5
<211> LENGTH: 21
<212> TYPE: PRT
<213> ORGANISM: Homo sapiens

<400> SEQUENCE: 5

Val Ile Asp His Gln Gly Thr Lys Ser Ser Lys Cys Val Arg Gln Lys
1               5                   10                  15

Val Glu Gly Ser Ser
            20

<210> SEQ ID NO 6
<211> LENGTH: 5
<212> TYPE: PRT
<213> ORGANISM: Homo sapiens

<400> SEQUENCE: 6

Lys Ser Ser Lys Cys
1               5

<210> SEQ ID NO 7
<211> LENGTH: 127
<212> TYPE: PRT
<213> ORGANISM: Homo sapiens

<400> SEQUENCE: 7

Asn Phe Ser Leu Glu Thr Trp Phe Gly Lys Glu Ile Leu Val Lys Thr
1               5                   10                  15

Leu Arg Val Val Pro Glu Gly Val Lys Arg Glu Ser Tyr Ser Gly Val
            20                  25                  30

Thr Leu Asp Pro Arg Gly Ile Tyr Gly Thr Ile Ser Arg Arg Lys Glu
        35                  40                  45
```

```
Phe Pro Tyr Arg Ile Pro Leu Asp Leu Val Pro Lys Thr Glu Ile Lys
        50                  55                  60

Arg Ile Leu Ser Val Lys Gly Leu Leu Val Gly Glu Ile Leu Ser Ala
 65                  70                  75                  80

Val Leu Ser Gln Glu Gly Ile Asn Ile Leu Thr His Leu Pro Lys Gly
                 85                  90                  95

Ser Ala Glu Ala Glu Leu Met Ser Val Val Pro Val Phe Tyr Val Phe
                100                 105                 110

His Tyr Leu Glu Thr Gly Asn His Trp Asn Ile Phe His Ser Asp
                115                 120                 125

<210> SEQ ID NO 8
<211> LENGTH: 200
<212> TYPE: PRT
<213> ORGANISM: Homo sapiens

<400> SEQUENCE: 8

Ser Glu Ser Pro Val Ile Asp His Gln Gly Thr Lys Ser Ser Lys Cys
 1               5                  10                  15

Val Arg Gln Lys Val Glu Gly Ser Ser Ser His Leu Val Thr Phe Thr
                20                  25                  30

Val Leu Pro Leu Glu Ile Gly Leu His Asn Ile Asn Phe Ser Leu Glu
                35                  40                  45

Thr Trp Phe Gly Lys Glu Ile Leu Val Lys Thr Leu Arg Val Val Pro
        50                  55                  60

Glu Gly Val Lys Arg Glu Ser Tyr Ser Gly Val Thr Leu Asp Pro Arg
 65                  70                  75                  80

Gly Ile Tyr Gly Thr Ile Ser Arg Arg Lys Glu Phe Pro Tyr Arg Ile
                 85                  90                  95

Pro Leu Asp Leu Val Pro Lys Thr Glu Ile Lys Arg Ile Leu Ser Val
                100                 105                 110

Lys Gly Leu Leu Val Gly Glu Ile Leu Ser Ala Val Leu Ser Gln Glu
            115                 120                 125

Gly Ile Asn Ile Leu Thr His Leu Pro Lys Gly Ser Ala Glu Ala Glu
        130                 135                 140

Leu Met Ser Val Val Pro Val Phe Tyr Val Phe His Tyr Leu Glu Thr
145                 150                 155                 160

Gly Asn His Trp Asn Ile Phe His Ser Asp Pro Leu Ile Glu Lys Gln
                165                 170                 175

Lys Leu Lys Lys Lys Leu Lys Gly Met Leu Ser Ile Met Ser Tyr
            180                 185                 190

Arg Asn Ala Asp Tyr Ser Tyr Ser
        195                 200

<210> SEQ ID NO 9
<211> LENGTH: 30
<212> TYPE: PRT
<213> ORGANISM: Homo sapiens

<400> SEQUENCE: 9

Ser His Lys Asp Met Gln Leu Gly Arg Leu His Met Lys Thr Leu Leu
 1               5                  10                  15

Pro Val Ser Lys Pro Glu Ile Arg Ser Tyr Phe Pro Glu Ser
                20                  25                  30

<210> SEQ ID NO 10
```

```
<211> LENGTH: 325
<212> TYPE: PRT
<213> ORGANISM: Homo sapiens

<400> SEQUENCE: 10

Ser His Lys Asp Met Gln Leu Gly Arg Leu His Met Lys Thr Leu Leu
1               5                   10                  15

Pro Val Ser Lys Pro Glu Ile Arg Ser Tyr Phe Pro Glu Ser Trp Leu
            20                  25                  30

Trp Glu Val His Leu Val Pro Arg Arg Lys Gln Leu Gln Phe Ala Leu
        35                  40                  45

Pro Asp Ser Leu Thr Thr Trp Glu Ile Gln Gly Ile Gly Ile Ser Asn
    50                  55                  60

Thr Gly Ile Cys Val Ala Asp Thr Val Lys Ala Lys Val Phe Lys Asp
65                  70                  75                  80

Val Phe Leu Glu Met Asn Ile Pro Tyr Ser Val Val Arg Gly Glu Gln
                85                  90                  95

Ile Gln Leu Lys Gly Thr Val Tyr Asn Tyr Arg Thr Ser Gly Met Gln
            100                 105                 110

Phe Cys Val Lys Met Ser Ala Val Glu Gly Ile Cys Thr Ser Glu Ser
        115                 120                 125

Pro Val Ile Asp His Gln Gly Thr Lys Ser Ser Lys Cys Val Arg Gln
    130                 135                 140

Lys Val Glu Gly Ser Ser Ser His Leu Val Thr Phe Thr Val Leu Pro
145                 150                 155                 160

Leu Glu Ile Gly Leu His Asn Ile Asn Phe Ser Leu Glu Thr Trp Phe
                165                 170                 175

Gly Lys Glu Ile Leu Val Lys Thr Leu Arg Val Val Pro Glu Gly Val
            180                 185                 190

Lys Arg Glu Ser Tyr Ser Gly Val Thr Leu Asp Pro Arg Gly Ile Tyr
        195                 200                 205

Gly Thr Ile Ser Arg Arg Lys Glu Phe Pro Tyr Arg Ile Pro Leu Asp
    210                 215                 220

Leu Val Pro Lys Thr Glu Ile Lys Arg Ile Leu Ser Val Lys Gly Leu
225                 230                 235                 240

Leu Val Gly Glu Ile Leu Ser Ala Val Leu Ser Gln Glu Gly Ile Asn
                245                 250                 255

Ile Leu Thr His Leu Pro Lys Gly Ser Ala Glu Ala Glu Leu Met Ser
            260                 265                 270

Val Val Pro Val Phe Tyr Val Phe His Tyr Leu Glu Thr Gly Asn His
        275                 280                 285

Trp Asn Ile Phe His Ser Asp Pro Leu Ile Glu Lys Gln Lys Leu Lys
    290                 295                 300

Lys Lys Leu Lys Glu Gly Met Leu Ser Ile Met Ser Tyr Arg Asn Ala
305                 310                 315                 320

Asp Tyr Ser Tyr Ser
                325

<210> SEQ ID NO 11
<211> LENGTH: 17
<212> TYPE: PRT
<213> ORGANISM: Homo sapiens

<400> SEQUENCE: 11

Asp His Gln Gly Thr Lys Ser Ser Lys Cys Val Arg Gln Lys Val Glu
1               5                   10                  15
```

Gly

<210> SEQ ID NO 12
<211> LENGTH: 74
<212> TYPE: PRT
<213> ORGANISM: Homo sapiens

<400> SEQUENCE: 12

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 13
<211> LENGTH: 20
<212> TYPE: PRT
<213> ORGANISM: Homo sapiens

<400> SEQUENCE: 13

Cys Cys Tyr Asp Gly Ala Cys Val Asn Asn Asp Glu Thr Cys Glu Gln
1               5                   10                  15

Arg Ala Ala Arg
            20

<210> SEQ ID NO 14
<211> LENGTH: 18
<212> TYPE: PRT
<213> ORGANISM: Homo sapiens

<400> SEQUENCE: 14

Lys Cys Cys Tyr Asp Gly Ala Cys Val Asn Asn Asp Glu Thr Cys Glu
1               5                   10                  15

Gln Arg

<210> SEQ ID NO 15
<211> LENGTH: 10
<212> TYPE: PRT
<213> ORGANISM: Homo sapiens

<400> SEQUENCE: 15

Val Asn Asn Asp Glu Thr Cys Glu Gln Arg
1               5                   10

<210> SEQ ID NO 16
<211> LENGTH: 6
<212> TYPE: PRT
<213> ORGANISM: Homo sapiens

<400> SEQUENCE: 16

Val Asn Asn Asp Glu Thr
1               5

<210> SEQ ID NO 17
<211> LENGTH: 9
<212> TYPE: PRT

```
<213> ORGANISM: Homo sapiens

<400> SEQUENCE: 17

Ala Ala Arg Ile Ser Leu Gly Pro Arg
1               5

<210> SEQ ID NO 18
<211> LENGTH: 19
<212> TYPE: PRT
<213> ORGANISM: Homo sapiens

<400> SEQUENCE: 18

Cys Cys Tyr Asp Gly Ala Cys Val Asn Asn Asp Glu Thr Cys Glu Gln
1               5                   10                  15

Arg Ala Ala

<210> SEQ ID NO 19
<211> LENGTH: 18
<212> TYPE: PRT
<213> ORGANISM: Homo sapiens

<400> SEQUENCE: 19

Cys Cys Tyr Asp Gly Ala Cys Val Asn Asn Asp Glu Thr Cys Glu Gln
1               5                   10                  15

Arg Ala

<210> SEQ ID NO 20
<211> LENGTH: 17
<212> TYPE: PRT
<213> ORGANISM: Homo sapiens

<400> SEQUENCE: 20

Cys Cys Tyr Asp Gly Ala Cys Val Asn Asn Asp Glu Thr Cys Glu Gln
1               5                   10                  15

Arg

<210> SEQ ID NO 21
<211> LENGTH: 16
<212> TYPE: PRT
<213> ORGANISM: Homo sapiens

<400> SEQUENCE: 21

Cys Cys Tyr Asp Gly Ala Cys Val Asn Asn Asp Glu Thr Cys Glu Gln
1               5                   10                  15

<210> SEQ ID NO 22
<211> LENGTH: 15
<212> TYPE: PRT
<213> ORGANISM: Homo sapiens

<400> SEQUENCE: 22

Cys Cys Tyr Asp Gly Ala Cys Val Asn Asn Asp Glu Thr Cys Glu
1               5                   10                  15

<210> SEQ ID NO 23
<211> LENGTH: 19
<212> TYPE: PRT
<213> ORGANISM: Homo sapiens

<400> SEQUENCE: 23

Cys Tyr Asp Gly Ala Cys Val Asn Asn Asp Glu Thr Cys Glu Gln Arg
1               5                   10                  15
```

Ala Ala Arg

<210> SEQ ID NO 24
<211> LENGTH: 18
<212> TYPE: PRT
<213> ORGANISM: Homo sapiens

<400> SEQUENCE: 24

Tyr Asp Gly Ala Cys Val Asn Asn Asp Glu Thr Cys Glu Gln Arg Ala
1               5                   10                  15

Ala Arg

<210> SEQ ID NO 25
<211> LENGTH: 19
<212> TYPE: PRT
<213> ORGANISM: Homo sapiens

<400> SEQUENCE: 25

Cys Tyr Asp Gly Ala Cys Val Asn Asn Asp Glu Thr Cys Glu Gln Arg
1               5                   10                  15

Ala Ala Arg

<210> SEQ ID NO 26
<211> LENGTH: 925
<212> TYPE: PRT
<213> ORGANISM: Homo sapiens

<400> SEQUENCE: 26

Leu His Met Lys Thr Leu Leu Pro Val Ser Lys Pro Glu Ile Arg Ser
1               5                   10                  15

Tyr Phe Pro Glu Ser Trp Leu Trp Glu Val His Leu Val Pro Arg Arg
                20                  25                  30

Lys Gln Leu Gln Phe Ala Leu Pro Asp Ser Leu Thr Thr Trp Glu Ile
            35                  40                  45

Gln Gly Ile Gly Ile Ser Asn Thr Gly Ile Cys Val Ala Asp Thr Val
    50                  55                  60

Lys Ala Lys Val Phe Lys Asp Val Phe Leu Glu Met Asn Ile Pro Tyr
65                  70                  75                  80

Ser Val Val Arg Gly Glu Gln Ile Gln Leu Lys Gly Thr Val Tyr Asn
                85                  90                  95

Tyr Arg Thr Ser Gly Met Gln Phe Cys Val Lys Met Ser Ala Val Glu
            100                 105                 110

Gly Ile Cys Thr Ser Glu Ser Pro Val Ile Asp His Gln Gly Thr Lys
        115                 120                 125

Ser Ser Lys Cys Val Arg Gln Lys Val Glu Gly Ser Ser Ser His Leu
    130                 135                 140

Val Thr Phe Thr Val Leu Pro Leu Glu Ile Gly Leu His Asn Ile Asn
145                 150                 155                 160

Phe Ser Leu Glu Thr Trp Phe Gly Lys Glu Ile Leu Val Lys Thr Leu
                165                 170                 175

Arg Val Val Pro Glu Gly Val Lys Arg Glu Ser Tyr Ser Gly Val Thr
            180                 185                 190

Leu Asp Pro Arg Gly Ile Tyr Gly Thr Ile Ser Arg Arg Lys Glu Phe
        195                 200                 205

Pro Tyr Arg Ile Pro Leu Asp Leu Val Pro Lys Thr Glu Ile Lys Arg
    210                 215                 220

Ile Leu Ser Val Lys Gly Leu Leu Val Gly Glu Ile Leu Ser Ala Val

-continued

```
            225                 230                 235                 240
Leu Ser Gln Glu Gly Ile Asn Ile Leu Thr His Leu Pro Lys Gly Ser
                245                 250                 255

Ala Glu Ala Glu Leu Met Ser Val Val Pro Val Phe Tyr Val Phe His
                260                 265                 270

Tyr Leu Glu Thr Gly Asn His Trp Asn Ile Phe His Ser Asp Pro Leu
                275                 280                 285

Ile Glu Lys Gln Lys Leu Lys Lys Leu Lys Glu Gly Met Leu Ser
    290                 295                 300

Ile Met Ser Tyr Arg Asn Ala Asp Tyr Ser Tyr Ser Val Trp Lys Gly
305                 310                 315                 320

Gly Ser Ala Ser Thr Trp Leu Thr Ala Phe Ala Leu Arg Val Leu Gly
                325                 330                 335

Gln Val Asn Lys Tyr Val Glu Gln Asn Gln Ser Ile Cys Asn Ser
                340                 345                 350

Leu Leu Trp Leu Val Glu Asn Tyr Gln Leu Asp Asn Gly Ser Phe Lys
                355                 360                 365

Glu Asn Ser Gln Tyr Gln Pro Ile Lys Leu Gln Gly Thr Leu Pro Val
    370                 375                 380

Glu Ala Arg Glu Asn Ser Leu Tyr Leu Thr Ala Phe Thr Val Ile Gly
385                 390                 395                 400

Ile Arg Lys Ala Phe Asp Ile Cys Pro Leu Val Lys Ile Asp Thr Ala
                405                 410                 415

Leu Ile Lys Ala Asp Asn Phe Leu Leu Glu Asn Thr Leu Pro Ala Gln
                420                 425                 430

Ser Thr Phe Thr Leu Ala Ile Ser Ala Tyr Ala Leu Ser Leu Gly Asp
                435                 440                 445

Lys Thr His Pro Gln Phe Arg Ser Ile Val Ser Ala Leu Lys Arg Glu
                450                 455                 460

Ala Leu Val Lys Gly Asn Pro Pro Ile Tyr Arg Phe Trp Lys Asp Asn
465                 470                 475                 480

Leu Gln His Lys Asp Ser Ser Val Pro Asn Thr Gly Thr Ala Arg Met
                485                 490                 495

Val Glu Thr Thr Ala Tyr Ala Leu Leu Thr Ser Leu Asn Leu Lys Asp
                500                 505                 510

Ile Asn Tyr Val Asn Pro Val Ile Lys Trp Leu Ser Glu Glu Gln Arg
                515                 520                 525

Tyr Gly Gly Gly Phe Tyr Ser Thr Gln Asp Thr Ile Asn Ala Ile Glu
                530                 535                 540

Gly Leu Thr Glu Tyr Ser Leu Leu Val Lys Gln Leu Arg Leu Ser Met
545                 550                 555                 560

Asp Ile Asp Val Ser Tyr Lys His Lys Gly Ala Leu His Asn Tyr Lys
                565                 570                 575

Met Thr Asp Lys Asn Phe Leu Gly Arg Pro Val Glu Val Leu Leu Asn
                580                 585                 590

Asp Asp Leu Ile Val Ser Thr Gly Phe Gly Ser Gly Leu Ala Thr Val
                595                 600                 605

His Val Thr Thr Val Val His Lys Thr Ser Thr Ser Glu Glu Val Cys
                610                 615                 620

Ser Phe Tyr Leu Lys Ile Asp Thr Gln Asp Ile Glu Ala Ser His Tyr
625                 630                 635                 640

Arg Gly Tyr Gly Asn Ser Asp Tyr Lys Arg Ile Val Ala Cys Ala Ser
                645                 650                 655
```

```
Tyr Lys Pro Ser Arg Glu Glu Ser Ser Ser Gly Ser Ser His Ala Val
            660             665             670

Met Asp Ile Ser Leu Pro Thr Gly Ile Ser Ala Asn Glu Glu Asp Leu
            675             680             685

Lys Ala Leu Val Glu Gly Val Asp Gln Leu Phe Thr Asp Tyr Gln Ile
            690             695             700

Lys Asp Gly His Val Ile Leu Gln Leu Asn Ser Ile Pro Ser Ser Asp
705             710             715             720

Phe Leu Cys Val Arg Phe Arg Ile Phe Glu Leu Phe Glu Val Gly Phe
                725             730             735

Leu Ser Pro Ala Thr Phe Thr Val Tyr Glu Tyr His Arg Pro Asp Lys
            740             745             750

Gln Cys Thr Met Phe Tyr Ser Thr Ser Asn Ile Lys Ile Gln Lys Val
            755             760             765

Cys Glu Gly Ala Ala Cys Lys Cys Val Glu Ala Asp Cys Gly Gln Met
    770             775             780

Gln Glu Glu Leu Asp Leu Thr Ile Ser Ala Glu Thr Arg Lys Gln Thr
785             790             795             800

Ala Cys Lys Pro Glu Ile Ala Tyr Ala Tyr Lys Val Ser Ile Thr Ser
                805             810             815

Ile Thr Val Glu Asn Val Phe Val Lys Tyr Lys Ala Thr Leu Leu Asp
            820             825             830

Ile Tyr Lys Thr Gly Glu Ala Val Ala Glu Lys Asp Ser Glu Ile Thr
        835             840             845

Phe Ile Lys Lys Val Thr Cys Thr Asn Ala Glu Leu Val Lys Gly Arg
    850             855             860

Gln Tyr Leu Ile Met Gly Lys Glu Ala Leu Gln Ile Lys Tyr Asn Phe
865             870             875             880

Ser Phe Arg Tyr Ile Tyr Pro Leu Asp Ser Leu Thr Trp Ile Glu Tyr
            885             890             895

Trp Pro Arg Asp Thr Thr Cys Ser Ser Cys Gln Ala Phe Leu Ala Asn
            900             905             910

Leu Asp Glu Phe Ala Glu Asp Ile Phe Leu Asn Gly Cys
        915             920             925
```

METHODS FOR TREATING COMPLEMENT-ASSOCIATED DISORDERS

CROSS-REFERENCE TO RELATED APPLICATIONS

This application is a divisional of U.S. patent application Ser. No. 13/128,523, filed Oct. 25, 2011, which is a 35 U.S.C. 371 national stage filing of International Application No. PCT/US2009/063929, filed on Nov. 10, 2009, which claims the benefit of U.S. Provisional Patent Application Ser. No. 61/198,803, filed on Nov. 10, 2008; 61/199,563, filed on Nov. 18, 2008; 61/199,562, filed on Nov. 18, 2008; 61/199,569, filed on Nov. 18, 2008; 61/199,764, filed on Nov. 19, 2008; 61/200,640, filed on Dec. 1, 2008; 61/200,634, filed on Dec. 1, 2008; 61/200,635, filed on Dec. 1, 2008; 61/181,788, filed on May 28, 2009; and 61/228,047, filed on Jul. 23, 2009, the disclosures of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 22, 2016, is named AXJ_136USDV_Seq_List.txt and is 61,853 bytes in size.

TECHNICAL FIELD

The field of the invention is medicine, immunology, molecular biology, and protein chemistry.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

The complement cascade can progress via the classical pathway (CP), the lectin pathway, or the alternative pathway (AP). The lectin pathway is typically initiated with binding of mannose-binding lectin (MBL) to high mannose substrates. The AP can be antibody independent, and can be initiated by certain molecules on pathogen surfaces. The CP is typically initiated by antibody recognition of, and binding to, an antigenic site on a target cell. These pathways converge at the C3 convertase—the point where complement component C3 is cleaved by an active protease to yield C3a and C3b.

The AP C3 convertase is initiated by the spontaneous hydrolysis of complement component C3, which is abundant in the plasma in the blood. This process, also known as "tickover," occurs through the spontaneous cleavage of a thioester bond in C3 to form C3i or C3(H$_2$O). Tickover is facilitated by the presence of surfaces that support the binding of activated C3 and/or have neutral or positive charge characteristics (e.g., bacterial cell surfaces). This formation of C3(H$_2$O) allows for the binding of plasma protein Factor B, which in turn allows Factor D to cleave Factor B into Ba and Bb. The Bb fragment remains bound to C3 to form a complex containing C3(H$_2$O)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to thus form the surface-bound AP C3 convertase complex containing C3b, Bb. (See, e.g., Müller-Eberhard (1988) *Ann Rev Biochem* 57:321-347.)

The AP C5 convertase—(C3b)$_2$,Bb—is formed upon addition of a second C3b monomer to the AP C3 convertase. (See, e.g., Medicus et al. (1976) *J Exp Med* 144:1076-1093 and Fearon et al. (1975) *J Exp Med* 142:856-863.) The role of the second C3b molecule is to bind C5 and present it for cleavage by Bb. (See, e.g., Isenman et al. (1980) *J Immunol* 124:326-331.) The AP C3 and C5 convertases are stabilized by the addition of the trimeric protein properdin as described in, e.g., Medicus et al. (1976), supra. However, properdin binding is not required to form a functioning alternative pathway C3 or C5 convertase. (See, e.g., Schreiber et al. (1978) *Proc Natl Acad Sci USA* 75: 3948-3952 and Sissons et al. (1980) *Proc Natl Acad Sci USA* 77: 559-562.)

The CP C3 convertase is formed upon interaction of complement component C1, which is a complex of C1q, C1r, and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to thereby generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase—C4b,C2a,C3b—is formed upon addition of a C3b monomer to the CP C3 convertase. (See, e.g., Müller-Eberhard (1988), supra and Cooper et al. (1970) *J Exp Med* 132:775-793.)

In addition to its role in C3 and C5 convertases, C3b also functions as an opsonin through its interaction with complement receptors present on the surfaces of antigen-presenting cells such as macrophages and dendritic cells. The opsonic function of C3b is generally considered to be one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5, which is a 190 kDa beta globulin found in normal serum at approximately 75 µg/ml (0.4 µM). C5 is glycosylated, with about 1.5-3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J. Immunol.* 146:362-368). The cDNA sequence of the transcript of this gene predicts a secreted pro-C5 precursor of 1658 amino acids along with an 18 amino acid leader sequence (see, e.g., U.S. Pat. No. 6,355,245).

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733 of the above sequence. A compound that would bind at, or adjacent to, this cleavage site would have the potential to block access of the C5 convertase enzymes to the cleavage site and thereby act as a complement inhibitor.

C5 can also be activated by means other than C5 convertase activity. Limited trypsin digestion (see, e.g., Minta and Man (1997) *J Immunol.* 119:1597-1602 and Wetsel and Kolb (1982) *J Immunol.* 128:2209-2216) and acid treatment (Yamamoto and Gewurz (1978) *J Immunol.* 120:2008 and Damerau et al. (1989) *Molec. Immunol.* 26:1133-1142) can also cleave C5 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

The first step in the formation of the terminal complement complex involves the combination of C5b with C6, C7, and C8 to form the C5b-8 complex at the surface of the target cell. Upon the binding of the C5b-8 complex with several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

While a properly functioning complement system provides a robust defense against infecting microbes, inappropriate regulation or activation of complement has been implicated in the pathogenesis of a variety of disorders including, e.g., rheumatoid arthritis (RA); lupus nephritis; ischemia-reperfusion injury; atypical hemolytic uremic syndrome (aHUS); dense deposit disease (DDD); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis. (See, e.g., Holers et al. (2008) *Immunological Reviews* 223:300-316.)

SUMMARY

The present disclosure relates to compositions containing an inhibitor of human complement (e.g., an inhibitor of complement component C5 such as an anti-C5 antibody) and methods for using the compositions to treat or prevent complement-associated disorders. In some embodiments, the compositions contain an antibody, or antigen-binding fragment thereof, that binds to a human complement component C5 protein. In some embodiments, the compositions contain an antibody, or antigen-binding fragment thereof, that binds to human C5 fragment C5a or C5b. In some embodiments, the C5 inhibitor is a small molecule or a nucleic acid such as, e.g., a siRNA or an anti-sense RNA that binds to and promotes inactivation of C5 mRNA in a mammal.

Complement-associated disorders include any medical disorder in a human, the treatment of which would benefit directly or indirectly from inhibition of the complement system. The disorders are generally characterized by inappropriate regulation of the complement system such as inappropriate: (i) activation of the complement system or (ii) duration of an activated complement system in a subject. Complement-associated disorders include, without limitation, inflammatory and autoimmune disorders. A complement-associated disorder can be, e.g., RA; antiphospholipid antibody syndrome (APS); lupus nephritis; ischemia-reperfusion injury; aHUS; typical (also referred to as diarrheal or infectious) hemolytic uremic syndrome (tHUS); DDD; neuromyelitis optica (NMO); multifocal motor neuropathy (MMN); MS; macular degeneration (e.g., AMD); HELLP syndrome; TTP; spontaneous fetal loss; Pauci-immune vasculitis; epidermolysis bullosa; recurrent fetal loss; and traumatic brain injury. In some embodiments, the complement-associated disorder is a complement-associated vascular disorder such as a cardiovascular disorder, myocarditis, a cerebrovascular disorder, a peripheral (e.g., musculoskeletal) vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA). Additional complement-associated disorders include, without limitation, myasthenia gravis (MG), cold agglutinin disease (CAD), dermatomyositis, paroxysmal cold hemoglobinuria (PCH), Graves' disease, atherosclerosis, Alzheimer's disease, systemic inflammatory response sepsis, septic shock, spinal cord injury, glomerulonephritis, Hashimoto's thyroiditis, type I diabetes, psoriasis, pemphigus, autoimmune hemolytic anemia (AIHA), idiopathic thrombocytopenic purpura (ITP), Goodpasture syndrome, Degos disease, and catastrophic APS (CAPS).

In one aspect, the disclosure features a method for treating or preventing a complement-associated disorder in a human. The method includes administering to a human in need thereof a therapeutically effective amount of a composition comprising an inhibitor of human complement (e.g., an inhibitor of human complement component C5).

In another aspect, the disclosure features a method for treating or preventing a complement-associated disorder in a human, which method comprises administering to a human in need thereof a composition comprising a therapeutically effective amount of an inhibitor of human complement (e.g., an inhibitor of human complement component C5).

In some embodiments of any of the methods described herein, the inhibitor can inhibit the expression of a human complement component C5 protein. The inhibitor can inhibit the protein expression of a human complement component C5 protein or inhibit the expression of an mRNA encoding the protein. In some embodiments of any of the methods described herein, the inhibitor can inhibit the cleavage of human complement component C5 into fragments C5a and C5b.

In some embodiments of any of the methods described herein, the inhibitor binds to, and inhibits, one or both of C5a and C5b. The inhibitor can be, e.g., an antibody that binds to C5a or C5b. In some embodiments, the inhibitor is an antibody that binds to C5a, but does not bind to full-length C5. In some embodiments, the inhibitor is an antibody that binds to C5b, but does not bind to full-length C5. In some embodiments, the inhibitor is an antibody that binds to a human C5a protein or a fragment thereof having an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:12-25. In some embodiments, the inhibitor is an antibody that binds to human C5a protein having the amino acid sequence depicted in SEQ ID NO:12. In some embodiments, the inhibitor is an antibody that binds to a human C5b protein or fragment thereof having an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:4 or 26. In some embodiments, the inhibitor is an antibody that binds to human C5b protein having the amino acid sequence depicted in SEQ ID NO:4 or 26.

In some embodiments of any of the methods described herein, the inhibitor can be selected from the group consisting of a polypeptide, a polypeptide analog, a nucleic acid, a nucleic acid analog, and a small molecule. The polypeptide can be, or consist of, an antibody, or antigen-binding fragment thereof, that binds to a human complement component C5 protein such as any of those described herein. In some embodiments, the antibody can bind to the alpha chain of the complement component C5 protein. In some embodiments, the antibody can bind to the beta chain of the complement component C5 protein. In some embodiments, the antibody can bind to the alpha chain of human complement component C5, and the antibody can (i) inhibit complement activation in a human body fluid, (ii) inhibit the binding of purified human complement component C5 to either human complement component C3b or human complement component C4b, and/or (iii) not bind to the human complement activation product free C5a (or a combination of any of the foregoing properties). The antibody can bind to the human complement component C5 protein having, or consisting of, the amino acid sequence depicted in any one of SEQ ID NOs:1-11. The antibody can bind to an isolated oligopeptide comprising an amino acid sequence corresponding to amino acid position 8 through amino acid position 12 of SEQ ID NO:5. In some embodiments, the antibody can be a monoclonal antibody, a single-chain antibody, a humanized antibody, a fully human antibody, a polyclonal antibody, a recombinant antibody, a diabody, a chimerized or chimeric antibody, a deimmunized human antibody, a fully human antibody, a single chain antibody, an Fv fragment, an Fd fragment, an Fab fragment, an Fab' fragment, or an F(ab')$_2$ fragment. In some embodiments, the antibody can be eculizumab or pexelizumab.

In some embodiments of any of the methods described herein, the composition can be intravenously administered to the human.

In some embodiments of any of the methods described herein, the complement-associated disorder is an alternative complement pathway-associated disorder. In some embodiments of any of the methods described herein, the complement-associated disorder is a classical complement pathway-associated disorder. In some embodiments, the complement-associated disorder is selected from the group consisting of rheumatoid arthritis, ischemia-reperfusion injury, atypical hemolytic uremic syndrome, thrombotic thrombocytopenic purpura, dense deposit disease, age-related macular degeneration, spontaneous fetal loss, Pauci-immune vasculitis, epidermolysis bullosa, recurrent fetal loss, multiple sclerosis, HELLP, pre-eclampsia, traumatic brain injury, Alzheimer's disease, myasthenia gravis, cold agglutinin disease, dermatomyositis, Graves' disease, Hashimoto's thyroiditis, type I diabetes, psoriasis, pemphigus, autoimmune hemolytic anemia, idiopathic thrombocytopenic purpura, Goodpasture syndrome, antiphospholipid syndrome, catastrophic antiphospholipid syndrome, neuromyelitis optica (NMO), multifocal motor neuropathy (MMN), Degos disease, and any other complement-associated disorder described herein.

In some embodiments, any of the methods described herein can further include the step of identifying the human as having, suspected of having, or at risk for developing, a complement-associated disorder. In some embodiments, any of the methods described herein can also include, after the administering, monitoring the human for an improvement in one or more symptoms of the complement-associated disorder.

In embodiments of any of the methods described herein where the complement-associated disorder is aHUS, the aHUS can be genetic, acquired, or idiopathic form. In some embodiments, the aHUS can be complement factor H (CFH)-associated aHUS (e.g., due to mutations in CFH or the presence of antibodies in the subject that bind to CFH), membrane cofactor protein (MCP)-associated aHUS, complement factor I (CFI)-associated aHUS, C4b-binding protein (C4BP)-associated aHUS, a von Willibrand Factor (vWF)-associated disorder, complement factor B-(CFB)-associated aHUS, or a disorder of the alternative pathway that results in low C3 levels as a result of increased C3 consumption.

In some embodiments, any of the methods described herein can further include identifying the subject as one having, suspected of having, or at risk for developing, aHUS.

In some embodiments, any of the methods described herein can include, after the administering, monitoring the subject for an improvement in one or more symptoms of aHUS.

In some embodiments of any of the methods described herein, the composition can be administered to the subject prior to, during, or following a plasma therapy (e.g., plasma exchange or plasma infusion). In some embodiments, administration of the C5 inhibitor to the subject can alleviate the need for plasma therapy by a patient. For example, in some embodiments, administration (e.g., chronic administration) of the C5 inhibitor to the subject can alleviate or substantially reduce the need for plasma therapy by a patient for at least 2 months (e.g., 3 months, 4 months, 5 months, 6 months, 7 months, 8 months, 9 months, 10 months, 11 months, or 12 months or 1, 2, 3, 4, 5, or 6 years or more). In some embodiments, any of the methods described herein can include administering to the subject one or more additional active agents useful for treating typical HUS or aHUS. The one or more additional active agents can be, e.g., selected from the group consisting of anti-hypertensives, anti-platelet agents, prostacyclin, fibrinolytic agents, and anti-oxidants.

In some embodiments, the human is an infant. The infant can be, e.g., 0.5 (e.g., 1, 1.5, 2, 2.5, 3, 3.5, 4, 4.5, 5, 5.5, 6, 6.5, 7, 7.5, 8, 8.5, 9, or 9.5) years old. The infant can be less than 10 (e.g., less than 9.5, 9, 8.5, 8, 7.5, 7, 6.5, 6, 5.5, 5, 4.5, 4, 3.5, 3, 2.5, 2, 1.5, 1, or less than 1) year(s) old.

In embodiments of any of the methods described herein where the complement-associated disorder is typical HUS, the typical HUS can be associated with an *E. coli* infection in or on the human. The *E. coli* infection can be, e.g., an *E. coli* O157 (e.g., O157:H7), O26, O103, O111, or O145 infection. In some embodiments of any of the methods described herein, the typical hemolytic uremic syndrome can be associated with a *Shigella dysenteriae* infection in or on the human. The *Shigella dysenteriae* infection can be a *Shigella dysenteriae* type 1 infection.

In some embodiments, any of the methods described herein can further include identifying the human as one having, suspected of having, or at risk for developing, typical hemolytic uremic syndrome.

In some embodiments, any of the methods described herein can include, after the administering, monitoring the human for an improvement in one or more symptoms of typical hemolytic uremic syndrome.

In embodiments of any of the methods described herein where the complement-associated disorder is CAPS, the CAPS can be associated with a precipitating condition. Precipitating conditions can include, e.g., a cancer, transplantation, an infection, surgery, primary antiphospholipid syndrome, or an autoimmune disorder such as rheumatoid arthritis or systemic lupus erythematosus. Accordingly, in some embodiments, the CAPS can be associated with a cancer such as, but not limited to, gastric cancer, ovarian cancer, lymphoma, leukemia, endometrial cancer, adenocarcinoma, lung cancer, or any other cancers known in the art to precipitate or be associated with CAPS. In some embodiments, the CAPS can be idiopathic.

In some embodiments, any of the methods described herein can also include identifying the human as one having, suspected of having, or at risk for developing, CAPS. In some embodiments, any of the methods described herein can include, after the administering, monitoring the human for an improvement in one or more symptoms of CAPS.

In some embodiments of any of the methods described herein, the composition can be administered to the human prior to, during, or following a plasma exchange, plasmapheresis, IVIG, or any other additional therapy for treating CAPS.

In some embodiments, any of the methods described herein can also include administering to the human one or more additional active agents useful for treating CAPS. The one or more additional active agents can be selected from the group consisting of anti-hypertensives, anti-cytokine agents, steroids, anti-coagulants, or fibrinolytic agents.

In embodiments of any of the methods described herein where the complement-associated disorder is TTP, the TTP can be inherited. For example, a human can carry one or more (e.g., two, three, four, or five or more) mutations in the ADAMTS13 gene. In some embodiments of any of the methods described herein, the TTP can be an acquired form. For example, in some embodiments, the human can produce antibodies that bind to, and inhibit, the ADAMTS13 metalloproteinase. In some embodiments of any of the methods described herein, the TTP can be a recurrent form. For example, the human can be one who has had TTP. In some embodiments of any of the methods described herein, the TTP (or recurrent TTP) is associated with a precipitating condition such as, but not limited to, a cancer, pregnancy, bacterial or viral infection, surgery, or any other TTP-associated condition known in the art or described herein. In some embodiments of any of the methods described herein, the TTP (or recurrent TTP) is associated with the use of a therapeutic agent associated with TTP. For example, the TTP can be associated with the use of, e.g., a platelet aggregation inhibitor such as ticlopidine or clopidogrel or an immunosuppressant (e.g., cyclosporine, mitomycin C, FK506, or interferon-alpha).

In some embodiments, any of the methods described herein can include identifying the human as one having, suspected of having, or at risk for developing, TTP. In some embodiments, any of the methods described herein can include, after the administering, monitoring the human for an improvement in one or more symptoms of TTP.

In some embodiments of any of the methods described herein, the composition can be administered to the human prior to, during, or following a plasma exchange, plasma infusion, plasmapheresis, or a splenectomy. In some embodiments, any of the methods described herein can include administering to the human one or more additional active agents useful for treating or preventing TTP. The one or more additional active agents can be selected from the group consisting of anti-hypertensives, steroids, anti-coagulants, or fibrinolytic agents.

In embodiments of any of the methods described herein where the complement-associated disorder is DDD, the DDD can be an inherited form of the disorder. For example, a human can have a DDD-associated mutation in the complement factor H gene, the complement factor H-related 5 gene, or the complement component C3 gene.

In some embodiments, any of the methods described herein can include identifying the human as one having, suspected of having, or at risk for developing, DDD. In some embodiments, any of the methods described herein can include, after the administering, monitoring the human for an improvement in one or more symptoms of DDD.

In some embodiments of any of the methods described herein, the composition can be administered to the human prior to, during, or following a plasma exchange, plasma replacement, plasmapheresis, or intravenous gamma globulin therapy. In some embodiments, any of the methods described herein can include administering to the human one or more additional active agents useful for treating DDD.

The one or more additional active agents can be selected from the group consisting of anti-hypertensives, corticosteroids, anti-coagulants, or fibrinolytic agents.

In embodiments of any of the methods described herein where the complement-associated disorder is MG, the human can be one expressing an MG-associated autoantibody such as, but not limited to, an MG-associated anti-AChR antibody, an MG-associated anti-MuSK antibody, or an MG-associated anti-striational protein antibody. The MG can be ocular MG and/or a drug-induced form of MG such as D-penicillamine-induced MG. In some embodiments, the human can be in, or be at risk for developing, myasthenic crisis. In some embodiments, the human can be a neonate having neonatal MG, wherein a mother with MG passes MG-associated antibodies through the placenta to an infant.

In some embodiments, any of the methods described herein can further include identifying the human as one having, suspected of having, or at risk for developing, MG. In some embodiments, any of the methods described herein can further include, after the administering, monitoring the human for an improvement in one or more symptoms of MG. In some embodiments of any of the methods described herein, the composition can be administered to the human prior to, during, or following a plasma exchange, plasmapheresis, IVIG, or immunoadsorption therapy.

In some embodiments, any of the methods described herein can include administering to the human one or more additional active agents useful for treating or preventing MG. The one or more additional active agents can be, e.g., acetylcholinesterase inhibitors, immunosuppressive agents, or any other additional active agents useful for treating MG that are known in the art or described herein.

In embodiments of any of the methods described herein where the complement-associated disorder is paroxysmal cold hemoglobinuria (PCH), the PCH can be associated with an infection (e.g., a viral or bacterial infection) or a neoplasm. For example, the PCH can be associated with a *Treponema* palladium infection, an influenza virus infection, a varicella-zoster virus infection, a cytomegalovirus (CMV) infection, an Epstein-Barr virus (EBV) infection, an adenovirus infection, a parvovirus B19 infection, a Coxsackie A9 infection, a *Haemophilus* influenza infection, a *Mycoplasma pneumoniae* infection, or a *Klebsiella pneumoniae* infection. In some embodiments, the PCH can be associated with non-Hodgkin's lymphoma. In some embodiments, the PCH can be associated with an immunization (e.g., a measles immunization). In some embodiments of any of the methods described herein, the PCH can be acute or recurrent.

In some embodiments, any of the methods described herein can include identifying the human as one having, suspected of having, or at risk for developing, PCH. In some embodiments, any of the methods described herein can include, after the administering, monitoring the human for an improvement in one or more symptoms of PCH.

In some embodiments of any of the methods described herein, the composition can be administered to the human prior to, during, or following a plasma exchange, plasma infusion, IVIG therapy, red cell transfusion, or plasmapheresis. In some embodiments, any of the methods described herein can include administering to the human one or more additional active agents useful for treating or preventing PCH. The one or more additional active agents can be selected from the group consisting of anti-hypertensives, steroids, immunosuppressives (e.g., rituximab), antibiotics, anti-viral agents, and chemotherapeutic agents.

In embodiments of any of the methods described herein where the complement-associated disorder is CAD, the CAD can be associated with an infection (e.g., a viral or bacterial infection) or a neoplasm. For example, the CAD can be associated with an HIV infection, a cytomegalovirus (CMV) infection, an Epstein-Barr virus (EBV) infection, or a *Mycoplasma pneumoniae* infection. In some embodiments, the CAD can be associated with non-Hodgkin's lymphoma. In some embodiments of any of the methods described herein, the CAD can be primary or secondary.

In some embodiments, any of the methods described herein can include identifying the human as one having, suspected of having, or at risk for developing, CAD. In some embodiments, any of the methods described herein can include, after the administering, monitoring the human for an improvement in one or more symptoms of CAD.

In some embodiments of any of the methods described herein, the composition can be administered to the human prior to, during, or following a plasma exchange, plasma replacement, IVIG therapy, or plasmapheresis. In some embodiments, any of the methods described herein can include administering to the human one or more additional active agents useful for treating or preventing CAD. The one or more additional active agents can be selected from the group consisting of anti-hypertensives, steroids, immunosuppressives (e.g., rituximab), antibiotics, anti-viral agents, and chemotherapeutic agents.

In embodiments of any of the methods described herein where the complement-associated disorder is HELLP syndrome, the affected woman can be pregnant or can be a woman who has recently been pregnant. For example, the woman can be one who has given birth less than 14 days (e.g., less than 13 days, 12 days, 11 days, 10 days, nine days, eight days, seven days, six days, five days, four days, three days, two days, 24 hours, 18 hours, 12 hours, 6 hours, or less than 4, 3, 2, or 1 hours) prior to administration. In some embodiments, the woman has been pregnant more than one time. In some embodiments, the woman can be one who has developed preeclampsia or HELLP syndrome during at least one prior pregnancy.

In embodiments where the complement-associated disorder is HELLP syndrome, the methods described herein can further include the step of identifying the woman as one having, suspected of having, or at risk for developing, HELLP syndrome. In some embodiments, any of the methods described herein can further include the step of, after the administering, monitoring the woman for an improvement in one or more symptoms of HELLP syndrome.

In some embodiments of any of the methods described herein, the composition can be administered to the woman prior to, during, or following a plasma exchange, plasmapheresis, platelet transfusion, or red blood cell transfusion.

In some embodiments, any of the methods described herein can include the step of administering to the woman at least one or more additional active agents useful for treating or preventing HELLP syndrome in a woman. The one or more additional active agents can be selected from the group consisting of an antihypertensive, a steroid, an anti-seizure agent, and an anti-thrombotic agent.

In yet another aspect, the disclosure features an article of manufacture, which includes (or consists of) a container with a label and a composition containing an inhibitor of human complement (e.g., an inhibitor of human complement component C5). The label indicates that the composition is to be administered to a human having, suspected of having, or at risk for developing, a complement-associated disorder such as any of the complement-associated disorders described herein. The inhibitor can be, e.g., an antibody or antigen-binding fragment thereof that binds to complement component C5 or a fragment thereof such as C5a or C5b. In some embodiments, the article of manufacture contains one or more additional active agents that are useful for treating or preventing a complement-associated disorder (e.g., ameliorating one or more symptoms of the disorder).

The disclosure is also based, in part, on the discovery by the inventors that upon treatment with the C5 inhibitor eculizumab, a patient with the complement-associated disorder aHUS and thrombotic microangiopathy (TMA) in the kidney experienced a complete resolution of the TMA in the kidney with no further development of TMA. Accordingly, in another aspect, the disclosure features a method for treating thrombotic microangiopathy (TMA), or reducing the occurrence or severity of TMA, in a patient who has, is suspected of having, or at risk of developing TMA. The method includes administering to the patient (being in need thereof) an inhibitor of complement such as an inhibitor of complement component C5 to thereby treat TMA in the patient. The inhibitor can be, e.g., any of the C5 inhibitors described herein, e.g., eculizumab. Administration of the C5 inhibitor can reduce the occurrence or severity of TMA in the brain and/or kidney of the patient. In some embodiments, administration of the C5 inhibitor treats or promotes the resolution of pre-existing TMA in the patient, e.g., a pre-existing TMA in the brain or kidney of the patient.

In some embodiments, the patient has a complement associated-disorder such as any of those described herein, e.g., membranoproliferative glomerulonephritis, Degos disease, atypical hemolytic uremic syndrome, antibody-mediated rejection, HELLP syndrome, or catastrophic antiphospholipid syndrome.

The inventors have also discovered that administration of eculizumab to patients with, e.g., aHUS or CAPS results in an unexpectedly rapid amelioration of one or more symptoms of the diseases. For example, the inventors have discovered that hypertension, reduced urine output, and low platelet levels are ameliorated in eculizumab-treated aHUS patients in less than one month (e.g., less than two weeks) from initiating chronic treatment with eculizumab. In another example, the inventors discovered that the proteinuria in a patient with membranoproliferative glomerulonephritis was ameliorated within a month following initiation of chronic treatment with eculizumab. Accordingly, in yet another aspect, the disclosure features a method for ameliorating one or more symptoms associated with a complement-associated disorder such as any of the complement-associated disorders described herein with the exception of paroxysmal nocturnal hemoglobinuria. The method includes administering to a patient in need thereof an inhibitor of complement (e.g., an inhibitor of complement component C5) in an amount effective to ameliorate one or more symptoms associated a complement-associated disorder, wherein the symptoms are ameliorated within less than two months (e.g., less than 7, 6, 5, 4, 3, or 2 weeks; less than 20, 19, 18, 17, 16, 15, 14, 13, 12, 11, 10, 9, 8, 7, 6, 5, 4, 3, 2, or 1 day(s); or less than 12, 11, 10, 9, 8, 7, 6 or even less than 5 hours) after administering the inhibitor. Symptoms of complement-associated disorders are well known in the art of medicine and described herein. The complement inhibitor can be any of the C5 inhibitors described herein, e.g., eculizumab. Exemplary symptoms that may be ameliorated by the C5 inhibitor in less than 2 months include, e.g., proteinuria, hypertension, reduced platelet counts, and reduced urine output from the kidney. In some embodiments, at least one of the symptoms is ameliorated to within 40 (e.g., 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or even 1) % of its normal level or value. For example, in some embodiments, administration of the C5 inhibitor eculizumab to a hypertensive patient with aHUS can ameliorate the patient's hypertension to within 40% of the normal blood pressure (diastolic and/or systolic) for the patient. In some embodiments, administration of the C5 inhibitor can completely ameliorate one or more symptoms of the complement-associated disorder in the subject. In some embodiments, the patient has had a kidney transplant, e.g., an aHUS patient who has recently undergone a kidney transplant. The complement associated-disorder can be any of those described herein, e.g., membranoproliferative glomerulonephritis, Degos disease, atypical hemolytic uremic syndrome, antibody-mediated rejection, HELLP syndrome, and catastrophic antiphospholipid syndrome.

Many of the complement-associated disorders described herein are characterized by episodic or sporadic symptom presentation and historically have only been treated when symptoms manifest. However, the inventors have discovered that an underlying complement-associated disorder remains present even when the patients are asymptomatic. The inventors have also discovered that recurrences or relapses of the disorders can be prevented or at least minimized by chronic treatment using a complement-mediated inhibitor. Such chronic administration of the inhibitor is useful to prevent or minimize the often irreversible damage (e.g., loss of an organ such as a kidney) inflicted upon patients with severe complement-related disorders (e.g., aHUS or CAPS) when the relapses occur. Accordingly, it is of the utmost importance to administer a complement inhibitor to the patient in an amount and with a frequency sufficient to continually maintain a concentration of the inhibitor that is high enough to prevent or substantially inhibit systemic complement activity in the patients.

Thus, in another aspect, the disclosure features a method for treating a complement-associated disorder, which method includes chronically administering to a patient in need thereof a complement inhibitor (e.g., a C5 inhibitor such as an anti-C5 antibody) in an amount and with a frequency that are effective to maintain systemic complement inhibition in the patients with the proviso that the complement-associated disorder is not paroxysmal nocturnal hemoglobinuria.

As used herein, "chronically administered," "chronic treatment," "treating chronically," or similar grammatical variations thereof refer to a treatment regimen that is employed to maintain a certain threshold concentration of a therapeutic agent in the blood of a patient in order to completely or substantially suppress systemic complement activity in the patient over a prolonged period of time. Accordingly, a patient chronically treated with a complement inhibitor can be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) with the inhibitor in an amount and with a dosing frequency that are sufficient to maintain a concentration of the inhibitor in the patient's blood that inhibits or substantially inhibits systemic complement activity in the patient. In some embodiments, the complement inhibitor can be chronically administered to a patient in need thereof in an amount and with a frequency that are effective to maintain serum hemolytic activity at less than or equal to 20 (e.g., 19, 18, 17, 16, 15, 14, 13, 12, 11, 10, 9, 8, 7, 6, or even below 5) % and to maintain serum hemolytic activity at less than or equal to 20%. See, e.g., Hill et al. (2005) *Blood* 106(7):2559. In some embodiments, the complement inhibitor can be administered to a patient in an amount and with a frequency that are effective to maintain serum lactate dehydrogenase (LDH) levels at within at least 20 (e.g., 19, 18, 17, 16, 15, 14, 13, 12, 11, 10, 9, 8, 7, 6, or even below 5) % of the normal range for LDH. See Hill et al. (2005) supra. In some embodiments, the complement inhibitor is administered to the patient in an amount and with a frequency that are effective to maintain a serum LDH level less than 550 (e.g., less than 540, 530, 520, 510, 500, 490, 480, 470, 460, 450, 430, 420, 410, 400, 390, 380, 370, 360, 350, 340, 330, 320, 310, 300, 290, 280, or less than 270) IU/L. To maintain systemic complement inhibition in a patient, the complement inhibitor can be chronically administered to the patient, e.g., once a week, once every two weeks, twice a week, once a day, once a month, or once every three weeks. In some embodiments of any of the methods described herein, a C5 inhibitor (e.g., an anti-C5 antibody) can be administered to a patient in an amount and with a frequency of administration effective to maintain a concentration of at least 0.7 (e.g., at least 0.8, 0.9, one, two, three, four, five, six, seven, eight, nine, or 10 or more) divalent C5 inhibitor molecule(s) (e.g., a whole anti-C5 antibody such as eculizumab) per every C5 molecule in the patient's blood. "Divalent" or "bivalent," with respect to a C5 inhibitor, refers to a C5 inhibitor that contains at least two binding sites for a C5 molecule. Where the C5 inhibitor is monovalent (e.g., a single chain anti-C5 antibody or a Fab that binds to C5), the inhibitor can be administered to the patient in an amount and with a frequency that are effective to maintain a concentration of at least 1.5 (e.g., at least 2, 2.5, 3, 3.5, 4, 4.5, or 5 or more) of the monovalent C5 inhibitors per every C5 molecule in the blood. In some embodiments, the monovalent C5 inhibitor can be administered to the patient in an amount and with a frequency that are effective to maintain a ratio of monovalent C5 inhibitor to C5 of at least 2:1 (e.g., at least 3:1, at least 4:1, at least 5:1, or at least 6:1 or more). In some embodiments of any of the methods described herein, a whole (bivalent) anti-C5 antibody is administered to the patient in an amount and with a frequency that are effective to maintain a concentration of at least 40 (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 110, or 120 or more) µg of the antibody per milliliter of the patient's blood. In preferred embodiments, a whole anti-C5 antibody (e.g., eculizumab) is administered in an amount and with a frequency to maintain the antibody at a concentration of at least 50 µg per milliliter of the patient's blood. In preferred embodiments, a whole anti-C5 antibody (e.g., eculizumab) is administered in an amount and with a frequency to maintain the antibody at a concentration of at least 100 µg per milliliter of the patient's blood. In some embodiments of any of the methods described herein, a monovalent anti-C5 antibody (e.g., a single chain antibody or an Fab fragment) can be administered to the patient in an amount and with a frequency that are effective to maintain a concentration of at least 80 (e.g., 81, 82, 83, 84, 85, 86, 87, 88, 89, 90, 91, 92, 93, 94, 95, 96, 97, 98, 99, 100, 110, 115, 120, 125, 130, 135, 140, 145, 150, 155, 160, 165, or a 170 or more) µg of the antibody per milliliter of the patient's blood. Exemplary chronic dosing strategies are described herein.

In another aspect, the disclosure features a method for treating a complement-associated disorder, which method includes chronically administering to a patient in need thereof an anti-C5 antibody in an amount and with a frequency that are effective to maintain systemic complement inhibition in the patients. In some embodiments, the anti-C5 antibody can be chronically administered to a patient in need thereof in an amount and with a frequency that are effective to maintain serum hemolytic activity at less than or equal to 20 (e.g., 19, 18, 17, 16, 15, 14, 13, 12, 11, 10, 9, 8, 7, 6, or even below 5) % and to maintain the serum hemolytic activity at less than or equal to 20%. See, e.g., Hill et al. (2005) *Blood* 106(7):2559. In some embodiments, the anti-C5 antibody can be administered to a patient in an amount and with a frequency that are effective to maintain serum lactate dehydrogenase (LDH) levels at within: at least 20 (e.g., 19, 18, 17, 16, 15, 14, 13, 12, 11, 10, 9, 8, 7, 6, or even below 5) % of the normal range for LDH; or less than or equal to 550 (e.g., less than or equal to 550, 540, 530, 520, 510, 500, 490, 480, 470, 460, 450, 430, 420, 410, 400, 390, 380, 370, 360, 350, 340, 330, 320, 310, 300, 290, 280, or less than 270) IU/L. See, e.g., Hill et al. (2005) supra. In some embodiments, the anti-C5 antibody is administered to the patient in an amount and with a frequency to maintain a concentration of at least 0.7 (e.g., at least 0.8, 0.9, 1, 2, 3, or 4 or more) whole (bivalent) anti-C5 antibody molecule(s) per every C5 molecule in the patient's blood. In some embodiments, the anti-C5 antibody can be administered to the patient in an amount and with a frequency that are effective to maintain a ratio of whole (bivalent) anti-C5 antibody to C5 in the blood of at least 1:1 (e.g., at least 3:2, 2:1, 5:2, or 3:1). Where the anti-C5 antibody is monovalent, the anti-C5 antibody can be administered to the patient in an amount and with a frequency that are effective to maintain a concentration of at least 2 of the monovalent anti-C5 antibodies per every C5 molecule in the blood. In some embodiments, the monovalent anti-C5 antibody can be administered to the patient in an amount and with a frequency that are effective to maintain a ratio of monovalent anti-C5 antibody to C5 of at least 2:1 (e.g., at least 3:1, at least 4:1, at least 5:1, or 6:1 or more). The anti-C5 antibody can be, e.g., eculizumab. The patient can have, be suspected of having, or be at risk for developing a complement-associated disorder with the proviso that the disorder is not paroxysmal nocturnal hemoglobinuria. For example, the complement-associated disorder can be one selected from the group consisting of membranoproliferative glomerulonephritis, Degos disease, atypical hemolytic uremic syndrome, antibody-mediated rejection, HELLP syndrome, and catastrophic antiphospholipid syndrome.

In some embodiments of any of the methods described herein, an anti-C5 antibody can be administered chronically to a patient based on his or her weight. In some embodiments of any of the methods described herein, an anti-C5 antibody (e.g., eculizumab) can be administered chronically to a patient based on his or her weight and under the dosing schedule set forth in Table 1.

TABLE 1

Exemplary Chronic Dosing Schedules for a Whole Anti-C5 Antibody (e.g., eculizumab) by Patient Weight

| Patient Weight | Induction/Loading Dosing | Maintenance Dosing (A) | (B) |
|---|---|---|---|
| Adults of any weight or any | At least 800 (e.g., at least 810, 820, 830, 840, 850, 860, 870, 880, | At least 800 (e.g., at least 810, 820, 830, 840, 850, 860, | Following the (A) dose, at least 800 (e.g., at least 810, 820, 830, 840, 850, |

TABLE 1-continued

Exemplary Chronic Dosing Schedules for a Whole Anti-C5 Antibody (e.g., eculizumab) by Patient Weight

| Patient Weight | Induction/Loading Dosing | Maintenance Dosing (A) | (B) |
|---|---|---|---|
| patient with a body weight that is greater than or equal to 40 kg | 890, 900, 910, 920, 930, 940, 950, 960, 970, 980, 990, 1000, 1100, or 1200 or more) mg once a week for four weeks | 870, 880, 890, 900, 910, 920, 930, 940, 950, 960, 970, 980, 990, 1000, 1050, 1100, 1150, 1200, 1250, 1300, 1350, or 1400 or more) mg on week five | 860, 870, 880, 890, 900, 910, 920, 930, 940, 950, 960, 970, 980, 990, 1000, 1050, 1100, 1150, 1200, 1250, 1300, 1350, or 1400 or more) mg once every two weeks thereafter* |
| Body weight that is less than 40 kg, but greater than or equal to 30 kg | At least 500 (e.g., at least 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or 850 or more) mg once a week for two weeks | At least 800 (e.g., at least 810, 820, 830, 840, 850, 860, 870, 880, 890, 900, 910, 920, 930, 940, 950, 960, 970, 980, 990, 1000, 1050, 1100, 1150, 1200, 1250, 1300, 1350, or 1400 or more) mg on week three | Following the (A) dose, at least 800 (e.g., at least 810, 820, 830, 840, 850, 860, 870, 880, 890, 900, 910, 920, 930, 940, 950, 960, 970, 980, 990, 1000, 1050, 1100, 1150, 1200, 1250, 1300, 1350, or 1400 or more) mg once every two weeks thereafter* |
| Body weight that is less than 30 kg, but greater than or equal to 20 kg | At least 500 (e.g., at least 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or 850 or more) mg once a week for two weeks | At least 500 (e.g., at least 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or 850 or more) mg on week three | Following the (A) dose, at least 500 (e.g., at least 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or 850 or more) mg once every two weeks thereafter* |
| Body weight that is less than 20 kg, but greater than or equal to 10 kg | At least 500 (e.g., at least 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or 850 or more) mg once a week for one week | At least 200 (e.g., at least 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or 550 or more) mg on week two | Following the (A) dose, at least 200 (e.g., at least 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or 550 or more) mg once every two weeks thereafter* |
| Body weight that is less than 10 kg, but greater than or equal to 5 kg | At least 200 (e.g., at least 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or 550 or more) mg once a week for one week | At least 200 (e.g., at least 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or 550 or more) mg on week two | Following the (A) dose, at least 200 (e.g., at least 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or 550 or more) mg once every three weeks thereafter* |

*In accordance with the present disclosure, the (B) maintenance dosing schedule can be maintained for the duration of the treatment regimen, e.g., at least one (e.g., at least two, three, four, five, six, seven, eight, nine, 10, 11, 12, 13, 14, 15, 16, 17, 18, 19, 20, 22, 24, 36, or 48 or more) month(s); at least one (e.g., at least two, three, four, five, six, seven, eight, nine, 10, 11, 12, 13, 14, or 15 or more) years; or for the remainder of the patient's life.

In preferred embodiments, an anti-C5 antibody (e.g., eculizumab) can be administered to a patient based on his or her weight under the dosing schedules set forth in Table 2.

TABLE 2

Exemplary Chronic Dosing Schedules for a Whole Anti-C5 Antibody (e.g., eculizumab) by Patient Weight

| Patient Weight | Induction/Loading Dosing | Maintenance Dosing (A) | (B) |
|---|---|---|---|
| Adults of any weight or any patient with a body weight that is greater than or equal to 40 kg | At least 900 (e.g., at least 910, 920, 930, 940, 950, 960, 970, 980, 990, 1000, 1100, or 1200 or more) mg once a week for four weeks | At least 1200 (e.g., at least 1225, 1250, 1300, 1350, or 1400 or more) mg on week five | Following the (A) dose, at least 1200 (e.g., at least 1225, 1250, 1300, 1350, or 1400 or more) mg once every two weeks thereafter* |
| Body weight that is less than 40 kg, but greater than or equal to 30 kg | At least 600 (e.g., at least 610, 620, 630, 640, 650, 660, 670, 680, 690, 700, 710, 720, 730, 740, 750, 760, 770, 780, 790, 800, or 850 or more) mg once a week for two weeks | At least 900 (e.g., at least 910, 920, 930, 940, 950, 960, 970, 980, 990, 1000, 1050, 1100, 1150, or 1200 or more) mg on week three | Following the (A) dose, at least 900 (e.g., at least 910, 920, 930, 940, 950, 960, 970, 980, 990, 1000, 1050, 1100, 1150, or 1200 or more) mg once every two weeks thereafter* |
| Body weight that is less than 30 kg, but greater than or equal to 20 kg | At least 600 (e.g., at least 610, 620, 630, 640, 650, 660, 670, 680, 690, 700, 710, 720, 730, 740, 750, 760, 770, 780, 790, 800, or 850 or more) mg once a week for two weeks | At least 600 (e.g., at least 610, 620, 630, 640, 650, 660, 670, 680, 690, 700, 710, 720, 730, 740, 750, 760, 770, 780, 790, 800, or 850 or more) mg on week three | Following the (A) dose, at least 600 (e.g., at least 610, 620, 630, 640, 650, 660, 670, 680, 690, 700, 710, 720, 730, 740, 750, 760, 770, 780, 790, 800, or 850 or more) mg once every two weeks thereafter* |
| Body weight that is less than 20 kg, but | At least 600 (e.g., at least 610, 620, 630, 640, 650, 660, 670, 680, 690, 700, 710, 720, 730, 740, 750, 760, | At least 300 (e.g., at least 310, 320, 330, 340, 350, 360, 370, 380, 390, 400, 410, 420, 430, 440, 450, | Following the (A) dose, at least 310 (e.g., at least 320, 330, 340, 350, 360, 370, 380, 390, 400, 410, 420, 430, 440, 450, 460, 470, |

TABLE 2-continued

Exemplary Chronic Dosing Schedules for a Whole Anti-C5 Antibody (e.g., eculizumab) by Patient Weight

| Patient Weight | Induction/Loading Dosing | Maintenance Dosing (A) | Maintenance Dosing (B) |
|---|---|---|---|
| greater than or equal to 10 kg | 770, 780, 790, 800, or 850 or more) mg once a week for one week | 460, 470, 480, 490, 500, or 550 or more) mg on week two | 480, 490, 500, or 550 or more) mg once every two weeks thereafter* |
| Body weight that is less than 10 kg, but greater than or equal to 5 kg | At least 300 (e.g., at least 310, 320, 330, 340, 350, 360, 370, 380, 390, 400, 410, 420, 430, 440, 450, 460, 470, 480, 490, 500, or 550 or more) mg once a week for one week | At least 300 (e.g., at least 310, 320, 330, 340, 350, 360, 370, 380, 390, 400, 410, 420, 430, 440, 450, 460, 470, 480, 490, 500, or 550 or more) mg on week two | Following the (A) dose, at least 300 (e.g., at least 310, 320, 330, 340, 350, 360, 370, 380, 390, 400, 410, 420, 430, 440, 450, 460, 470, 480, 490, 500, or 550 or more) mg once every three weeks thereafter* |

*In accordance with the present disclosure, the (B) maintenance dosing schedule can be maintained for the duration of the treatment regimen, e.g., at least one (e.g., at least two, three, four, five, six, seven, eight, nine, 10, 11, 12, 13, 14, 15, 16, 17, 18, 19, 20, 22, 24, 36, or 48 or more) month(s); at least one (e.g., at least two, three, four, five, six, seven, eight, nine, 10, 11, 12, 13, 14, or 15 or more) years; or for the remainder of the patient's life.

It is understood that the exemplary dosing schedules in Tables 1 or 2 can be adjusted (in frequency, duration, and/or in total amount of antibody administered) by a medical practitioner as necessary in such a way as to maintain complete or substantially complete inhibition of systemic complement activity in the patient for the duration of the dosing regime.

In another aspect, the disclosure features a method for treating a complement-associated disorder, the method including chronically administering to a patient in need thereof an anti-C5 antibody in an amount and with a frequency that are effective to maintain a concentration of at least 40 (e.g., at least 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 110, or 120 or more) μg of the antibody per milliliter of the patient's blood, wherein the patient has, is suspected of having, or is at risk for developing a complement-associated disorder with the proviso that the disorder is not paroxysmal nocturnal hemoglobinuria.

In some embodiments, the anti-C5 antibody is administered to the patient at least once every two weeks. In some embodiments, the anti-C5 antibody is administered to the patient once per week. In some embodiments, the anti-C5 antibody is administered to the patient for at least 9 weeks (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) under the following dosing schedule: at least 800 (e.g., at least 810, 820, 830, 840, 850, 860, 870, 880, 890, 900, 910, 920, 930, 940, 950, 960, 970, 980, 990, 1000, 1100, or 1200 or more) mg of the anti-C5 antibody, once per week for four consecutive weeks; at least 800 (e.g., at least 810, 820, 830, 840, 850, 860, 870, 880, 890, 900, 910, 920, 930, 940, 950, 960, 970, 980, 990, 1000, 1100, or 1200 or more) mg of the anti-C5 antibody once during the fifth week; and at least 800 (e.g., at least 810, 820, 830, 840, 850, 860, 870, 880, 890, 900, 910, 920, 930, 940, 950, 960, 970, 980, 990, 1000, 1100, or 1200 or more) mg of the anti-C5 antibody bi-weekly thereafter for the remainder of the dosing schedule. In preferred embodiments, at least 900 mg of the anti-C5 antibody is administered to the patient, once per week for four weeks; at least 1200 mg is administered to the patient during the fifth week; and at least 1200 mg of the anti-C5 antibody is administered to the patient bi-weekly thereafter for the remainder of the chronic dosing schedule.

In yet another aspect, the disclosure features a method for transplanting an organ or tissue. The method includes transplanting an organ or tissue into a patient in need thereof, wherein prior to and chronically following the transplanting an inhibitor of human complement is administered to the patient in an amount and with a frequency effective to substantially inhibit systemic complement activity in the patient. The complement inhibitor can be, e.g., a C5 inhibitor such as an anti-C5 antibody (e.g., eculizumab). As described herein, the C5 inhibitor (e.g., the anti-C5 antibody) can be administered in an amount and with a frequency to maintain a concentration of at least 0.7 bivalent C5 inhibitor molecule(s) (or at least 1.5 monovalent C5 inhibitor molecule(s)) per every C5 molecule in the patient's blood. In some embodiments, the C5 inhibitor (e.g., the anti-C5 antibody) can be administered to the patient in an amount and with a frequency to maintain a concentration of at least at least 40 (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 110, or 120 or more) μg of the inhibitor (e.g., the anti-C5 antibody) in the patient's blood. In some embodiments, at least 800 (e.g., at least 810, 820, 830, 840, 850, 860, 870, 880, 890, 900, 910, 920, 930, 940, 950, 960, 970, 980, 990, 1000, 1100, or 1200 or more) mg of the anti-C5 antibody (e.g., eculizumab) is administered to the patient less than 24 (e.g., less than 23, 22, 21, 20, 19, 18, 17, 16, 15, 14, 13, 12, 11, 10, 9, 8, 7, 6, 5, 4, 3, or less than 2) hours prior to transplanting the organ or tissue to the patient. In some embodiments, the methods can also include, prior to the transplanting, contacting (e.g., soaking) the organ or tissue with a C5 inhibitor (e.g., an anti-C5 antibody such as eculizumab) for an amount of time and under conditions that inhibit complement activation in the organ or tissue upon transplantation. The organ can be, e.g., skin, a kidney, heart, lung, limb (e.g., finger or toe), eye, stem cell population, bone marrow, vascular tissue, muscle, nervous tissue, or liver. The patient can have, be at risk for developing, or be suspected of having aHUS. In some embodiments, at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of an anti-C5 antibody is administered to the patient less than 24 (e.g., less than 23, 22, 21, 20, 19, 18, 17, 16, 15, 14, 13, 12, 11, 10, 9, 8, 7, 6, 5, 4, 3, or less than 2) hours following the transplanting. In some embodiments, the anti-C5 antibody is chronically administered to the patient following the transplanting. For example, an anti-C5 antibody can be chronically administered to the patient for at least 9 weeks (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) under the following dosing schedule: at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody less than 24 hours after transplanting the organ or tissue; at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody once per week for four weeks after the initial post-transplant dose; at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody once during the fifth week; and at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody bi-weekly thereafter for the remainder of the dosing schedule. In preferred embodiments, an anti-C5 antibody is administered to a patient undergoing a transplant operation under the following dosing schedule: at least 1200 mg of the anti-C5 antibody is administered to the patient less than 24 hours prior to the transplanting; at least 900 mg of the anti-C5 antibody is administered to the patient within 24 hours after the transplanting; at least 1200 mg of the anti-C5 antibody is administered to the patient once a week for four weeks following the first post-operation administration of the anti-C5 antibody; 1200 mg administered to the patient on the fifth week following the first post-operation administration of the anti-C5 antibody; and at least 1200 mg of the anti-C5 antibody administered to the patient bi-weekly thereafter for the remainder of the chronic treatment regimen.

In some embodiments, the methods can further include administering to the patient one or more immunosuppressive agents such as, but not limited to, rapamycin, cyclosporine A, an anti-IL-2 agent, OKT3, and tacrolimus. The one or more immunosuppressive agents can be administered prior to, during, or following the transplanting. The one or more immunosuppressive agents can also be administered before, concurrently with, or following administration of the C5 inhibitor.

The disclosure also features a method for reducing complement-mediated injury to an organ or a tissue when transplanted into a patient. The method includes, prior to transplanting an organ or tissue to a patient in need thereof, contacting the organ or tissue with a pharmaceutical solution comprising an inhibitor of C5 for a period of time and under conditions which reduce complement-mediated injury to the organ or tissue when transplanted into the patient. The C5 inhibitor can also be administered to the patient prior to, during, and/or after the transplanting of the organ or tissue. The solution can also contain one or more immunosuppressive agents such as, but not limited to, rapamycin, cyclosporine A, an anti-IL-2 agent, OKT3, and tacrolimus.

The inventors have also discovered that in patients who have had severe complement-associated disorders such as CAPS and APS and entered remission, there still remains in the patients a low level of complement activity that predisposes the patients for relapse or recurrence. As noted above, recurrence of symptoms in patients who have had these severe disorders can present immediate and sometimes irreversible injury to major organs such as the kidney. Thus, while the disclosure is in no way limited by one particular theory or mechanism of action, the inventors assert that in order to prevent sudden relapse or recurrence, a patient with a complement-associated disorder (e.g., aHUS and CAPS) should be chronically treated with a C5 inhibitor even after one or more symptoms of the disorder have been ameliorated and/or even after the patient enters a clinical remission. Thus, in yet another aspect, the disclosure features a method for treating a complement-associated disorder with the proviso that the disorder is not paroxysmal nocturnal hemoglobinuria. The method includes administering to a patient afflicted with a complement-associated disorder a C5 inhibitor (e.g., an anti-C5 antibody such as eculizumab) in an amount effective to treat the complement-associated disorder. The C5 inhibitor is administered to the patient even after one or more (e.g., two, three, four, five, or six or more) symptoms of the disorder have been ameliorated. In some embodiments, the C5 inhibitor is administered to the patient even after one or more symptoms have been completely ameliorated. In some embodiments, the C5-inhibitor is administered to the patient even after the patient has entered clinical remission. The C5 inhibitor can be administered, e.g., chronically administered, to the patient for at least 8 weeks (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) after one or more symptoms have been ameliorated in the patient and/or the patient enters clinical remission. The complement-associated disorder can be any of those described herein, e.g., membranoproliferative glomerulonephritis, Degos disease, atypical hemolytic uremic syndrome, antibody-mediated rejection, HELLP syndrome, and catastrophic antiphospholipid syndrome.

While the disclosure is in no way limited by a particular theory or mechanism of action, based on the observations of the effect of eculizumab in, e.g., aHUS patients, the inventors have concluded that the biological activity of complement component C5a may substantially contribute to the vasoconstriction and hypertension associated with aHUS. Accordingly, inhibition of C5a using a C5a inhibitor is useful for treating aHUS and/or ameliorating the vasoconstriction and hypertension associated with aHUS. The method includes administering to a patient in need thereof an inhibitor of complement component C5a in an amount effective to treat aHUS in the patient. In some embodiments, the vasoconstriction and hypertension associated with aHUS can be ameliorated within less than two months (e.g., less than 7, 6, 5, 4, 3, or 2 weeks; less than 14, 13, 12, 11, 10, 9, 8, 7, 6, 5, 4, 3, 2, or 1 day(s); or less than 12, 11, 10, 9, 8, 7, 6 or even less than 5 hours) after administering the C5a inhibitor. In some embodiments, the C5a inhibitor is an antibody (or antigen-binding fragment thereof) that binds to a human C5a protein or a fragment thereof having an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:12-25. In some embodiments, the inhibitor is an antibody that binds to human C5a protein having the amino acid sequence depicted in SEQ ID NO:12. The C5a inhibitor does not inhibit the cleavage of C5 into fragment C5a and C5b. The C5a inhibitor also does not inhibit C5b or the formation of the membrane attack complex. As described herein, in some embodiments, the C5a inhibitor (e.g., an anti-C5a antibody) can inhibit the interaction between C5a and a C5a receptor (e.g., C5aR or C5L2). In some embodiments, the antibody can be a monoclonal antibody, a single-chain antibody, a humanized antibody, a fully human antibody, a polyclonal antibody, a recombinant antibody, a diabody, a chimerized or chimeric antibody, a deimmunized human antibody, a fully human antibody, a single chain antibody, an Fv fragment, an Fd fragment, an Fab fragment, an Fab' fragment, or an F(ab')$_2$ fragment.

In embodiments of any of the methods described herein where the complement-associated disorder is aHUS, the aHUS can be genetic, acquired, or idiopathic form. In some embodiments, the aHUS can be complement factor H (CFH)-associated aHUS (e.g., aHUS associated with mutations in factor H or autoantibodies that bind to and inactivate factor H), membrane cofactor protein (MCP)-associated aHUS, complement factor I (CFI)-associated aHUS, C4b-binding protein (C4BP)-associated aHUS, complement factor B-(CFB)-associated aHUS, a vWF disorder, or aHUS associated with any other mutations in the alternative pathway of complement activation causing low levels of C3 as a result of increased C3 consumption.

In some embodiments, any of the methods described herein can further include identifying the patient as one having, suspected of having, or at risk for developing, aHUS. In some embodiments, any of the methods described herein can include, after the administering, monitoring the patient for an improvement in one or more symptoms of aHUS. In some embodiments of any of the methods described herein, the C5a inhibitor can be administered to the patient prior to, during, or following a plasma therapy (e.g., plasma exchange or plasma infusion). In some embodiments, administration of the C5a inhibitor to the patient can alleviate the need for plasma therapy by a patient. For example, in some embodiments, administration (e.g., chronic administration) of the C5a inhibitor to the patient can alleviate or substantially reduce the need for plasma therapy by a patient for at least 2 months (e.g., 3 months, 4 months, 5 months, 6 months, 7 months, 8 months, 9 months, 10 months, 11 months, or 12 months or 1, 2, 3, 4, 5, or 6 years or more). In some embodiments, any of the methods described herein can include administering to the patient one or more additional active agents useful for treating typical HUS or aHUS. The one or more additional active agents can be, e.g., selected from the group consisting of anti-hypertensives, anti-platelet agents, prostacyclin, fibrinolytic agents, and anti-oxidants.

In some embodiments, the human is an infant. The infant can be, e.g., 0.5 (e.g., 1, 1.5, 2, 2.5, 3, 3.5, 4, 4.5, 5, 5.5, 6, 6.5, 7, 7.5, 8, 8.5, 9, or 9.5) years old. The infant can be less than 10 (e.g., less than 9.5, 9, 8.5, 8, 7.5, 7, 6.5, 6, 5.5, 5, 4.5, 4, 3.5, 3, 2.5, 2, 1.5, 1, or less than 1) year(s) old.

In some embodiments of any of the methods described herein, the complement-associated disorder is not paroxysmal nocturnal hemoglobinuria.

"Polypeptide," "peptide," and "protein" are used interchangeably and mean any peptide-linked chain of amino acids, regardless of length or post-translational modification. The complement component C5 proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The human complement component C5 proteins described herein also include "antigenic peptide fragments" of the proteins, which are shorter than full-length and/or immature (pre-pro) C5 proteins, but retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal (see below under "Methods for Producing an Antibody"). Antigenic peptide fragments of a C5 protein include terminal as well internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Antigenic peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or 600 or more) amino acid residues in length (e.g., at least 6 contiguous amino acid residues in any one of SEQ ID NOS:1-11). In some embodiments, an antigenic peptide fragment of a human C5 protein has fewer than 500 (e.g., fewer than 450, 400, 350, 325, 300, 275, 250, 225, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6) amino acid residues in length (e.g., fewer than 500 contiguous amino acid residues in any one of SEQ ID NOS:1-11). In some embodiments, an antigenic peptide fragment of a full-length, immature human C5 protein (prepro-C5 protein) has at least 6, but fewer than 500, amino acid residues in length.

In some embodiments, the human complement component C5 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human C5 protein having the amino acid sequence depicted in SEQ ID NO:1 (see below).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Amino acid sequences for exemplary human C5 proteins as well as antigenic peptide fragments thereof are known in the art and are set forth below.

As used throughout the present disclosure, the term "antibody" refers to a whole or intact antibody (e.g., IgM, IgG, IgA, IgD, or IgE) molecule that is generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to fragment of an antibody that retains the ability to bind to an antigen (e.g., a complement component C5 protein), e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, diabodies (Poljak (1994) *Structure* 2(12):1121-1123; Hudson et al. (1999) *J Immunol. Methods* 23(1-2):177-189, the disclosures of each of which are incorporated herein by reference in their entirety) and intrabodies (Huston et al. (2001) *Hum. Antibodies* 10(3-4):127-142; Wheeler et al. (2003) *Mol Ther* 8(3):355-366; Stocks (2004) *Drug Discov. Today* 9(22): 960-966, the disclosures of each of which are incorporated herein by reference in their entirety) that bind to a complement component C5 protein can be incorporated into the compositions, and used in the methods, described herein.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating or preventing a complement-associated disorder, will be apparent from the following description, the examples, and from the claims.

DETAILED DESCRIPTION

The present disclosure provides compositions containing an inhibitor of human complement component C5 (e.g., an antibody that binds to a human complement component C5 protein or a biologically-active fragment thereof such as C5a and C5b) and methods for using the compositions to treat or prevent a complement-mediated disorder in a human. While in no way intended to be limiting, exemplary compositions (e.g., pharmaceutical compositions and formulations) and methods for using the compositions are elaborated on below.

Compositions

The compositions described herein contain an inhibitor of human complement. Any compound which binds to or otherwise blocks the generation and/or activity of any of the human complement components may be utilized in accordance with the present disclosure. For example, an inhibitor of complement can be, e.g., a small molecule, a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, a complement inhibitor may be a protein or protein fragment.

In some embodiments, the compositions contain antibodies specific to a human complement component. Some compounds include antibodies directed against complement components C1, C2, C3, C4, C5 (or a fragment thereof; see below), C6, C7, C8, C9, Factor D, Factor B, Factor P, MBL, MASP-1, and MASP-2, thus preventing the generation of the anaphylatoxic activity associated with C5a and/or preventing the assembly of the membrane attack complex associated with C5b.

The compositions can also contain naturally occurring or soluble forms of complement inhibitory compounds such as CR1, LEX-CR1, MCP, DAF, CD59, Factor H, cobra venom factor, FUT-175, complestatin, and K76 COOH. Other compounds which may be utilized to bind to or otherwise block the generation and/or activity of any of the human complement components include, but are not limited to, proteins, protein fragments, peptides, small molecules, RNA aptamers including ARC 187 (which is commercially available from Archemix Corporation, Cambridge, Mass.), L-RNA aptamers, spiegelmers, antisense compounds, serine protease inhibitors, molecules which may be utilized in RNA interference (RNAi) such as double stranded RNA including small interfering RNA (siRNA), locked nucleic acid (LNA) inhibitors, peptide nucleic acid (PNA) inhibitors, etc.

In some embodiments, the complement inhibitor inhibits the activation of complement. For example, the complement inhibitor can bind to and inhibit the complement activation activity of C1 (e.g., C1q, C1r, or C1s) or the complement inhibitor can bind to and inhibit (e.g., inhibit cleavage of) C2, C3, or C4. In some embodiments, the inhibitor inhibits formation or assembly of the C3 convertase and/or C5 convertase of the alternative and/or classical pathways of complement. In some embodiments, the complement inhibitor inhibits terminal complement formation, e.g., formation of the C5b-9 membrane attack complex. For example, an antibody complement inhibitor may include an anti-C5 antibody. Such anti-C5 antibodies may directly interact with C5 and/or C5b, so as to inhibit the formation of and/or physiologic function of C5b.

In some embodiments, the compositions described herein can contain an inhibitor of human complement component C5 (e.g., an antibody, or antigen-binding fragment thereof, that binds to a human complement component C5 protein or a biologically-active fragment thereof such as C5a or C5b). As used herein, an "inhibitor of complement component C5" is any agent that inhibits: (i) the expression, or proper intracellular trafficking or secretion by a cell, of a complement component C5 protein; (ii) the activity of C5 cleavage fragments C5a or C5b (e.g., the binding of C5a to its cognate cellular receptors or the binding of C5b to C6 and/or other components of the terminal complement complex; see above); (iii) the cleavage of a human C5 protein to form C5a and C5b; or (iv) the proper intracellular trafficking of, or secretion by a cell, of a complement component C5 protein. Inhibition of complement component C5 protein expression includes: inhibition of transcription of a gene encoding a human C5 protein; increased degradation of an mRNA encoding a human C5 protein; inhibition of translation of an mRNA encoding a human C5 protein; increased degradation of a human C5 protein; inhibition of proper processing of a pre-pro human C5 protein; or inhibition of proper trafficking or secretion by a cell of a human C5 protein. Methods for determining whether a candidate agent is an inhibitor of human complement component C5 are known in the art and described herein.

An inhibitor of human complement component C5 can be, e.g., a small molecule, a polypeptide, a polypeptide analog, a nucleic acid, or a nucleic acid analog.

"Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J. Am. Chem. Soc.* (1998) 120:8565-8566). It is within the scope of this application that such a library may be used to screen for inhibitors of human complement component C5. There are numerous commercially available compound libraries, such as the Chembridge DIVERSet. Libraries are also available from academic investigators, such as the Diversity set from the NCI developmental therapeutics program. Rational drug design may also be employed. For example, rational drug design can employ the use of crystal or solution structural information on the human complement component C5 protein. See, e.g., the structures described in Hagemann et al. (2008) *J Biol Chem* 283(12):7763-75 and Zuiderweg et al. (1989) *Biochemistry* 28(1):172-85. Rational drug design can also be achieved based on known compounds, e.g., a known inhibitor of C5 (e.g., an antibody, or antigen-binding fragment thereof, that binds to a human complement component C5 protein).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry. Each peptidomimetic may further have one or more unique additional binding elements.

Nucleic acid inhibitors can be used to decrease expression of an endogenous gene encoding human complement component C5. The nucleic acid antagonist can be, e.g., an siRNA, a dsRNA, a ribozyme, a triple-helix former, an aptamer, or an antisense nucleic acid. siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. The siRNA sequences can be, in some embodiments, exactly complementary to the target mRNA. dsRNAs and siRNAs in particular can be used to silence gene expression in mammalian cells (e.g., human cells). See, e.g., Clemens et al. (2000) *Proc. Natl. Acad. Sci. USA* 97:6499-6503; Billy et al. (2001) *Proc. Natl. Acad. Sci. USA* 98:14428-14433; Elbashir et al. (2001) *Nature* 411:494-8; Yang et al. (2002) *Proc. Natl. Acad. Sci. USA* 99:9942-9947, and U.S. Patent Application Publication Nos. 20030166282, 20030143204, 20040038278, and 20030224432. Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. Hybridization of antisense oligonucleotides with mRNA (e.g., an mRNA encoding a human C5 protein) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA. Exemplary antisense compounds include DNA or RNA sequences that specifically hybridize to the target nucleic acid, e.g., the mRNA encoding a human complement component C5 protein. The complementary region can extend for between about 8 to about 80 nucleobases. The compounds can include one or more modified nucleobases.

Modified nucleobases may include, e.g., 5-substituted pyrimidines such as 5-iodouracil, 5-iodocytosine, and $C_5$-propynyl pyrimidines such as $C_5$-propynylcytosine and $C_5$-propynyluracil. Other suitable modified nucleobases include, e.g., 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. See, e.g., U.S. Pat. Nos. 4,987,071; 5,116,742; and U.S. Pat. No. 5,093,246; "Antisense RNA and DNA," D. A. Melton, Ed., Cold Spring Harbor Laboratory, Cold Spring Harbor, N.Y. (1988); Haselhoff and Gerlach (1988) *Nature* 334:585-59; Helene, C. (1991) *Anticancer Drug D* 6:569-84; Helene (1992) *Ann. NY. Acad. Sci.* 660:27-36; and Maher (1992) *Bioassays* 14:807-15.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol.* 173:305-326).

In some embodiments, the inhibitor of human C5 is an antibody, or antigen-binding fragment thereof, which binds to a human complement component C5 protein. (Hereinafter, the antibody may sometimes be referred to as an "anti-C5 antibody.")

In some embodiments, the anti-C5 antibody binds to an epitope in the human pro-C5 precursor protein. For example, the anti-C5 antibody can bind to an epitope in the human complement component C5 protein comprising, or consisting of, the amino acid sequence depicted in SEQ ID NO:1 (NCBI Accession No. AAA51925 and Haviland et al., supra).

An "epitope" refers to the site on a protein (e.g., a human complement component C5 protein) that is bound by an antibody. "Overlapping epitopes" include at least one (e.g., two, three, four, five, or six) common amino acid residue(s).

In some embodiments, the anti-C5 antibody binds to an epitope in the human pro-C5 precursor protein lacking the leader sequence. For example, the anti-C5 antibody can bind to an epitope in the human complement component C5 protein comprising, or consisting of, the amino acid sequence depicted in SEQ ID NO:2, which is a human C5 protein lacking the amino terminal leader sequence.

In some embodiments, the anti-C5 antibody can bind to an epitope in the alpha chain of the human complement component C5 protein. For example, the anti-C5 antibody can bind to an epitope within, or overlapping with, a protein having the amino acid sequence depicted in SEQ ID NO:3, which is the human complement component C5 alpha chain protein. Antibodies that bind to the alpha chain of C5 are described in, for example, Ames et al. (1994) *J Immunol* 152:4572-4581.

In some embodiments, the anti-C5 antibody can bind to an epitope in the beta chain of the human complement component C5 protein. For example, the anti-C5 antibody can bind to an epitope within, or overlapping with, a protein having the amino acid sequence depicted in SEQ ID NO:4, which is the human complement component C5 beta chain protein. Antibodies that bind to the C5 beta chain are described in, e.g., Moongkarndi et al. (1982) *Immunobiol.* 162:397; Moongkarndi et al. (1983) *Immunobiol.* 165:323; and Mollnes et al. (1988) *Scand. J. Immunol.* 28:307-312.

In some embodiments, the anti-C5 antibody can bind to an epitope within, or overlapping with, an antigenic peptide fragment of a human complement component C5 protein. For example, the anti-C5 antibody can bind to an epitope within, or overlapping with, an antigen peptide fragment of a human complement component C5 protein, the fragment containing, or consisting of, the following amino acid sequence: VIDHQGTKSSKCVRQKVEGSS (SEQ ID NO:5) or KSSKC (SEQ ID NO:6).

In some embodiments, the anti-C5 antibody can bind to an epitope within, or overlapping with, a fragment of a human complement component C5 protein, the fragment containing, or consisting of, any one of the following amino acid sequences (which are exemplary antigenic fragments of SEQ ID NO:1):

(SEQ ID NO: 7)
NFSLETWFGKEILVKTLRVVPEGVKRESYSGVTLDPRGIYGTISRRKEFP
YRIPLDLVPKTEIKRILSVKGLLVGEILSAVLSQEGINILTHLPKGSAEA
ELMSVVPVFYVFHYLETGNHWNIFHSD;

(SEQ ID NO: 8)
SESPVIDHQGTKSSKCVRQKVEGSSSHLVTFTVLPLEIGLHNINFSLETW
FGKEILVKTLRVVPEGVKRESYSGVTLDPRGIYGTISRRKEFPYRIPLDL
VPKTEIKRILSVKGLLVGEILSAVLSQEGINILTHLPKGSAEAELMSVVP
VFYVFHYLETGNHWNIFHSDPLIEKQKLKKKLKEGMLSIMSYRNADYSY
S;

(SEQ ID NO: 9)
SHKDMQLGRLHMKTLLPVSKPEIRSYFPES;

(SEQ ID NO: 10)
SHKDMQLGRLHMKTLLPVSKPEIRSYFPESWLWEVHLVPRRKQLQFALPD
SLTTWEIQGIGISNTGICVADTVKAKVFKDVFLEMNIPYSVVRGEQIQLK
GTVYNYRTSGMQFCVKMSAVEGICTSESPVIDHQGTKSSKCVRQKVEGSS
SHLVTFTVLPLEIGLHNINFSLETWFGKEILVKTLRVVPEGVKRESYSGV
TLDPRGIYGTISRRKEFPYRIPLDLVPKTEIKRILSVKGLLVGEILSAVL
SQEGINILTHLPKGSAEAELMSVVPVFYVFHYLETGNHWNIFHSDPLIEK
QKLKKKLKEGMLSIMSYRNADYSYS;
and (SEQ ID NO: 11)
DHQGTKSSKCVRQKVEG.

Additional exemplary antigenic fragments of human complement component C5 are disclosed in, e.g., U.S. Pat. No. 6,355,245, the disclosure of which is incorporated herein by reference.

In some embodiments, the anti-C5 antibody specifically binds to a human complement component C5 protein (e.g., the human C5 protein having the amino acid sequence depicted in SEQ ID NO:1). The terms "specific binding" or "specifically binds" refer to two molecules forming a complex (e.g., a complex between an antibody and a complement component C5 protein) that is relatively stable under physiologic conditions. Typically, binding is considered specific when the association constant ($K_a$) is higher than $10^6$ M$^{-1}$. Thus, an antibody can specifically bind to a C5 protein with a $K_a$ of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ or higher) M$^{-1}$. Examples of antibodies that specifically bind to a human complement component C5 protein are described in, e.g., U.S. Pat. No. 6,355,245 http://patft.uspto.gov/netacgi/nph-Parser?Sect1=PTO1& Sect2=HITOFF&d=PALL&p=1&u=%2Fnetahtml%- 2FPTO%2Fsrchnum.htm&r=1&f=G&l=50&s1=6355245. PN.&OS=PN/6355245&RS=PN/6355245-h0#h0http.//patf- t.uspto.gov/netacgi/nph-Parser?Sect1=PTO1& Sect2=HITOFF&d=PALL&p=1&u=%2Fnetahtml- %2FPTO%2Fsrchnum.htm&r=1&f=G&l=50&s1= 6355245.PN.&OS=PN/6355245&RS=PN/6355245- h2#h26,355,245, the disclosure of which is incorporated herein by reference in its entirety.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2$^{nd}$ Edition, Oxford University Press, NY, Oxford; Johne et al. (1993) *J. Immunol. Meth.* 160:191-198; Jonsson et al. (1993) *Ann. Biol. Clin.* 51:19-26; and Jonsson et al. (1991) *Biotechniques* 11:620-627. See also, U.S. Pat. No. 6,355,245.

In some embodiments, the anti-C5 antibody can crossblock binding of another antibody that binds to an epitope within, or overlapping with, a human complement component C5 protein. In some embodiments, the anti-C5 antibody can crossblock binding of an antibody that binds to an epitope within, or overlapping with, a peptide fragment of a human complement component C5 protein. The peptide fragment can be a fragment of a human complement component C5 protein having the amino acid sequence depicted in any one of SEQ ID NOS:1-11. For example, the peptide fragment can contain, or consist of, the following amino acid sequence: VIDHQGTKSSKCVRQKVEGSS (SEQ ID NO:5).

As used herein, the term "crossblocking antibody" refers to an antibody that lowers the amount of binding of anti-C5 antibody to an epitope on a complement component C5 protein relative to the amount of binding of the anti-C5 antibody to the epitope in the absence of the antibody. Suitable methods for determining whether a first antibody crossblocks binding of a second antibody to an epitope are known in the art. For example, crossblocking antibodies can be identified by comparing the binding of the 5G1.1 anti-C5 monoclonal antibody (produced by the hybridoma cell line ATCC designation HB-11625; see U.S. Pat. No. 6,355,245) in the presence and absence of a test antibody. Decreased binding of the 5G1.1 antibody in the presence of the test antibody as compared to binding of the 5G1.1 antibody in the absence of the test antibody indicates the test antibody is a crossblocking antibody.

Methods for identifying the epitope to which a particular antibody (e.g., an anti-C5 antibody) binds are also known in the art. For example, the binding epitope of an anti-C5 antibody can be identified by measuring the binding of the antibody to several (e.g., three, four, five, six, seven, eight, nine, 10, 15, 20, or 30 or more) overlapping peptide fragments of a complement component C5 protein (e.g., several overlapping fragments of a protein having the amino acid sequence depicted in any one of SEQ ID NOs:1-11). Each of the different overlapping peptides is then bound to a unique address on a solid support, e.g., separate wells of a multiwell assay plate. Next, the anti-C5 antibody is interrogated by contacting it to each of the peptides in the assay plate for an amount of time and under conditions that allow for the antibody to bind to its epitope. Unbound anti-C5 antibody is removed by washing each of the wells. Next, a detectably-labeled secondary antibody that binds to the anti-C5 antibody, if present in a well of the plate, is contacted to each of the wells, and unbound secondary antibody is removed by washing steps. The presence or amount of the detectable signal produced by the detectably-labeled secondary antibody in a well is an indication that the anti-C5 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J Immunol. Methods* 160: 20191-8).

The anti-C5 antibodies described herein can have activity in blocking the generation or activity of the C5a and/or C5b active fragments of a complement component C5 protein (e.g., a human C5 protein). Through this blocking effect, the anti-C5 antibodies inhibit, e.g., the proinflammatory effects of C5a and the generation of the C5b-9 membrane attack complex (MAC) at the surface of a cell. Anti-C5 antibodies that have the ability to block the generation of C5a are described in, e.g., Moongkarndi et al. (1982) *Immunobiol.* 162:397 and Moongkarndi et al. (1983) *Immunobiol.* 165: 323.

In some embodiments, an anti-C5 antibody, or antigen-binding fragment thereof, can reduce the ability of a C5 protein to bind to human complement component C3b (e.g., C3b present in an AP or CP C5 convertase complex) by greater than 50 (e.g., greater than 55, 60, 65, 70, 75, 80, 85, 90, or 95 or more) %. In some embodiments, upon binding to a C5 protein, the anti-C5 antibody or antigen-binding fragment thereof can reduce the ability of the C5 protein to bind to complement component C4b (e.g., C4b present in a CP C5 convertase) by greater than 50 (e.g., greater than 55, 60, 65, 70, 75, 80, 85, 90, or 95 or more) %. Methods for determining whether an antibody can block the generation or activity of the C5a and/or C5b active fragments of a complement component C5 protein, or binding to complement component C4b or C3b, are known in the art and described in, e.g., U.S. Pat. No. 6,355,245 http://patft.uspto.gov/netacgi/nph-Parser?Sect1=PTO1&Sect2=
HITOFF&d=PALL&p=1&u=
%2Fnetahtml%2FPTO%2Fsrchnum.htm&r=1&f=
G&l=50&s1=6355245.PN.&OS=PN/6355245&RS=PN/
6355245-h0#h0http.//patft.uspto.gov/netacgi/nph-
Parser?Sect1=PTO1&Sect2=HITOFF&d=PALL&p=
1&u=2Fnetahtml%2FPTO%2Fsrchnum.htm&r=
1&f=G&l=50&s1=6355245.PN.&OS=PN/
6355245&RS=PN/6355245-h2#h26,355,245 and Wurzner et al. (1991) *Complement Inflamm* 8:328-340. (See also below.)

In some embodiments, an anti-C5 antibody binds to an amino-terminal region of the alpha chain of a complement component C5 protein, but does not bind to free C5a. Epitopes for an anti-C5 antibody within the amino-terminal region of the alpha chain include, e.g., epitopes within the human sequence VIDHQGTKSSKCVRQKVEGSS (SEQ ID NO:5).

In some embodiments, the composition comprises, and/or the antibody is, eculizumab (Soliris®; Alexion Pharmaceuticals, Inc., Cheshire, Conn.). (See, e.g., Kaplan (2002) *Curr Opin Investig Drugs* 3(7):1017-23; Hill (2005) *Clin Adv Hematol Oncol* 3 (11): 849-50; and Rother et al. (2007) *Nature Biotechnology* 25(11): 1256-1488.)

In some embodiments, the composition comprises, and/or the antibody is, pexelizumab (Alexion Pharmaceuticals, Inc., Cheshire, Conn.). (See, e.g., Whiss (2002) *Curr Opin Investig Drugs* 3(6):870-7; Patel et al. (2005) *Drugs Today (Barc)* 41(3):165-70; and Thomas et al. (1996) *Mol Immunol.* 33(17-18):1389-401.)

In some embodiments, the C5 inhibitor is an antibody that binds to C5a (sometimes referred to herein as "an anti-C5a antibody"). In some embodiments, the antibody binds to C5a, but not to full-length C5. As discussed above, the proform of C5, a 1676 amino acid residue precursor protein, is processed by a series of proteolytic cleavage events. The first 18 peptides (numbered −18 to −1) constitute a signal peptide that is cleaved from the precursor protein. The remaining 1658 amino acid protein is cleaved in two places to form the alpha and beta chains. The first cleavage event occurs between amino acid residues 655 and 656. The second cleavage occurs between amino acid residues 659 to 660. The two cleavage events result in the formation of three distinct polypeptide fragments: (i) a fragment comprising amino acids 1 to 655, which is referred to as the beta chain; (ii) a fragment comprising amino acids 660 to 1658, which is referred to as the alpha chain; and (iii) a tetrapeptide fragment consisting of amino acids 656 to 659. The alpha chain and the beta chain polypeptide fragments are connected to each other via disulfide bond and constitute the mature C5 protein. The CP or AP C5 convertase activates mature C5 by cleaving the alpha chain between residues 733 and 734, which results in the liberation of C5a fragment (amino acids 660 to 733). The remaining portion of mature C5 is fragment C5b, which contains the residues 734 to 1658 of the alpha chain disulfide bonded to the beta chain.

In vivo, C5a is rapidly metabolized by a serum enzyme, carboxypeptidase B, to a 73 amino acid form termed "C5a des-Arg," which has lost the carboxyterminal arginine residue. Accordingly, in some embodiments, an antibody that binds to C5a also binds to desarginated C5a. In some embodiments, an antibody that binds to C5a does not bind to desarginated C5a.

In some embodiments, the C5 inhibitor is an antibody that binds to a neoepitope present in C5a, i.e., an epitope that becomes exposed upon the liberation of C5a from the alpha chain fragment of mature C5. Antibodies that bind to C5a (e.g., a neo-epitope present in C5a) are known in the art as are methods for producing such antibodies. For example, an antibody that binds to C5a can have the binding specificity of a C5a neoepitope specific antibody described in any one of, e.g., PCT Publication No. WO 01/15731; Ames et al. (1994) *J Immunol* 152(9):4572-4581; Inoue (1989) *Complement Inflamm* 6(3):219-222; and U.S. Pat. No. 6,866,845. In another example, an antibody that binds to C5a can have the binding specificity of a commercial C5a neoepitope-specific antibody such as, but not limited to, sc-52633 (Santa Cruz Biotechnology, Inc., Santa Cruz, Calif.), 152-1486 (BD Pharmingen/BD Biosciences), ab11877 (Abcam, Cambridge, Mass.), and HM2079 (clone 2952; HyCult Biotechnology, the Netherlands). In some embodiments, an antibody that binds to C5a can crossblock the binding of any of the aforementioned C5a neoepitope-specific antibodies.

In some embodiments, the C5 inhibitor can be an antibody that binds to a mammalian (e.g., human) C5a protein. For example, the antibody can bind to a human C5a protein having the following amino acid sequence: TLQKKIEE-IAAKYKHSVVKKCCYDGACVNNDETCEQRAARIS-LGPRCIKAFTE CCVVASQLRANISHKDMQLGR (SEQ ID NO:12). The antibody can bind to human C5a at an epitope within or overlapping with the amino acid sequence: CCYDGACVNNDETCEQRAAR (SEQ ID NO:13); KCCYDGACVNNDETCEQR (SEQ ID NO:14); VNNDE-TCEQR (SEQ ID NO:15); VNNDET (SEQ ID NO:16); AARISLGPR (SEQ ID NO:17); CCYDGACVNNDET-CEQRAA (SEQ ID NO:18); CCYDGACVNNDETCEQRA (SEQ ID NO:19); CCYDGACVNNDETCEQR (SEQ ID NO:20); CCYDGACVNNDETCEQ (SEQ ID NO:21); CCYDGACVNNDETCE (SEQ ID NO:22); CYD-GACVNNDETCEQRAAR (SEQ ID NO:23); YDGACVNNDETCEQRAAR (SEQ ID NO:24); or CYD-GACVNNDETCEQRAAR (SEQ ID NO:25). In some embodiments, an antibody can bind to a human C5a protein or fragment thereof containing an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:12-25. Additional C5a protein fragments to which an antibody described herein can bind and methods for generating suitable C5a-specific antigen combining sites are set forth in, e.g., U.S. Pat. No. 4,686,100, the disclosure of which is incorporated herein by reference in its entirety.

In some embodiments, the binding of an antibody to C5a can inhibit the biological activity of C5a. Methods for measuring C5a activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). In some embodiments, the binding of an antibody to C5a can inhibit the interaction between C5a and C5aR1. Suitable methods for detecting and/or measuring the interaction between C5a and C5aR1 (in the presence and absence of an antibody) are known in the art and described in, e.g., Mary and Boulay (1993) *Eur J Haematol* 51(5):282-287; Kaneko et al. (1995) *Immunology* 86(1):149-154; Giannini et al. (1995) *J Biol Chem* 270(32):19166-19172; and U.S. Patent Application Publication No. 20060160726. For example, the binding of detectably labeled (e.g., radioactively labeled) C5a to C5aR1-expressing peripheral blood mononuclear cells can be evaluated in the presence and absence of an antibody. A decrease in the amount of detectably-labeled C5a that binds to C5aR1 in the presence of the antibody, as compared to the amount of binding in the absence of the antibody, is an indication that the antibody inhibits the interaction between C5a and C5aR1. In some embodiments, the binding of an antibody to C5a can inhibit the interaction between C5a and C5L2 (see below). Methods for detecting and/or measuring the interaction between C5a and C5L2 are known in the art and described in, e.g., Ward (2009) *J Mol Med* 87(4):375-378 and Chen et al. (2007) *Nature* 446(7132):203-207 (see below).

In some embodiments, the C5 inhibitor is an antibody that binds to C5b (sometimes referred to herein as "an anti-C5b antibody"). In some embodiments, the antibody binds to C5b, but does not bind to full-length C5. The structure of C5b is described above and also detailed in, e.g., Müller-Eberhard (1985) *Biochem Soc Symp* 50:235-246; Yamamoto and Gewurz (1978) *J Immunol* 120(6):2008-2015; and Haviland et al. (1991), supra. As described above, C5b combines with C6, C7, and C8 to form the C5b-8 complex at the surface of the target cell. Protein complex intermediates formed during the series of combinations include C5b-6 (including C5b and C6), C5b-7 (including C5b, C6, and C7), and C5b-8 (including C5b, C6, C7, and C8). Upon binding of several C9 molecules, the membrane attack complex (MAC, C5b-9 terminal complement complex (TCC)) is formed. When sufficient numbers of MACs insert into target cell membranes, the openings they create (MAC pores) mediate rapid osmotic lysis of the target cells.

In some embodiments, the binding of an antibody to C5b can inhibit the interaction between C5b and C6. In some embodiments, the binding of the antibody to C5b can inhibit the assembly or activity of the C5b-9 MAC-TCC. In some embodiments, the binding of an antibody to C5b can inhibit complement-dependent cell lysis (e.g., in vitro and/or in vivo). Suitable methods for evaluating whether an antibody inhibits complement-dependent lysis include, e.g., hemolytic assays or other functional assays for detecting the activity of soluble C5b-9. For example, a reduction in the cell-lysing ability of complement in the presence of an antibody can be measured by a hemolysis assay described by Kabat and Mayer (eds.), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

Antibodies that bind to C5b as well as methods for making such antibodies are known in the art. See, e.g., U.S. Pat. No. 6,355,245. Commercially available anti-C5b antibodies are available from a number of vendors including, e.g., Hycult Biotechnology (catalogue number: HM2080; clone 568) and Abcam™ (ab46151 or ab46168).

In some embodiments, the C5 inhibitor is an antibody that binds to a mammalian (e.g., human) form of C5b. For example, the antibody can bind to a portion of a human C5b protein having the following amino acid sequence: QEQ-TYVISAPKIFRVGASENIVIQVYGYTEAF-DATISIKSYPDKKF SYSSGHVHL SSENKFQNSAIL-TIQPKQLPGGQNPVSYVYLEVVSKHFSKSKRMPITY-DNGFLF IHTDKPVYTPDQSVKVRVYSLNDDLK-PAKRETVLTFIDPEGSEVDMVEEIDHI GIISFPDFKIP-SNPRYGMWTIKAKYKEDFSTTGTAYFEVKEYV-LPHFSVSIEPEY NFIGYKNFKNFEITIKARYFYNKVVTEADVYITF-GIREDLKDDQKEMMQTAM QNTMLINGIAQVTFD-SETAVKELSYYSLEDLNNKYLYIAVTVIESTGGF SEEAE IPGIKYVLSPYKLNLVATPLFLKPGIPYPIK-VQVKDSLDQLVGGVPVILNAQTID VNQETS-DLDPSKSVTRVDDGVASFVLNLPSGVTVLEFNVKT-DAPDLPEENQA REGYRAIAYSSLSQSYLYIDWTDNHKALLVGEHLNI-IVTPKSPYIDKITHYNYL ILSKGKIIHFGTREKFS-DASYQSINIPVTQNMVPSSRLLVYYIVTGEQTAEL-VSD SVWLNIEEKCGNQLQVHLSPDADAYSPGQTVSLN-MATGMDSWVALAAVDS AVYGVQRGAKKPLERVFQ-FLEKSDLGCGAGGGLNNANVFHLAGLTFLTNAN ADDSQENDEPCKEIL (SEQ ID NO:4). In some embodiments, the antibody can bind to a portion of a human C5b protein having the following amino acid sequence: LHM-KTLLPVSKPEIRSYFPESWLWEVHLVPRRKQLQ-FALPDSLTTWEIQGIGIS NTGICVADTVKAKVFKDV-FLEMNIPYSVVRGEQIQLKGTVYNYRTSGMQFCV KMSAVEGICTSESPVIDHQGTKSSKCVRQKVEG-SSSHLVTFTVLPLEIGLHNIN FSLETWFGKEILVKTL-RVVPEGVKRESYSGVTLDPRGIYGTISRRKEFPYRIPL DLVPKTEIKRILSVKGLLVGEILSAVLSQEGINILTHLP-KGSAEAELMSVVPVFY VFHYLETGNHWNIFHSD-PLIEKQKLKKKLKEGMLSIMSYRNADYSYSVWKG GSASTWLTAFALRVLGQVNKYVEQNQNSICNSLL-WLVENYQLDNGSFKENS QYQPIKLQGTLPVEAREN-SLYLTAFTVIGIRKAFDICPLVKIDTALIKADNFLLE NTLPAQSTFTLAISAYALSLGDKTHPQFRSIVSALKRE-ALVKGNPPIYRFWKD NLQHKDSSVPNTGTARMVET-TAYALLTSLNLKDINYVNPVIKWLSEEQRYGG GFYSTQDTINAIEGLTEYSLLVKQLRLSMDIDVSYKH-KGALHNYKMTDKNFL GRPVEVLLNDDLIVSTGFGS-GLATVHVTTVVHKTSTSEEVCSFYLKIDTQDIEA SHYRGYGNSDYKRIVACASYKPSREESSSGSSHAVM-DISLPTGISANEEDLKA LVEGVDQLFTDYQ-IKDGHVILQLNSIPSS DFLCVRFRIFELFEVGFLSPAT-FTVYEYHRPDKQCTMFYSTSNIKIQKVCEGAA CKCVEADCGQMQEELDLTISAETRKQTACK-PEIAYAYKVSITSITVENVFVKY KATLLDIYKTGEAV-AEKDSEITFIKKVTCTNAELVKGRQYLIMGKEALQ-IKYN FSFRYIYPLDSLTWIEYWPRDTTCSSCQAFLANLDE-FAEDIFLNGC (SEQ ID NO:26). In some embodiments, the antibody can bind to human C5b protein or fragment thereof containing an amino acid sequence that contains, or consists of, at least four (e.g., at least four, five, six, seven, eight, nine, 10, 11, 12, 13, 14, 15, 16, 17, 18, 19, or 20 or more) consecutive amino acids depicted in SEQ ID NO:4 or SEQ ID NO:26.

Additional exemplary sub-fragments of human C5b or C5a to which a C5 inhibitor antibody can bind are disclosed in, e.g., U.S. Pat. No. 6,355,245, the disclosure of which is incorporated herein by reference.

In some embodiments, the inhibitor is an antibody that specifically binds to a C5a polypeptide (e.g., the human C5a polypeptide having the amino acid sequence depicted in SEQ ID NO:12). In some embodiments, the inhibitor is an antibody that specifically binds to a C5b polypeptide.

Methods for determining whether a particular agent is an inhibitor of human complement component C5 are described herein and are known in the art. For example, the concentration and/or physiologic activity of C5a and C5b in a body fluid can be measured by methods well known in the art. Methods for measuring C5a concentration or activity include, e.g., chemotaxis assays, RIAs, or ELISAs (see, e.g., Ward and Zvaifler (1971) *J Clin Invest.* 50(3):606-16 and Wurzner et al. (1991) *Complement Inflamm.* 8:328-340). For C5b, hemolytic assays or assays for soluble C5b-9 as discussed herein can be used. Other assays known in the art can also be used. Using assays of these or other suitable types, candidate agents capable of inhibiting human complement component C5 such as an anti-C5 antibody, can be screened in order to, e.g., identify compounds that are useful in the methods described herein and determine the appropriate dosage levels of such compounds.

Methods for detecting inhibition of expression of mRNA or protein (e.g., inhibition of human C5 protein expression or expression of an mRNA encoding human C5 protein) are well known in the art of molecular biology and include, e.g., Northern blot and RT-PCR (or quantitative RT-PCR) techniques for mRNA and for protein detection, Western blot, dot blot, or ELISA techniques. (See, e.g., Sambrook et al. (1989) "Molecular Cloning: A Laboratory Manual, $2^{nd}$ Edition," Cold Spring Harbor Laboratory Press, Cold Spring Harbor, N.Y.)

Methods for determining whether a candidate compound inhibits the cleavage of human C5 into forms C5a and C5b are known in the art and described in, e.g., Moongkarndi et al. (1982) *Immunobiol.* 162:397; Moongkarndi et al. (1983) *Immunobiol.* 165:323; Isenman et al. (1980) *J Immunol.* 124(1):326-31; Thomas et al. (1996) *Mol. Immunol.* 33(17-18):1389-401; and Evans et al. (1995) *Mol. Immunol.* 32(16):1183-95.

Inhibition of human complement component C5 can also reduce the cell-lysing ability of complement in a subject's body fluids. Such reductions of the cell-lysing ability of complement present can be measured by methods well known in the art such as, for example, by a conventional hemolytic assay such as the hemolysis assay described by Kabat and Mayer (eds), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004)*N Engl J Med* 350(6):552.

Pharmaceutical Compositions and Formulations.

The compositions containing a complement inhibitor (e.g., an inhibitor of human complement component C5 such as an anti-C5 antibody or antigen-binding fragment thereof) can be formulated as a pharmaceutical composition, e.g., for administration to a subject to treat aHUS, CAPS, Degos disease, or TMA. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm. Sci.* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an anti-C5 antibody intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filtered sterilization. Generally, dispersions are prepared by incorporating an inhibitor of human complement component C5 (e.g., an anti-C5 antibody) described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the C5 inhibitor (e.g., an anti-C5 antibody or antigen-binding fragment thereof) can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. (See, e.g., J. R. Robinson (1978) "Sustained and Controlled Release Drug Delivery Systems," Marcel Dekker, Inc., New York.)

In some embodiments, an antibody described herein can be formulated in a composition suitable for intrapulmonary administration (e.g., for administration via nebulizer) to a mammal such as a human. Methods for preparing such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848.

In some embodiments, an inhibitor of human C5 (e.g., an anti-C5 antibody or antigen-binding fragment thereof) described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

The nucleic acid inhibitors of human complement component C5 described herein (e.g., an anti-sense nucleic acid or siRNA) can be incorporated into a gene construct to be used as a part of a gene therapy protocol to deliver nucleic acids that can be used to express and produce agents within cells. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized (e.g., antibody conjugated), polylysine conjugates, gramicidin S, artificial viral envelopes or other such intracellular carriers, as well as direct injection of the gene construct or $CaPO_4$ precipitation carried out in vivo. (See also, "Ex vivo Approaches," below.) Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci.*

USA 89:7640-7644; Kay et al. (1992) *Human Gene Therapy* 3:641-647; Dai et al. (1992) *Proc. Natl. Acad. Sci. USA* 89:10892-10895; Hwu et al. (1993) *J Immunol.* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252: 431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am. J. Respir. Cell. Mol. Biol.* 7:349-356; Samulski et al. (1989) *J Virol.* 63:3822-3828; and McLaughlin et al. (1989) *J Virol* 62: 1963-1973.

In some embodiments, more than one (e.g., two, three, four, five, six, seven, eight, nine, or 10 or more) inhibitor(s) (e.g., one or more inhibitors of human C5) can be co-formulated. For example, a C5-specific siRNA and an anti-C5 antibody can be formulated together.

In some embodiments, an inhibitor of human complement (e.g., an inhibitor human C5 such as an anti-C5 antibody or antigen-binding fragment thereof) described herein can be formulated with one or more additional active agents useful for treating a complement-associated disorder (e.g., any of the complement-associated disorders described herein such as APS, CAPS, aHUS, Degos disease, HELLP syndrome) or ameliorating a symptom thereof. For example, an anti-C5 antibody can be formulated with an antihypertensive, an anticoagulant, and/or a steroid (e.g., a corticosteroid). Examples of anticoagulants include, e.g., warfarin (Coumadin), aspirin, heparin, phenindione, fondaparinux, idraparinux, and thrombin inhibitors (e.g., argatroban, lepirudin, bivalirudin, or dabigatran). An inhibitor of human C5 (e.g., an anti-C5 antibody, an anti-C5a antibody, or an anti-C5b antibody) can also be formulated with a fibrinolytic agent (e.g., ancrod, ε-aminocaproic acid, antiplasmin-$a_1$, prostacyclin, and defibrotide), cyclophosphamide, or an anti-cytokine agent for the treatment of CAPS. Anti-cytokine agents include, e.g., antibodies or soluble receptors that bind to and modulate the activity of cytokine (e.g., a pro-inflammatory cytokine such as TNF). Examples of anti-cytokine agents include, e.g., a TNF inhibitor such as a soluble TNF receptor (e.g., etanercept; Enbrel®) or an anti-TNF antibody (e.g., infliximab; Remicade®). In some embodiments, the inhibitor can be formulated with, or for use with, an anti-CD20 agent such as rituximab (Rituxan™; Biogen Idec, Cambridge, Mass.). In some embodiments, the inhibitor of human C5 can be formulated for administration to a subject along with intravenous immunoglobulin therapy (IVIG) or with plasma exchange.

When the inhibitor of human C5 is to be used in combination with a second active agent, or when two or more inhibitors of human C5 are to be used (e.g., an anti-C5a antibody and an anti-C5b antibody), the agents can be formulated separately or together. For example, the respective pharmaceutical compositions can be mixed, e.g., just prior to administration, and administered together or can be administered separately, e.g., at the same or different times (see below).

As described above, a composition can be formulated such that it includes a therapeutically effective amount of an inhibitor of human C5 (e.g., an anti-C5 antibody or antigen-binding fragment thereof) or the composition can be formulated to include a sub-therapeutic amount of the inhibitor and a sub-therapeutic amount of one or more additional active agents such that the components in total are therapeutically effective for treating a complement-associated disorder such as any of those described herein. In some embodiments, a composition can be formulated to include two or more inhibitors of human C5, each at sub-therapeutic doses, such that the inhibitors in total are at a concentration that is therapeutically effective for treating a complement-associated disorder such as, e.g., aHUS, CAPS, Degos disease, or HELLP syndrome. Methods for determining a therapeutically effective dose (e.g., a therapeutically effective dose of an anti-C5 antibody) are known in the art and described herein.

Methods for Producing an Antibody

Suitable methods for producing an antibody (e.g., an anti-C5 antibody, an anti-C5a antibody, and/or an anti-C5b antibody), or antigen-binding fragments thereof, in accordance with the disclosure are known in the art (see, e.g., U.S. Pat. No. 6,355,245) and described herein. For example, monoclonal anti-C5 antibodies may be generated using complement component C5-expressing cells, a C5 polypeptide, or an antigenic fragment of C5 polypeptide (e.g., C5a or C5b), as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to human complement component C5.

Moreover, antibodies derived from recombinant libraries ("phage antibodies") may be selected using, e.g., C5-expressing cells, or polypeptides derived therefrom, as bait to isolate the antibodies or polypeptides on the basis of target specificity. The production and isolation of non-human and chimeric anti-C5 antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g., *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2 xYT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. No. 5,427,908; U.S. Pat. No. 5,508,717; Smith (1985) *Science* 225:1315-1317; Parmley and Smith (1988) *Gene* 73:305-318; De La Cruz et al. (1988) *Journal of Biological Chemistry* 263:4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

The cell culture supernatants are screened for the desired antibodies, preferentially by immunofluorescent staining of complement component C5-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a complement component C5-expressing cell line, or with Protein-A or -G.

Another embodiment provides a process for the preparation of a bacterial cell line secreting antibodies directed against a C5 protein in a suitable mammal. For example a rabbit is immunized with pooled samples from C5-expressing tissue or cells or C5 polypeptide or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a complement component C5 protein. In that process, a suitable mammal, for example a Balb/c mouse, is immunized with one or more polypeptides or antigenic fragments of C5 or with one or more polypeptides or antigenic fragments derived from a C5-expressing cell, the C5-expressing cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a C5-expressing Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally an immunogenic composition containing human C5 protein (or an immunogenic fragment thereof) several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced onto human constant domain gene segments (for example, U.S. Pat. No. 4,816,567). In this manner, non-human antibodies can be modified to make them more suitable for human clinical application (e.g., methods for treating or preventing a complement associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321: 522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc. Natl. Acad. Sci. USA* 90:2551; Jakobovits et al. (1993) *Nature* 362:255-258; Bruggemann et al. (1993) *Year in Immunol.* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a complement component C5 protein, fragments thereof, or cells expressing C5 protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J. Mol. Biol.* 227:381; Marks et al. (1991) *J. Mol. Biol.*, 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983), *Hybridoma* 2:361-367, the contents of each of which are incorporated herein by reference in their entirety.

For the generation of human antibodies, also see Mendez et al. (1998) *Nature Genetics* 15:146-156, Green and Jakobovits (1998) *J. Exp. Med.* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 2003-0229905 A1, 2004-0010810 A1, US 2004-0093622 A1, 2006-0040363 A1, 2005-0054055 A1, 2005-0076395 A1, 2005-0287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and U.S. Pat. Nos. 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res.* 20: 6287; Chen et al. (1993) *Int. Immunol.* 5: 647; Tuaillon et al. (1993) *Proc. Natl. Acad. Sci. USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J. Immunol.* 154: 6453-65; Fishwild et al. (1996) *Nature Biotechnology* 14: 845; and Tuaillon et al. (2000) *Eur. J. Immunol.* 10: 2998-3005, the disclosures of each of which are hereby incorporated by reference in their entirety.

In certain embodiments, de-immunized anti-C5 antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MEW molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-C5 antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, a recombinant DNA comprising an insert coding for a heavy chain variable domain and/or for a light chain variable domain of an anti-C5 antibody or a C5 protein-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-C5 antibodies can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-C5 antibody or a C5-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-C5 antibody or antigen-binding fragment (e.g., Fab, Fv, single-chain scFv, Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc. Natl. Acad. Sci. USA,* 78:2072) or Tn5 neo (Southern and Berg (1982) *Mol. Appl. Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc. Natl. Acad. Sci. USA,* 79:7147), polyoma virus (Deans et al. (1984) *Proc. Natl. Acad. Sci. USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983)*Mol. Cell Biol.* 3:280; Cepko et al. (1984) *Cell* 37:1053; and Kaufman (1985) *Proc. Natl. Acad. Sci. USA* 82:689.

As is evident from the disclosure, antibodies that binds to human complement components (e.g., antibodies that bind to C5, C5b, or C5a) can be used in therapies (e.g., therapies for a complement-associated disorder), including combination therapies, as well as in the monitoring of disease progression.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the human complement component C5 antigen the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al., *J. Exp. Med.* (1992) 175:217-225; Kostelny et al. (1992) *J. Immunol.* 148(5):1547-1553; Hollinger et al. (1993) *Proc. Natl. Acad. Sci. USA* 90:6444-6448; Gruber et al. (1994) *J. Immunol.* 152:5368; and Tutt et al. (1991) *J. Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. (See, e.g., Kostelny et al. (1992) *J. Immunol.* 148(5):1547-1553). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc. Natl. Acad. Sci. USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. (See, e.g., Gruber et al. (1994) *J. Immunol.* 152:5368.) Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024188 and WO 07/024715, the disclosures of each of which are incorporated herein by reference in their entirety.

Methods for Treatment

The above-described compositions (e.g., any of the C5 inhibitors described herein or pharmaceutical compositions thereof) are useful in, inter alia, methods for treating or preventing a variety of complement-associated disorders (e.g., AP-associated disorders or CP-associated disorders) in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP), intrapulmonary, intraocular, or intramuscular injection. Certain inhibitors, e.g., small molecules, can be orally administered to a subject.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. (See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety.) The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of a complement inhibitor (e.g., a C5 inhibitor such as an anti-C5 antibody) described herein, which dose is capable of treating or preventing a complement-associated disorder in a subject, can depend on a variety of factors including, e.g., the age, sex, and weight of a subject to be treated and the particular inhibitor compound used. For example, a different dose of an anti-C5 antibody may be required to treat a subject with RA as compared to the dose of a C5-specific siRNA molecule that is required to treat the same subject. Other factors affecting the dose administered to the subject include, e.g., the type or severity of the complement-associated disorder. For example, a subject having RA may require administration of a different dosage of an anti-C5 antibody than a subject with AMD. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

An antibody described herein can be administered as a fixed dose, or in a milligram per kilogram (mg/kg) dose. In some embodiments, the dose can also be chosen to reduce or avoid production of antibodies or other host immune responses against one or more of the active antibodies in the composition. While in no way intended to be limiting, exemplary dosages of an antibody include, e.g., 1-100 µg/kg, 0.5-50 µg/kg, 0.1-100 µs/kg, 0.5-25 µs/kg, 1-20 µs/kg, and 1-10 µs/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µs/kg, 0.5 µs/kg, 1.0 µg/kg, 2.0 µs/kg, 4 µs/kg, and 8 µs/kg, 0.1 mg/kg, 0.5 mg/kg, 1.0 mg/kg, 2.0 mg/kg, 4 mg/kg, and 8 mg/kg. Further exemplary dosage amounts and schedules are provided herein (see, e.g., Tables 1 and 2).

A pharmaceutical composition can include a therapeutically effective amount of a complement inhibitor (e.g., a C5 inhibitor such as an anti-C5 antibody) described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of the complement-associated disorder. For example, a therapeutically effective amount of an antibody that binds to C5a and C5b can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of a C5 inhibitor (e.g., an anti-C5 antibody) described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent (e.g., a C5 inhibitor) that will elicit the desired biological or medical response (e.g., an improvement in one or more symptoms of a complement-associated disorder). In some embodiments, a composition described herein contains a therapeutically effective amount of an anti-C5 antibody. In some embodiments, a composition described herein contains a therapeutically effective amount of a siRNA, which specifically binds to and promotes inactivation of C5 mRNA in a mammalian cell. In some embodiments, a composition described herein contains a therapeutically effective amount of an antibody, which specifically binds to C5a. In some embodiments, the composition contains any of the antibodies described herein and one or more (e.g., three, four, five, six, seven, eight, nine, 10, or 11 or more) additional therapeutic agents such that the composition as a whole is therapeutically effective. For example, a composition can contain an anti-C5 antibody described herein and an immunosuppressive agent, wherein the antibody and agent are each at a concentration that when combined are therapeutically effective for treating or preventing a complement-associated disorder in a subject.

Toxicity and therapeutic efficacy of such compositions can be determined by known pharmaceutical procedures in cell cultures or experimental animals (e.g., animal models of any of the complement-associated disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A complement inhibitor (e.g., a C5 inhibitor such as an anti-C5 antibody, an anti-C5a antibody, or a nucleic acid that binds to and promotes the inactivation of C5 mRNA in a mammalian cell) that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such an inhibitor lies generally within a range of circulating concentrations of the inhibitor that include the $ED_{50}$ with little or no toxicity. The dosage may vary within this range depending upon the dosage form employed and the route of administration utilized. For a C5 inhibitor (e.g., an anti-C5 antibody or an anti-C5a antibody) used as described herein (e.g., for treating or preventing a complement-associated disorder), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or by ELISA.

In some embodiments, the methods can be performed in conjunction with other therapies for complement-associated disorders. For example, the composition can be administered to a subject at the same time, prior to, or after, plasmapheresis, IVIG therapy, plasma infusion, or plasma exchange. See, e.g., Appel et al. (2005) *J Am. Soc Nephrol.* 16:1392-1404. In some embodiments, a C5 inhibitor (e.g., an anti-C5 antibody or an anti-C5a antibody) described herein is not administered in conjunction with IVIG. In some embodiments, the composition can be administered to a subject at the same time, prior to, or after, a kidney transplant. Exemplary methods for transplanting an organ (e.g., a kidney) or tissue along with exemplary dosing schedules for an anti-C5 antibody are provided herein.

A "subject," as used herein, can be any mammal. For example, a subject can be a human (e.g., a patient), a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject is a female.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a complement inhibitor (e.g., a C5 inhibitor such as an anti-C5 antibody, an anti-C5a antibody, or a nucleic acid (e.g., an siRNA or antisense nucleic acid) that binds to and promotes the inactivation of a C5 mRNA in a mammalian cell).

As described above, the complement inhibitors (e.g., a C5 inhibitor such as an anti-C5 antibody) described herein can be used to treat a variety of complement-associated disorders such as, e.g., AP-associated disorders and/or CP-associated disorders. Such disorders include, without limitation, rheumatoid arthritis (RA); antiphospholipid antibody syndrome; lupus nephritis; ischemia-reperfusion injury; atypical hemolytic uremic syndrome (aHUS); typical or infectious hemolytic uremic syndrome (tHUS); dense deposit disease (DDD); neuromyelitis optica (NMO); multifocal motor neuropathy (MMN); multiple sclerosis (MS); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; and traumatic brain injury. (See, e.g., Holers (2008) *Immunological Reviews* 223:300-316 and Holers and Thurman (2004) *Molecular Immunology* 41:147-152.) In some embodiments, the complement-associated disorder is a complement-associated vascular disorder such as a cardiovascular disorder, myocarditis, a cerebrovascular disorder, a peripheral (e.g., musculoskeletal) vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA). (See, e.g., U.S. patent application publication no. 20070172483.) Additional complement-associated disorders include, without limitation, MG, CAD, dermatomyositis, Graves' disease, atherosclerosis, Alzheimer's disease, systemic inflammatory response sepsis, septic shock, spinal cord injury, glomerulonephritis, Hashimoto's thyroiditis, type I diabetes, psoriasis, pemphigus, AIHA, ITP, Goodpasture syndrome, Degos disease, antiphospholipid syndrome (APS), and catastrophic APS (CAPS).

As used herein, a subject "at risk for developing a complement-associated disorder" (e.g., an AP-associated disorder or a CP-associated disorder) is a subject having one or more (e.g., two, three, four, five, six, seven, or eight or more) risk factors for developing the disorder. Risk factors will vary depending on the particular complement-associated disorder, but are well known in the art of medicine. For example, risk factors for developing DDD include, e.g., a predisposition to develop the condition, i.e., a family history of the condition or a genetic predisposition to develop the condition such as, e.g., one or more mutations in the gene encoding complement factor H (CFH), complement factor H-related 5 (CFHR5), and/or complement component C3 (C3). Such DDD-associated mutations as well as methods for determining whether a subject carries one or more of the mutations are known in the art and described in, e.g., Licht et al. (2006) *Kidney Int.* 70:42-50; Zipfel et al. (2006) "The role of complement in membranoproliferative glomerulonephritis," In: Complement and Kidney Disease, Springer, Berlin, pages 199-221; Ault et al. (1997) *J Biol. Chem.* 272:25168-75; Abrera-Abeleda et al. (2006) *J Med. Genet* 43:582-589; Poznansky et al. (1989) *J Immunol.* 143:1254-1258; Jansen et al. (1998) *Kidney Int.* 53:331-349; and Hegasy et al. (2002) *Am J Pathol* 161:2027-2034. Thus, a human at risk for developing DDD can be, e.g., one who has one or more DDD-associated mutations in the gene encoding CFH or one with a family history of developing the disease.

Risk factors for TTP are well known in the art of medicine and include, e.g., a predisposition to develop the condition, i.e., a family history of the condition or a genetic predisposition to develop the condition such as, e.g., one or more mutations in the ADAMTS13 gene. ADAMTS13 mutations associated with TTP are reviewed in detail in, e.g., Levy et al. (2001) *Nature* 413:488-494; Kokame et al. (2004) *Semin. Hematol.* 41:34-40; Licht et al. (2004) *Kidney Int.* 66:955-958; and Noris et al. (2005) *J. Am. Soc. Nephrol.* 16:1177-1183. Risk factors for TTP also include those conditions or agents that are known to precipitate TTP, or TTP recurrence, such as, but not limited to, cancer, bacterial infections (e.g., *Bartonella* sp. infections), viral infections (e.g., HIV and Kaposi's sarcoma virus), pregnancy, or surgery. See, e.g., Avery et al. (1998) *American Journal of Hematology* 58:148-149 and Tsai, supra). TTP, or recurrence of TTP, has also been associated with the use of certain therapeutic agents (drugs) including, e.g., ticlopidine, FK506, corticosteroids, tamoxifen, or cyclosporin A (see, e.g., Gordon et al. (1997) *Seminars in Hematology* 34(2):140-147). Hereinafter, such manifestations of TTP may be, where appropriate, referred to as, e.g., "infection-associated TTP," "pregnancy-associated TTP," or "drug-associated TTP." Thus, a human at risk for developing TTP can be, e.g., one who has one or more TTP-associated mutations in the ADAMTS13 gene. A human at risk for developing a recurrent form of TTP can be one, e.g., who has had TTP and has an infection, is pregnant, or is undergoing surgery.

Risk factors for aHUS are well known in the art of medicine and include, e.g., a predisposition to develop the condition, i.e., a family history of the condition or a genetic predisposition to develop the condition such as, e.g., one or more mutations in complement Factor H (CFH), membrane cofactor protein (MCP; CD46), C4b-binding protein, complement factor B (CFB), or complement factor I (CFI). (See, e.g., Warwicker et al. (1998) *Kidney Int.* 53:836-844; Richards et al. (2001) *Am J Hum Genet* 68:485-490; Caprioli et al. (2001) *Am Soc Nephrol* 12:297-307; Neuman et al. (2003) *J Med Genet* 40:676-681; Richards et al. (2006) *Proc Natl Acad Sci USA* 100:12966-12971; Fremeaux-Bacchi et al. (2005) *J Am Soc Nephrol* 17:2017-2025; Esparza-Gordillo et al. (2005) *Hum Mol Genet* 14:703-712; Goicoechea de Jorge et al. (2007) *Proc Natl Acad Sci USA* 104(1):240-245; Blom et al. (2008) *J Immunol.* 180(9):6385-91; and Fremeaux-Bacchi et al. (2004) *J Medical Genet* 41:e84). (See also Kavanagh et al. (2006) supra.) Risk factors also include, e.g., infection with *Streptococcus pneumoniae*, pregnancy, cancer, exposure to anti-cancer agents (e.g., quinine, mitomycin C, cisplatin, or bleomycin), exposure to immunotherapeutic agents (e.g., cyclosporine, OKT3, or interferon), exposure to anti-platelet agents (e.g., ticlopidine or clopidogrel), HIV infection, transplantation, autoimmune disease, and combined methylmalonic aciduria and homocystinuria (cblC). See, e.g., Constantinescu et al. (2004) *Am J Kidney Dis* 43:976-982; George (2003) *Curr Opin Hematol* 10:339-344; Gottschall et al. (1994) *Am J Hematol* 47:283-289; Valavaara et al. (1985) *Cancer* 55:47-50; Miralbell et al. (1996) *J Clin Oncol* 14:579-585; Dragon-Durey et al. (2005) *J Am Soc Nephrol* 16:555-63; and Becker et al. (2004) *Clin Infect Dis* 39:S267-S275.

Risk factors for HELLP are well known in the art of medicine and include, e.g., multiparous pregnancy, maternal age over 25 years, Caucasian race, the occurrence of preeclampsia or HELLP in a previous pregnancy, and a history of poor pregnancy outcome. (See, e.g., Sahin et al. (2001) *Nagoya Med J* 44(3):145-152; Sullivan et al. (1994) *Am J Obstet Gynecol* 171:940-943; and Padden et al. (1999) *Am Fam Physician* 60(3):829-836.) For example, a pregnant, Caucasian woman who developed preeclampsia during a first pregnancy can be one at risk for developing HELLP syndrome during, or following, a second pregnancy.

Risk factors for CAD are well known in the art of medicine and include, e.g., conditions or agents that are known to precipitate CAD, or CAD recurrence, such as, but not limited to, neoplasms or infections (e.g., bacterial and viral infections). Conditions known to be associated with the development of CAD include, e.g., HIV infection (and AIDS), hepatitis C infection, *Mycoplasma* pneumonia infection, Epstein-Barr virus (EBV) infection, cytomegalovirus (CMV) infection, rubella, or infectious mononucleosis. Neoplasms associated with CAD include, without limitation, non-Hodgkin's lymphoma. Hereinafter, such manifestations of CAD may be, where appropriate, referred to as, e.g., "infection-associated CAD" or "neoplasm-associated CAD." Thus, a human at risk for developing CAD can be, e.g., one who has an HIV infection, rubella, or a lymphoma. See also, e.g., Gertz (2006) *Hematology* 1:19-23; Horwitz et al. (1977) *Blood* 50:195-202; Finland and Barnes (1958) *AMA Arch Intern Med* 191:462-466; Wang et al. (2004) *Acta Paediatr Taiwan* 45:293-295; Michaux et al. (1998) *Ann Hematol* 76:201-204; and Chang et al. (2004) *Cancer Genet Cytogenet* 152:66-69.

Risk factors for a thrombotic microangiopathy (TMA) are well known in the art of medicine and include, e.g., a medical history of aHUS, TTP, or other conditions that are associated with TMA such as lupus, cancers, disseminating intravascular coagulation and other coagulopathies, and pre-eclampsia. See, e.g., Copelovitch and Kaplan (2008) *Pediatr Nephrol* 23 (10): 1761-7.

Risk factors for PCH are well known in the art of medicine and include, e.g., conditions or agents that are known to precipitate PCH, or PCH recurrence, such as, but not limited to, neoplasms, infections (e.g., bacterial and viral infections), or certain immunizations (e.g., measles immunization). Conditions known to be associated with the development of PCH include, e.g., syphilis (a *Treponema palladium* infection), measles, mumps, influenza virus infection, varicella-zoster virus infection, cytomegalovirus (CMV) infection, Epstein-Barr virus (EBV) infection, adenovirus infection, parvovirus B19 infection, Coxsackie A9 infection, *Haemophilus* influenza infection, *Mycoplasma pneumoniae* infection, and *Klebsiella pneumoniae* infection. See, e.g., Bunch et al. (1972) *Arch Dis Child* 47(252):299-300; Ziman et al. (2004) *Transfusion* 44(8):1127-1128; Sokol et al. (1984) *Acta Haematol* 72(4): 245-257; Papalia et al. (2000) *Br J Haematol* 109(2): 328-9; Sokol et al. (1982) *Acta Haematol* 68(4):268-277; and Bell et al. (1973) *Transfusion* 13(3):138-141. Neoplasms associated with PCH include, without limitation, both solid and hematopoietic neoplasms such as myelofibrosis, chronic lymphocytic leukemia (CLL), and non-Hodgkin's lymphoma. See, e.g., Sharara et al. (1994) *South Med J.* 87(3):397-9; Sivakumaran et al. (1999) *Br J Haematol* 105(1): 278-9; Breccia et al. (2004) *Eur J Haematol* 73(4):304-6; and Wynn et al. (1998) *Clin Lab Haematol* 20(6):373-5. Hereinafter, such manifestations of PCH may be, where appropriate, referred to as, e.g., "infection-associated PCH" or "neoplasm-associated PCH." Thus, a human at risk for developing PCH can be, e.g., one who has an EBV infection or a lymphoma.

Risk factors for MG are well known in the art of medicine and include, e.g., a predisposition to develop the condition, i.e., a family history of the condition or a genetic predisposition to develop the condition such as familial MG. For example, some HLA types are associated with an increased risk for developing MG. Risk factors for MG include the ingestion or exposure to certain MG-inducing drugs such as, but not limited to, D-penicillamine. See, e.g., Drosos et al. (1993) *Clin Exp Rheumatol.* 11(4):387-91 and Kaeser et al. (1984) *Acta Neurol Scand Suppl.* 100:39-47. As MG can be episodic, a subject who has previously experienced one or more symptoms of having MG can be at risk for relapse. Thus, a human at risk for developing MG can be, e.g., one who has a family history of MG and/or one who has ingested or been administered an MG-inducing drug such as D-penicillamine.

As used herein, a subject "at risk for developing CAPS" is a subject having one or more (e.g., two, three, four, five, six, seven, or eight or more) risk factors for developing the disorder. Approximately 60% of the incidences of CAPS are preceded by a precipitating event such as an infection. Thus, risk factors for CAPS include those conditions known to precipitate CAPS such as, but not limited to, certain cancers (e.g., gastric cancer, ovarian cancer, lymphoma, leukemia, endometrial cancer, adenocarcinoma, and lung cancer), pregnancy, puerperium, transplantation, primary APS, rheumatoid arthritis (RA), systemic lupus erythematosus (SLE), surgery (e.g., eye surgery), and certain infections. Infections include, e.g., parvovirus B19 infection and hepatitis C infection. Hereinafter, such manifestations of CAPS may be referred to as, e.g., "cancer-associated CAPS," "transplantation-associated CAPS," "RA-associated CAPS," "infection-associated CAPS," or "SLE-associated CAPS." See, e.g., Soltész et al. (2000) *Haematologia (Budep)* 30(4):303-311; Ideguchi et al. (2007) *Lupus* 16(1):59-64; Manner et al. (2008) *Am J Med. Sci.* 335(5):394-7; Miesbach et al. (2006) *Autoimmune Rev.* 6(2):94-7; Gómez-Puerta et al. (2006) *Autoimmune Rev.* 6(2):85-8; Gómez-Puerta et al. (2006) *Semin. Arthritis Rheum.* 35(5):322-32; Kasamon et al. (2005) *Haematologia* 90(3):50-53; Atherson et al. (1998) *Medicine* 77(3):195-207; and Canpolat et al. (2008) *Clin Pediatr* 47(6):593-7. Thus, a human at risk for developing CAPS can be, e.g., one who has primary CAPS and/or a cancer that is known to be associated with CAPS.

From the above it will be clear that subjects "at risk for developing a complement-associated disorder" (e.g., an AP-associated disorder or a CP-associated disorder) are not all the subjects within a species of interest.

A subject "suspected of having a complement-associated disorder" (e.g., an alternative complement pathway-associated disorder) is one having one or more (e.g., two, three, four, five, six, seven, eight, nine, or 10 or more) symptoms of the disease. Symptoms of these disorders will vary depending on the particular disorder, but are known to those of skill in the art of medicine. For example, symptoms of DDD include, e.g.: one or both of hematuria and proteinuria; acute nephritic syndrome; drusen development and/or visual impairment; acquired partial lipodystrophy and complications thereof; and the presence of serum C3 nephritic factor (C3NeF), an autoantibody directed against C3bBb, the C3 convertase of the alternative complement pathway. (See, e.g., Appel et al. (2005), supra). Symptoms of aHUS include, e.g., severe hypertension, proteinuria, uremia, lethargy/fatigue, irritability, thrombocytopenia, microangiopathic hemolytic anemia, and renal function impairment (e.g., acute renal failure). Symptoms of TTP include, e.g., microthrombi, thrombocytopenia, fever, low ADAMTS13 metalloproteinase expression or activity, fluctuating central nervous system abnormalities, renal failure, microangiopathic hemolytic anemia, bruising, purpura, nausea and vomiting (e.g., resulting from ischemia in the GI tract or from central nervous system involvement), chest pain due to cardiac ischemia, seizures, and muscle and joint pain. Symptoms of RA can include, e.g., stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing. Symptoms of HELLP are known in the art of medicine and include, e.g., malaise, epigastric pain, nausea, vomiting, headache, right upper quadrant pain, hypertension, proteinuria, blurred vision, gastrointestinal bleeding, hypoglycemia, paresthesia, elevated liver enzymes/liver damage, anemia (hemolytic anemia), and low platelet count, any of which in combination with pregnancy or recent pregnancy. (See, e.g., Tomsen (1995) *Am J Obstet Gynecol* 172:1876-1890; Sibai (1986) *Am J Obstet Gynecol* 162:311-316; and Padden (1999), supra.)

Symptoms of CAPS are well known in the art of medicine and include, e.g., histopathological evidence of multiple small vessel occlusions; the presence of antiphospholipid antibodies (usually at high titer), vascular thromboses, severe multi-organ dysfunction, malignant hypertension, acute respiratory distress syndrome, disseminated intravascular coagulation, microangiopathic hemolytic anemia, schistocytes, and thrombocytopenia. CAPS can be distinguished from APS in that patients with CAPS generally present with severe multiple organ dysfunction or failure, which is characterized by rapid, diffuse small vessel ischemia and thromboses predominantly affecting the parenchymal organs. In contrast, APS is associated with single venous or arterial medium-to-large blood vessel occlusions. Symptoms of MG include, e.g., fatigability and a range of muscle weakness-related conditions including: ptosis (of one or both eyes), diplopia, unstable gait, depressed or distorted facial expressions, and difficulty chewing, talking, or swallowing. In some instances, a subject can present with partial or complete paralysis of the respiratory muscles. Symptoms of CAD include, e.g., pain, fever, pallor, anemia, reduced blood flow to the extremities (e.g., with gangrene), and renal disease or acute renal failure. In some embodiments, the symptoms can occur following exposure to cold temperatures.

From the above it will be clear that subjects "suspected of having a complement-associated disorder" are not all the subjects within a species of interest.

In some embodiments, the methods can include identifying the subject as one having, suspected of having, or at risk for developing, a complement-associated disorder in a subject. Suitable methods for identifying the subject are known in the art. For example, suitable methods (e.g., sequencing techniques or use of microarrays) for determining whether a human subject has a DDD-associated mutation in a CFH, CFHR5, or C3 gene are described in, e.g., Licht et al. (2006) *Kidney Int.* 70:42-50; Zipfel et al. (2006), supra; Ault et al. (1997) *J Biol. Chem.* 272:25168-75; Abrera-Abeleda et al. (2006)*J Med Genet* 43:582-589; Poznansky et al. (1989)*J Immunol.* 143:1254-1258; Jansen et al. (1998) *Kidney Int.* 53:331-349; and Hegasy et al. (2002) *Am J Pathol* 161: 2027-2034. Methods for detecting the presence of characteristic DDD-associated electron-dense deposits are also well known in the art. For example, a medical practitioner can obtain a tissue biopsy from the kidney of a patient and subject the tissue to electron microscopy. The medical practitioner may also examine the tissue by immunofluorescence to detect the presence of C3 using an anti-C3 antibody and/or light microscopy to determine if there is membranoproliferative glomerulonephritis. See, e.g., Walker et al. (2007) *Mod. Pathol.* 20:605-616 and Habib et al. (1975) *Kidney Int.* 7:204-215. In some embodiments, the identification of a subject as one having DDD can include assaying a blood sample for the presence of C3NeF. Methods for detecting the presence of C3NeF in blood are described in, e.g., Schwertz et al. (2001) *Pediatr Allergy Immunol.* 12:166-172.

In some embodiments, the medical practitioner can determine whether there is increased complement activation in a subject's serum. Indicia of increased complement activation include, e.g., a reduction in CH50, a decrease in C3, and an increase in C3dg/C3d. See, e.g., Appel et al. (2005), supra. In some embodiments, a medical practitioner can examine a subject's eye for evidence of the development of drusen and/or other visual pathologies such as AMD. For example, a medical practitioner can use tests of retinal function such as, but not limited to, dark adaptation, electroretinography, and electrooculography (see, e.g., Colville et al. (2003) *Am J Kidney Dis.* 42:E2-5).

Methods for identifying a subject as one having, suspected of having, or at risk for developing, TTP are also known in the art. For example, Miyata et al. describe a variety of assays for measuring ADAMTS13 activity in a biological sample obtained from a subject (*Curr Opin Hematol* (2007) 14(3):277-283). Suitable ADAMTS13 activity assays, as well as phenotypically normal ranges of ADAMTS13 activity in a human subject, are described in, e.g., Tsai (2003) *J. Am. Soc. Nephrol* 14:1072-1081; Furlan et al. (1998) *New Engl J Med.* 339:1578-1584; Matsumoto et al. (2004) *Blood* 103:1305-1310; and Mori et al. (2002) *Transfusion* 42:572-580. Methods for detecting the presence of inhibitors of ADAMTS13 (e.g., autoantibodies that bind to ADAMTS13) in a biological sample obtained from a subject are known in the art. For example, a serum sample from a patient can be mixed with a serum sample from a subject without TTP to detect the presence of anti-ADAMTS13 antibodies. In another example, immunoglobulin protein can be isolated from patient serum and used in in vitro ADAMTS13 activity assays to determine if an anti-ADAMTS13 antibody is present. See, e.g., Dong et al. (2008) *Am J Hematol.* 83(10):815-817. In some embodiments, risk of developing TTP can be determined by assessing whether a patient carries one or more mutations in the ADAMTS13 gene. Suitable methods (e.g., nucleic acid arrays or DNA sequencing) for detecting a mutation in the ADAMTS13 gene are known in the art and described in, e.g., Levy et al., supra; Kokame et al., supra; Licht et al., supra; and Noris et al., supra.

In addition, methods for identifying a subject as one having, suspected of having, or at risk for developing aHUS are known in the art. For example, laboratory tests can be performed to determine whether a human subject has thrombocytopenia, microangiopathic hemolytic anemia, or acute renal insufficiency. Thrombocytopenia can be diagnosed by a medical professional as one or more of: (i) a platelet count that is less than 150,000/mm$^3$ (e.g., less than 60,000/mm$^3$); (ii) a reduction in platelet survival time, reflecting enhanced platelet disruption in the circulation; and (iii) giant platelets observed in a peripheral smear, which is consistent with secondary activation of thrombocytopoiesis. Microangiopathic hemolytic anemia can be diagnosed by a medical professional as one or more of: (i) hemoglobin concentrations that are less than 10 mg/dL (e.g., less than 6.5 mg/dL); (ii) increased serum lactate dehydrogenase (LDH) concentrations (>460 U/L); (iii) hyperbilirubinemia, reticulocytosis, circulating free hemoglobin, and low or undetectable haptoglobin concentrations; and (iv) the detection of fragmented red blood cells (schistocytes) with the typical aspect of burr or helmet cells in the peripheral smear together with a negative Coombs test. (See, e.g., Kaplan et al. (1992) "Hemolytic Uremic Syndrome and Thrombotic Thrombocytopenic Purpura," Informa Health Care (ISBN 0824786637) and Zipfel (2005) "Complement and Kidney Disease," Springer (ISBN 3764371668).)

A subject can also be identified as having aHUS by evaluating blood concentrations of C3 and C4 as a measure of complement activation or dysregulation. In addition, as is clear from the foregoing disclosure, a subject can be identified as having genetic aHUS by identifying the subject as harboring one or more mutations in a gene associated with aHUS such as CFI, CFB, CFH, or MCP (supra). Suitable methods for detecting a mutation in a gene include, e.g., DNA sequencing and nucleic acid array techniques. (See, e.g., Breslin et al. (2006) *Clin Am Soc Nephrol* 1:88-99 and Goicoechea de Jorge et al. (2007) *Proc Natl Acad Sci USA* 104:240-245.)

Symptoms characteristic of TMA include, e.g., fever, microangiopathic hemolytic anemia (schistocytes in a blood smear), renal failure, thrombocytopenia, and neurological manifestations.

Methods for diagnosing a subject as one having, suspected of having, or at risk for developing, RA are also known in the art of medicine. For example, a medical practitioner can examine the small joints of the hands, wrists, feet, and knees to identify inflammation in a symmetrical distribution. The practitioner may also perform a number of tests to exclude other types of joint inflammation including arthritis due to infection or gout. In addition, rheumatoid arthritis is associated with abnormal antibodies in the blood circulation of afflicted patients. For example, an antibody referred to as "rheumatoid factor" is found in approximately 80% of patients. In another example, anti-citrulline antibody is present in many patients with rheumatoid arthritis and thus it is useful in the diagnosis of rheumatoid arthritis when evaluating patients with unexplained joint inflammation. See, e.g., van Venrooij et al. (2008) *Ann NY Acad Sci* 1143:268-285 and Habib et al. (2007) *Immunol Invest* 37(8):849-857. Another antibody called "the antinuclear antibody" (ANA) is also frequently found in patients with rheumatoid arthritis. See, e.g., Benucci et al. (2008) *Clin Rheumatol* 27(1):91-95; Julkunen et al. (2005) *Scan J Rheumatol* 34(2):122-124; and Miyawaki et al. (2005) *J Rheumatol* 32(8):1488-1494.

A medical practitioner can also examine red blood cell sedimentation rate to help in diagnosing RA in a subject. The sedimentation rate can be used as a crude measure of the inflammation of the joints and is usually faster during disease flares and slower during remissions. Another blood test that can be used to measure the degree of inflammation present in the body is the C-reactive protein.

Furthermore, joint x-rays can also be used to diagnose a subject as having rheumatoid arthritis. As RA progresses, the x-rays can show bony erosions typical of rheumatoid arthritis in the joints. Joint x-rays can also be helpful in monitoring the progression of disease and joint damage over time. Bone scanning, a radioactive test procedure, can demonstrate the inflamed joints.

Methods for identifying a subject as one having, suspected of having, or at risk for developing, HELLP are known in the art of medicine. Hallmark symptoms of HELLP syndrome include hemolysis, elevated liver enzymes, and low platelet count. Thus, a variety of tests can be performed on blood from a subject to determine the level of hemolysis, the concentration of any of a variety of liver enzymes, and the platelet level in the blood. For example, the presence of schistocytes and/or elevated free hemoglobin, bilirubin, or serum LDH levels is an indication of intravascular hemolysis. Routine laboratory testing can be used to determine the platelet count as well as the blood level of liver enzymes such as, but not limited to, aspartate aminotransferase (AST) and alanine transaminase (ALT). Suitable methods for identifying a subject as having HELLP syndrome are also described in, e.g., Sibai et al. (1993), supra; Martin et al. (1990), supra; Padden (1999), supra; and Gleicher and Buttino (1998) "Principles & Practice of Medical Therapy in Pregnancy," 3$^{rd}$ Edition, Appleton & Lange (ISBN 083857677X).

Suitable methods for identifying the subject as having MG can be qualitative or quantitative. For example, a medical practitioner can examine the status of a subject's motor functions using a physical examination. Other qualitative tests include, e.g., an ice-pack test, wherein an ice pack is applied to a subject's eye (in a case of ocular MG) to determine if one or more symptoms (e.g., ptosis) are improved by cold (see, e.g., Sethi et al. (1987) *Neurology* 37(8):1383-1385). Other tests include, e.g., the "sleep test," which is based on the tendency for MG symptoms to improve following rest. In some embodiments, quantitative or semi-quantitative tests can be employed by a medical practitioner to determine if a subject has, is suspected of having, or is at risk for developing, MG. For example, a medical practitioner can perform a test to detect the presence or amount of MG-associated autoantibodies in a serum sample obtained from a subject. MG-associated autoantibodies include, e.g., antibodies that bind to, and modulate the activity of, acetylcholine receptor (AChR), muscle-specific receptor tyrosine kinase (MuSK), and/or striational protein. (See, e.g., Conti-Fine et al. (2006), supra). Suitable assays useful for detecting the presence or amount of an MG-associated antibody in a biological sample are known in the art and described in, e.g., Hoch et al. (2001) *Nat Med* 7:365-368; Vincent et al. (2004) *Semin Neurol.* 24:125-133; McConville et al. (2004) *Ann. Neurol.* 55:580-584; Boneva et al. (2006) *J Neuroimmunol.* 177:119-131; and Romi et al. (2005) *Arch Neurol.* 62:442-446.

Additional methods for diagnosing MG include, e.g., electrodiagnostic tests (e.g., single-fiber electromyography) and the Tensilon (or edrophonium) test, which involves injecting a subject with the acetylcholinesterase inhibitor edrophonium and monitoring the subject for an improvement in one or more symptoms. See, e.g., Pascuzzi (2003) *Semin Neurol* 23(1):83-88; Katirji et al. (2002) *Neurol Clin* 20:557-586; and "Guidelines in Electrodiagnostic Medicine. American Association of Electrodiagnostic Medicine," *Muscle Nerve* 15:229-253.

A subject can be identified as having CAD using an assay to detect the presence or amount (titer) of agglutinating autoantibodies that bind to the I antigen on red blood cells. The antibodies can be monoclonal (e.g., monoclonal IgM or IgA) or polyclonal. Suitable methods for detecting these antibodies are described in, e.g., Christenson and Dacie (1957) *Br J Haematol* 3:153-164 and Christenson et al. (1957) *Br J Haematol* 3:262-275. A subject can also be diagnosed as having CAD using one or more of a complete blood cell count (CBC), urinalysis, biochemical studies, and a Coombs test to test for hemolysis in blood. For example, biochemical studies can be used to detect elevated lactase dehydrogenase levels, elevated unconjugated bilirubin levels, low haptoglobin levels, and/or the presence of free plasma hemoglobin, all of which can be indicative of acute hemolysis. Other tests that can be used to detect CAD include detecting complement levels in the serum. For example, due to consumption during the acute phase of hemolysis, measured plasma complement levels (e.g., C2, C3, and C4) are decreased in CAD.

Typical (or infectious) HUS, unlike aHUS, is often identifiable by a prodrome of diarrhea, often bloody in nature, which results from infection with a shiga-toxin producing microorganism. A subject can be identified as having typical HUS when shiga toxins and/or serum antibodies against shiga toxin or LPS are detected in the stool of an individual. Suitable methods for testing for anti-shiga toxin antibodies or LPS are known in the art. For example, methods for detecting antibodies that bind to shiga toxins Stx1 and Stx2 or LPS in humans are described in, e.g., Ludwig et al. (2001) *J Clin Microbiol* 39(6):2272-2279.

Symptoms of this condition are known to those of skill in the art of medicine and include, e.g., pain, fever, pallor, icterus, urticarial dermal eruption, hemoglobinuria, hemoglobinemia, anemia, and renal disease or acute renal failure. In some embodiments, the symptoms can occur following exposure to cold temperatures.

In some embodiments, the methods can include identifying the subject as one having, suspected of having, or at risk for developing, PCH. Suitable methods for identifying the subject are known in the art. For example, a subject can be diagnosed as having PCH using a Donath-Landsteiner test, which is an assay to detect the presence of the Donath-Landsteiner antibody in a subject's serum. The procedure involves incubating three samples—(1) the subject's serum; (2) normal serum; and (3) a mix of the subject's serum and normal serum—with P-antigen expressing red blood cells at 0 to 4° C. Next, the sample is warmed to 37° C. and visually inspected for hemolysis. If the Donath-Landsteiner antibody is present, hemolysis should occur in samples (1) and (3), but not in (2). See, e.g., Funato et al. (2007) *Eur J Haematol* 79(5):462; Win et al. (2005) Transfus Med. 15(3):254; Sokol et al. (1998) *Immunohematology* 14(3):109-12; Eder (2005) *Immunohematology* 21(2):56-62; and Dacie et al. (1957) *Br J Haematol* 3:77-87. A subject can also be diagnosed as having PCH using one or more of a complete blood cell count (CBC), urinalysis, biochemical studies, and a Coombs test. For example, biochemical studies can be used to detect elevated lactase dehydrogenase levels, elevated unconjugated bilirubin levels, low haptoglobin levels, and/or the presence of free plasma hemoglobin, all of which can be indicative of acute hemolysis. Other tests that can be used to detect PCH include detecting complement levels in the serum. For example, due to consumption during the acute phase of hemolysis, measured plasma complement levels (e.g., C2, C3, and C4) are decreased in PCH. See also, e.g., Nordhagen et al. (1984) *Acta Paediatr Scand* 73(2):258-262; Lindgren et al. (1985) *Transfusion* 25(2):142-4; Nordhagen et al. (1991) *Transfusion* 31(2):190-1; and Garratty (2001) *Transfusion* 41(8):1073-4.

In some embodiments, the composition can be administered to a subject prophylactically to prevent, or prevent relapse or recurrence of, PCH. For example, a subject who previously had an advanced *Mycoplasma* infection or who is newly diagnosed with a PCH-associated neoplasm can be administered a composition described herein to prevent, lessen the severity of, or prevent a recurrence of PCH.

In some embodiments, a C5 inhibitor (e.g., an anti-C5 antibody) described herein can be administered to a subject as a monotherapy. Alternatively, as described above, the antibody can be administered to a subject as a combination therapy with another treatment, e.g., another treatment for DDD, TTP, aHUS, RA, HELLP, MG, CAD, CAPS, tHUS, Degos disease, or any other complement-associated disorder described herein. For example, the combination therapy can include administering to the subject (e.g., a human patient) one or more additional agents (e.g., anti-coagulants, anti-hypertensives, or corticosteroids) that provide a therapeutic benefit to the subject who has, or is at risk of developing, DDD. In some embodiments, the combination therapy can include administering to the subject (e.g., a human patient) a C5 inhibitor (e.g., an anti-C5 antibody or an anti-C5a antibody) and an immunosuppressive agent such as Remicade® for use in treating RA. In some embodiments, the C5 inhibitor and the one or more additional active agents are administered at the same time. In other embodiments, a C5 inhibitor is administered first in time and the one or more additional active agents are administered second in time. In some embodiments, the one or more additional active agents are administered first in time and the C5 inhibitor is administered second in time.

A C5 inhibitor (e.g., an anti-C5 antibody) described herein can replace or augment a previously or currently administered therapy. For example, upon treating with an anti-C5 antibody, administration of the one or more additional active agents can cease or diminish, e.g., be administered at lower levels. In some embodiments, administration of the previous therapy can be maintained. In some embodiments, a previous therapy will be maintained until the level of the C5 inhibitor (e.g., anti-C5 antibody or an anti-C5a antibody) reaches a level sufficient to provide a therapeutic effect. The two therapies can be administered in combination.

In some embodiments, a C5 inhibitor can be administered to a patient chronically. For example, a patient chronically treated with a complement-inhibiting agent (e.g., a C5 inhibitor or a C5a inhibitor) can be treated for a period of greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) with the agent in an amount and with a dosing frequency that are sufficient to maintain a concentration of the agent in the patient's blood that inhibits or substantially inhibits systemic complement activity in the patient. To maintain systemic complement inhibition in a patient, a C5 inhibitor can be chronically administered to the patient, e.g., once a week, once every two weeks, twice a week, once a day, once a month, or once every three weeks. In some embodiments of any of the methods described herein, the C5 inhibitor can be administered to a patient in an amount and with a frequency of administration effective to maintain a concentration of at least: 0.7 (e.g., at least 0.8, 0.9, one, two, three, four, five, six, seven, eight, nine, or 10 or more) bivalent C5 inhibitor (e.g., a whole antibody) molecule(s) per every C5 molecule in the patient's blood; or 1.5 (e.g., at least 1.6, 1.7, 1.8, 1.9, two, three, four, five, six, seven, eight, nine, or 10 or more) monovalent C5 inhibitor (e.g., a single chain anti-C5 antibody or a Fab fragment of the antibody) molecule(s) per every C5 molecule in the patient's blood. For example, in some embodiments a monovalent anti-C5 antibody (e.g., a single chain antibody or a Fab antibody fragment) can be administered to a patient in an amount and with a frequency effective to maintain a concentration of at least 1.5 (e.g., at least 1.6, 1.7, 1.8, 1.9, 2, 3, 4, 5, 6, or 7 or more) monovalent anti-C5 antibodies per C5 molecule in the blood. In some embodiments of any of the methods described herein, an anti-C5 antibody is administered to the patient in an amount and with a frequency that are effective to maintain a concentration of at least 40 (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 110, or 120 or more) µg of the antibody per milliliter of the patient's blood. Exemplary chronic dosing strategies are described herein (see, e.g., Tables 1 and 2).

In some embodiments, the C5 inhibitor (or C5a inhibitor) can be administered to a subject even after one or more symptoms have been ameliorated. Monitoring a subject (e.g., a human patient) for an improvement in a complement-associated disorder, as defined herein, means evaluating the subject for a change in a disease parameter, e.g., an improvement in one or more symptoms of the disease. Such symptoms include any of the symptoms of complement-associated disorders described herein. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for any of the complement-associated disorders described herein.

In some embodiments, the complement inhibitor can be chronically administered to a patient in need thereof in an amount and with a frequency that are effective to reduce and maintain serum hemolytic activity at less than or equal to 20 (e.g., 19, 18, 17, 16, 15, 14, 13, 12, 11, 10, 9, 8, 7, 6, or even below 5) %. See, e.g., Hill et al. (2005) *Blood* 106(7):2559. In some embodiments, the complement inhibitor can be administered to a patient in an amount and with a frequency that are effective to maintain serum lactate dehydrogenase (LDH) levels at within at least 20 (e.g., 19, 18, 17, 16, 15, 14, 13, 12, 11, 10, 9, 8, 7, 6, or even below 5) % of the normal range for LDH. See Hill et al. (2005) supra. In some embodiments, the complement inhibitor is administered to the patient in an amount and with a frequency that are effective to maintain a serum LDH level less than 550 (e.g., less than 540, 530, 520, 510, 500, 490, 480, 470, 450, 440, 430, 420, 410, 400, or less than 300) IU/L. In some embodiments, administration (e.g., chronic administration) of a C5 inhibitor (e.g., an anti-C5 antibody such as eculizumab) or a C5a inhibitor (e.g., an anti-C5a antibody) results in amelioration of one or more of a patient's symptoms to within 40 (e.g., 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or even 1) % of its normal level or value. For example, in some embodiments, the elevated blood pressure in an aHUS patient treated (e.g., chronically treated) with an anti-C5 antibody can be reduced to a level that is within 40% of the level that is normal for a person of the patient's age, race, height, weight, sex, and physical health.

In some embodiments, the complement inhibitor (e.g., a C5 inhibitor or C5a inhibitor) is administered to a subject even after the patient has entered clinical remission. Determining clinical remission of a complement-associated disorder is well within the skill set of the skilled artisan in medicine. For example, elements determinative of clinical remission for aHUS are described in, e.g., Nürnberger et al. (2009) *N Engl J Med* 360(5):542-544. Clinical remission for CAPS is described in, e.g., Manner et al. (2008) *Am J Med Sci* 335(5):394-397.

The disclosure also provides methods for allogeneic organ or tissue transplantation. The method includes transplanting an organ or tissue into a patient in need thereof, wherein prior to and following the transplanting a C5 inhibitor is administered to the patient in an amount and with a frequency effective to substantially inhibit systemic complement activity in the patient. As described herein, the C5 inhibitor (e.g., the anti-C5 antibody) can be administered in an amount and with a frequency to maintain a concentration of at least one C5 inhibitor molecule (e.g., at least one anti-C5 antibody) per C5 molecule in the patient's blood. In some embodiments, a monovalent anti-C5 antibody (e.g., a single chain antibody or a Fab antibody fragment) can be administered to a patient in an amount with a frequency effective to maintain a concentration of at least 1.5 (e.g., at least 1.6, 1.7, 1.8, 1.9, 2, 3, 4, 5, 6, or 7 or more) monovalent anti-C5 antibodies per C5 molecule in the blood. In some embodiments, the C5 inhibitor (e.g., the anti-C5 antibody) can be administered to the patient in an amount and with a frequency to maintain a concentration of at least at least 40 (e.g., 41, 42, 43, 44, 45, 46, 47, 48, 48, 50, 51, 52, 53, 54, 55, 56, 57, 58, 59, 60, 61, 62, 63, 64, 65, 66, 67, 68, 69, 70, 75, 80, 85, 90, 95, 100, 110, or 120 or more) μg of the inhibitor (e.g., the anti-C5 antibody) in the patient's blood. In some embodiments, at least 800 (e.g., at least 810, 820, 830, 840, 850, 860, 870, 880, 890, 900, 910, 920, 930, 940, 950, 960, 970, 980, 990, 1000, 1100, or 1200 or more) mg of the anti-C5 antibody (e.g., eculizumab) is administered to the patient less than 24 (e.g., less than 23, 22, 21, 20, 19, 18, 17, 16, 15, 14, 13, 12, 11, 10, 9, 8, 7, 6, 5, 4, 3, or less than 2) hours prior to transplanting the organ or tissue to the patient. In some embodiments, the methods can also include, prior to the transplanting, contacting (e.g., soaking) the donor organ or tissue with a C5 inhibitor (e.g., an anti-C5 antibody such as eculizumab) for an amount of time and under conditions that inhibit complement activation in the organ or tissue upon transplantation. The organ can be, e.g., skin, a kidney, heart, lung, limb (e.g., finger or toe), or liver. In some embodiments, the methods can include administering a C5 inhibitor (e.g., an anti-C5 antibody) to the donor patient prior to removal of the organ or tissue for transplant. The patient can have, be at risk for developing, or be suspected of having aHUS. In some embodiments, at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody is administered to the patient less than 24 (e.g., less than 23, 22, 21, 20, 19, 18, 17, 16, 15, 14, 13, 12, 11, 10, 9, 8, 7, 6, 5, 4, 3, or less than 2) hours following the transplanting. In some embodiments, the anti-C5 antibody is chronically administered to the patient following the transplanting. For example, the anti-C5 antibody can be chronically administered to the patient for at least 9 weeks (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) under the following dosing schedule: at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody less than 24 hours after transplanting the organ or tissue; at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody once per week for four weeks after the initial post-transplant dose; at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody once during the fifth week; and at least 700 (e.g., at least 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, or 1200 or more) mg of the anti-C5 antibody bi-weekly thereafter for the remainder of the dosing schedule. In a preferred embodiment, the anti-C5 antibody is administered such that the first four doses are at least 900 mg of the antibody; 1200 mg is administered on the fifth week; and 1200 mg is administered to the patient bi-weekly thereafter for the remainder of the chronic treatment schedule. Addition exemplary dosing schedules are provided in Tables 1 and 2.

In some embodiments, the methods include administering an immunosuppressant to the patient. Suitable immunosuppressants for use in the methods include, but are not limited to, ATG or ALG, OKT3, daclizumab, basiliximab, corticosteroids, 15-deoxyspergualin, cyclosporins, tacrolimus, azathioprine, methotrexate, mycophenolate mofetil, 6-mercaptopurine, bredinin, brequinar, leflunamide, cyclophosphamide, sirolimus, anti-CD4 monoclonal antibodies, CTLA4-Ig, anti-CD154 monoclonal antibodies, anti-LFA1 monoclonal antibodies, anti-LFA-3 monoclonal antibodies, anti-CD2 monoclonal antibodies, and anti-CD45 antibodies.

Types of organs or tissues that can be transplanted using the methods described herein include, e.g., heart, kidney, lung, pancreas, liver, vascular tissue, eye, cornea, lens, skin, bone marrow, muscle, connective tissue, gastrointestinal tissue, nervous tissue, bone, stem cells, islets, cartilage, hepatocytes, and hematopoietic cells.

In some embodiments, the transplant methods will result in prolongation of the graft in the recipient patient by at least one month (e.g., three, four, five, six, seven, eight, nine, 10, 11, or 12 months or 1, 2, 3, 4, 5, 6, 7, 8, 9, or even 10 years or more).

Ex Vivo Approaches.

An ex vivo strategy for treating or preventing a complement-associated disorder (e.g., an AP-associated disorder or a CP-associated disorder) can involve transfecting or transducing one or more cells obtained from a subject with a polynucleotide encoding a complement inhibitor (e.g., an anti-C5 antibody, anti-C5a antibody, or a nucleic acid (e.g., a siRNA) that binds to and promotes inactivation of a C5 mRNA in a mammalian cell) described herein. For example, the cells can be transfected with a single vector encoding a heavy and light chain of an antibody that binds to C5 protein, or the cells can be transfected with a first vector encoding a heavy chain and a second vector encoding a light chain of the antibody.

The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells can act as a source (e.g., sustained or periodic source) of the C5 inhibitor (e.g., anti-C5 antibody, anti-C5a antibody, or nucleic acid (above)) for as long as they survive in the subject. In some embodiments, the vectors and/or cells can be configured for inducible or repressible expression of the C5 inhibitor (see, e.g., Schockett et al. (1996) *Proc Natl Acad Sci USA* 93: 5173-5176 and U.S. Pat. No. 7,056,897).

Preferably, the cells are obtained from the subject (autologous), but can potentially be obtained from a subject of the same species other than the subject (allogeneic).

Suitable methods for obtaining cells from a subject and transducing or transfecting the cells are known in the art of molecular biology. For example, the transduction step can be accomplished by any standard means used for ex vivo gene therapy, including calcium phosphate, lipofection, electroporation, viral infection (see above), and biolistic gene transfer. (See, e.g., Sambrook et al. (supra) and Ausubel et al. (1992) "Current Protocols in Molecular Biology," Greene Publishing Associates.) Alternatively, liposomes or polymeric microparticles can be used. Cells that have been successfully transduced can be selected, for example, for expression of the coding sequence or of a drug resistance gene.

Kits

The disclosure also features articles of manufacture or kits, which include a container with a label; and a composition containing one or more complement inhibitors described herein. For example, the kit can contain one or more of an anti-C5a antibody, an anti-C5 antibody, and a nucleic acid (e.g., an siRNA or antisense nucleic acid) that binds to and promotes inactivation of a C5 mRNA in a mammalian cell. The label indicates that the composition is to be administered to a subject (e.g., a human) having, suspected of having, or at risk for developing, a complement-associated disorder (e.g., an AP- or CP-associated disorder) such as DDD, aHUS, TTP, HELLP, RA, AMD, tHUS, MG, CAD, PCH, CAPS, Degos disease, or any other complement pathway-associated disorder described herein. The kit can, optionally, include a means for administering the composition to the subject. For example, the kits can include one or more syringes.

In some embodiments, the kits can further include one or more additional active agents such as any of those described herein. For example, the kits can include one or more corticosteroids, anti-hypertensives, immunosuppressives, and anti-seizure agents.

The following examples are intended to illustrate, not limit, the invention.

Example 1

A human adult patient is identified by a medical practitioner as having an inherited form of aHUS. Once a week for four weeks the patient is administered a composition containing eculizumab at a dose of 900 mg. The patient then receives at least 1200 mg of eculizumab once during the fifth week and at least 1200 mg of eculizumab bi-weekly thereafter. The patient and medical practitioner observe a substantial improvement in at least two known symptoms of aHUS during the initial treatment. Eculizumab is chronically administered to the patient even after the medical practitioner determines that the aHUS is in remission.

Example 2

A human patient weighing around 25 kg is identified by a medical practitioner as having aHUS. Once a week for two weeks the patient is administered a composition containing eculizumab at a dose of at least 600 mg. The patient then receives at least 600 mg of eculizumab once during the third week and at least 600 mg of eculizumab bi-weekly thereafter. The patient and medical practitioner observe a substantial improvement in at least two known symptoms of aHUS during the initial treatment. Eculizumab is chronically administered to the patient even after the medical practitioner determines that the aHUS is in remission in order to prevent a recurrence of aHUS in the patient.

Example 3

A human patient weighing around 35 kg is identified by a medical practitioner as having CAPS. Once a week for two weeks the patient is administered a composition containing eculizumab at a dose of at least 600 mg. The patient then receives at least 900 mg of eculizumab once during the third week and at least 900 mg of eculizumab bi-weekly thereafter. The patient and medical practitioner observe a substantial improvement in at least two known symptoms of CAPS during the initial treatment. Eculizumab is chronically administered to the patient even after the medical practitioner determines that the CAPS is in remission in order to prevent, or substantially reduce the likelihood of, a recurrence of CAPS in the patient.

Example 4

A human patient weighing around 7 kg is identified by a medical practitioner as having aHUS. The patient has TMA in her kidneys as a result of the aHUS. For one week the patient is administered a composition containing eculizumab at a dose of at least 300 mg. The patient then receives at least 300 mg of eculizumab once during the second week and at least 300 mg of eculizumab every three weeks thereafter. The patient and medical practitioner observe a substantial improvement in at least two known symptoms of aHUS during the initial treatment. The medical practitioner also observes that the TMA in the patient's kidneys resolves and no new TMA occurs while the patient is being chronically administered eculizumab. Eculizumab is chronically administered to the patient even after the medical practitioner determines that the aHUS is in remission in order to prevent, or substantially reduce the likelihood of, a recurrence of aHUS in the patient and any further damage to her kidneys that could result from recurrence.

Example 5

A human patient in need of a kidney transplant is intravenously administered eculizumab at a dose of 1200 mg less than 24 hours before the transplant operation. An allogeneic kidney is transplanted into the patient. Less than 24 hours after the kidney transplant, the patient is administered another 1200 mg of eculizumab. Once a week for four weeks following the first post-operation dose of eculizumab, the patient receives 900 mg of eculizumab. The patient receives 1200 mg of eculizumab on the fifth week after the initial post-operation dose of eculizumab and then is maintained on a dosing schedule that includes 1200 mg of eculizumab bi-weekly thereafter. The medical practitioner observes a substantial improvement in the survival of the transplanted kidney in the patient.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating antibody-mediated rejection (AMR) in a patient having a kidney transplant, the method comprising intravenously administering to the patient:
   1200 mg of eculizumab less than 24 hours before or during the transplant operation and one post-operative dose of eculizumab within 24 hours of the transplant operation;
   900 mg of eculizumab once a week for four weeks after the post-operative dose; and
   1200 mg of eculizumab on week five after the post-operative dose and bi-weekly thereafter.

2. The method of claim 1, wherein the eculizumab is administered to the patient in an amount and with a frequency to maintain at least 50 µg of eculizumab per milliliter of the patient's blood.

3. The method of claim 1, wherein the eculizumab is administered to the patient in an amount and with a frequency to maintain at least 100 µg of eculizumab per milliliter of the patient's blood.

4. The method of claim 1, wherein the eculizumab is administered to the patient in an amount and with a frequency to maintain a concentration of at least 0.7 molecules of eculizumab per every C5 molecule in the patient's blood.

* * * * *

UNITED STATES PATENT AND TRADEMARK OFFICE
CERTIFICATE OF CORRECTION

PATENT NO.        : 9,771,418 B2
APPLICATION NO.   : 15/243290
DATED             : September 26, 2017
INVENTOR(S)       : Russell P. Rother et al.

Page 1 of 3

It is certified that error appears in the above-identified patent and that said Letters Patent is hereby corrected as shown below:

On the Title Page

On page 2, in Column 1, under "Other Publications", Line 16, delete "theInternet:" and insert -- the Internet: --, therefor.

On page 2, in Column 1, under "Other Publications", Line 20, delete "Hemoglobinuira" and insert -- Hemoglobinuria --, therefor.

On page 2, in Column 1, under "Other Publications", Line 25, delete "Phamaceuticals:" and insert -- Pharmaceuticals: --, therefor.

On page 2, in Column 1, under "Other Publications", Line 29, delete "Pharmaceuitcals" and insert -- Pharmaceuticals --, therefor.

On page 2, in Column 2, under "Other Publications", Line 13, delete "Retrived" and insert -- Retrieved --, therefor.

On page 2, in Column 2, under "Other Publications", Line 19, delete "XP055293282,Retrieved" and insert -- XP055293282, Retrieved --, therefor.

On page 2, in Column 2, under "Other Publications", Line 34, delete "Insrum." and insert -- Instrum. --, therefor.

On page 3, in Column 1, under "Other Publications", Line 34, delete "hemglobinuria," and insert -- hemoglobinuria, --, therefor.

On page 3, in Column 2, under "Other Publications", Line 14, delete "PediatiricTransplant" and insert -- Pediatric Transplant --, therefor.

Signed and Sealed this
Fifth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,771,418 B2

On page 3, in Column 2, under "Other Publications", Line 54, delete "Manuar" and insert -- Manual --, therefor.

On page 4, in Column 1, under "Other Publications", Line 15, delete "Medelian" and insert -- Mendelian --, therefor.

In the Specification

In Column 5, Line 45, delete "NOs:4" and insert -- NO:4 --, therefor.

In Column 6, Line 59, delete "Willibrand" and insert -- Willebrand --, therefor.

In Column 24, Line 2, delete "anaphylatoxic" and insert -- anaphylatoxin --, therefor.

In Columns 29-30, Line 67 (Column 29), Line 1 (Column 30), delete "BIAtechnology" and insert -- BIOtechnology --, therefor.

In Column 42, Line 25, delete "(1991)J" and insert -- (1991) J. --, therefor.

In Column 42, Line 26, delete "(1991)J." and insert -- (1991) J. --, therefor.

In Column 43, Line 41, delete "MEW" and insert -- MHC --, therefor.

In Column 45, Line 29, delete "(1983)Mol." and insert -- (1983) Mol. --, therefor.

In Column 46, Line 67, delete "sialastic" and insert -- silastic --, therefor.

In Column 47, Line 44, delete "µs/kg," and insert -- µg/kg, --, therefor.

In Column 47, Line 44, delete "µs/kg," and insert -- µg/kg, --, therefor.

In Column 47, Line 44, delete "µs/kg," and insert -- µg/kg, --, therefor.

In Column 47, Line 45, delete "µs/kg," and insert -- µg/kg, --, therefor.

In Column 47, Line 48, delete "µs/kg," and insert -- µg/kg, --, therefor.

In Column 47, Line 48, delete "µs/kg," and insert -- µg/kg, --, therefor.

In Column 47, Line 48, delete "µs/kg," and insert -- µg/kg, --, therefor.

In Column 47, Line 48, delete "µs/kg," and insert -- µg/kg, --, therefor.

In Column 47, Line 49, delete "µs/kg," and insert -- µg/kg, --, therefor.

In Column 50, Line 55, delete "sp." and insert -- spp. --, therefor.

CERTIFICATE OF CORRECTION (continued)
U.S. Pat. No. 9,771,418 B2

In Column 53, Line 4, delete "(Budep)" and insert -- (Budap) --, therefor.

In Column 54, Line 33, delete "(2006)J" and insert -- (2006) J. --, therefor.

In Column 54, Line 33, delete "(1989)J" and insert -- (1989) J. --, therefor.

In Column 54, Line 55, delete "CHSO," and insert -- CH50, --, therefor.

In Column 62, Line 7, delete "leflunamide," and insert -- leflunomide, --, therefor.